US012421308B2

(12) United States Patent
Dhanji et al.

(10) Patent No.: US 12,421,308 B2
(45) Date of Patent: Sep. 23, 2025

(54) ANTI-G-CSF ANTIBODIES AND USES THEREOF

(71) Applicant: ME THERAPEUTICS INC., North Vancouver (CA)

(72) Inventors: Salim Dhanji, North Vancouver (CA); John Priatel, Vancouver (CA); Kenneth Harder, North Vancouver (CA); Traian Sulea, Kirkland (CA); Jason Baardsnes, Montreal (CA)

(73) Assignee: ME Therapeutics Inc.

( * ) Notice: Subject to any disclaimer, the term of this patent is extended or adjusted under 35 U.S.C. 154(b) by 870 days.

(21) Appl. No.: 16/484,426

(22) PCT Filed: Feb. 7, 2018

(86) PCT No.: PCT/CA2018/050143
§ 371 (c)(1),
(2) Date: Aug. 7, 2019

(87) PCT Pub. No.: WO2018/145206
PCT Pub. Date: Aug. 16, 2018

(65) Prior Publication Data
US 2023/0159631 A1    May 25, 2023

Related U.S. Application Data

(60) Provisional application No. 62/455,991, filed on Feb. 7, 2017.

(51) Int. Cl.
*C07K 16/24* (2006.01)
*A61K 39/00* (2006.01)
*A61P 35/00* (2006.01)

(52) U.S. Cl.
CPC ........... *C07K 16/243* (2013.01); *A61P 35/00* (2018.01); *A61K 2039/505* (2013.01);
(Continued)

(58) Field of Classification Search
CPC .............. C07K 16/243; C07K 2317/24; C07K 2317/76; C07K 2317/92; A61P 35/00; A61K 2039/505
See application file for complete search history.

(56) References Cited

U.S. PATENT DOCUMENTS

2016/0368980 A1    12/2016    Morris

FOREIGN PATENT DOCUMENTS

| EP | 0225583 A2 | 6/1987 |
| EP | 2459591 A1 | 6/2012 |

(Continued)

OTHER PUBLICATIONS

Chen et al., Enhancement and destruction of antibody function by somatic mutation: unequal occurrence is controlled by V gene combinatorial associations. Embo J. Jun. 15, 1995;14(12):2784-94. (Year: 1995).*

(Continued)

*Primary Examiner* — Aurora M Fontainhas
*Assistant Examiner* — Selam Berhane
(74) *Attorney, Agent, or Firm* — McCarthy Tétrault LLP

(57) ABSTRACT

The present application discloses methods of making anti-G-CSF antibodies, anti-G-CSF antibodies, methods of screening the activity of anti-G-CSF antibodies, pharmaceutical compositions of anti-G-CSF antibodies, kits containing anti-G-CSF antibodies, and methods of using anti-G-CSF antibodies to treat a disease.

5 Claims, 15 Drawing Sheets

Specification includes a Sequence Listing.

(52) U.S. Cl.
CPC ...... *C07K 2317/24* (2013.01); *C07K 2317/76* (2013.01); *C07K 2317/92* (2013.01)

(56) References Cited

FOREIGN PATENT DOCUMENTS

| JP | H05115297 A | 5/1993 |
|---|---|---|
| WO | 2004017727 A1 | 3/2004 |
| WO | 2004043353 A2 | 5/2004 |
| WO | 2011014750 A1 | 2/2011 |

OTHER PUBLICATIONS

Kussie, Paul H., "A Single Engineered Amino Acid Substitution Changes Antibody Fine Specificity", 1994, Journal of Immunology 152(1): pp. 146-152. (Year: 1994).*

Koenig et al., Mutational landscape of antibody variable domains reveals a switch modulating the interdomain conformational dynamics and antigen binding. PNAS Jan. 24, 2017 114 (4) E486-E495; first published Jan. 5, 2017; (Year: 2017).*

International Preliminary Report on Patentability (Chapter 1) dated Aug. 13, 2019 mailed in corresponding International application No. PCT/CA2018/050143.

Morris, K. T. et al "Anti-G-CSF treatment induces protective tumor immunity in mouse colon cancer by promoting NK cell, macrophage and T cell responses", Oncotarget, vol. 6, No. 26 pp. 22338-22347.

Extended European Search Report dated Nov. 10, 2020 issued in the corresponding European Patent Application No. 18751734.7.

Layton J E et al: "Identification of a Functional Domain of Human Granulocyte Colony-Stimulating Factor Using Neutralizing Monoclonal Antibodies", Journal of Biological Chemistry, American Society for Biochemistry and Molecular Biology, US, vol. 266, No. 35, Dec. 15, 1991 (Dec. 15, 1991), pp. 23815-23823, XP002919518, ISSN: 0021-9258.

Jesus Banuelos et al.: "Granulocyte colony-stimulating factor blockade enables dexamethasone to inhibit lipopolysaccharide-induced murine lung neutrophils", PLOS One, vol. 12, No. 5, Jan. 1, 2017 (Jan. 1, 2017), pp. e0177884, XP055616661, DOI: 10.1371/journal.pone.01 77884.

* cited by examiner

Figure 1

A.    Plate Layout

NFS-60 Plate 1 Layout

|   | 1 | 2 | 3 | 4 | 5 | 6 | 7 | 8 | 9 | 10 | 11 | 12 |
|---|---|---|---|---|---|---|---|---|---|----|----|----|
| A |   |   |   |   |   |   |   |   |   |    |    |    |
| B |   | 1A1 | 1A2 | 1A6 | 1A9 | 1B11 | 1C7 | 1D5 | 1G2 | NFS + hM-CSF | IM SER. 1/100 |    |
| C |   | 2A6 | 2A12 | 2 E1 | 2 E10 | 2F4 | 2F6 | 2H11 | 3A1 | NFS + hM-CSF | IM SER. 1/500 |    |
| D |   | 3A3 | 3B2 | 3B3 | 3C3 | 3D8 | 3 E9 | 3F9 | 3G5 | NFS + hG-CSF | NAIVE SER. 1/100 |    |
| E |   | 3G10 | 4D2 | 4G5 | 4G7 | 4H8 | 5A3 | 5B5 | 5B9 | NFS + hG-CSF | NAIVE SER. 1/500 |    |
| F |   | 5 E11 | 5 E12 | 5H11 | 5H12 | 6A9 | 6A10 | 6B3 | 6D7 | NFS w/o cytokine | NFS w/o cytokine |    |
| G |   | 6F3 | 6F5 | 6G2 | 6G5 | 6G9 | 7B6 | 7C3 | 7D5 |    |    |    |
| H |   |   |   |   |   |   |   |   |   |    |    |    |

NFS-60 Plate 2 Layout

|   | 1 | 2 | 3 | 4 | 5 | 6 | 7 | 8 | 9 | 10 | 11 | 12 |
|---|---|---|---|---|---|---|---|---|---|----|----|----|
| A |   |   |   |   |   |   |   |   |   |    |    |    |
| B |   | 2A5 | 7F8 | 7G1 | 7G8 | 7G10 | 7H3 | 7H6 | 8A7 | NFS + hM-CSF | IM SER. 1/100 |    |
| C |   | 3A2 | 8C11 | 8D5 | 8D6 | 8G3 | 8H1 | 8H5 | 8H12 | NFS + hM-CSF | IM SER. 1/500 |    |
| D |   | 3G7 | 9C11 | 9D1 | 9D8 | 9F6 | 9G12 | 9H1 | 9H5 | NFS + hG-CSF | NAIVE SER. 1/100 |    |
| E |   | 5C2 | 8B8 | 8C2 | 10D2 | 10F6 | 10G1 | NFS w/o cytokine | NFS w/o cytokine | NFS + hG-CSF | NAIVE SER. 1/500 |    |
| F |   | 6D11 | 9A1 | 9B7 | 10G11 | 10H8 | 10H12 |   |   |    |    |    |
| G |   | 7F3 | 10B9 | 10C7 |   |   |   |   |   |    |    |    |
| H |   |   |   |   |   |   |   |   |   |    |    |    |

B.    Cell counts plate 1 (raw cell counts from macsquant)

|   | 1 | 2 | 3 | 4 | 5 | 6 | 7 | 8 | 9 | 10 | 11 | 12 |
|---|---|---|---|---|---|---|---|---|---|----|----|----|
| A |   |   |   |   |   |   |   |   |   |    |    |    |
| B |   | 3496 | 1105 | 1972 | 4962 | 40 | 262 | 6116 | 4836 | 26109 | 147 |    |
| C |   | 6606 | 8069 | 5522 | 5467 | 7397 | 213 | 5740 | 2621 | 28591 | 529 |    |
| D |   | 40 | 55 | 28 | 8581 | 7550 | 7284 | 5039 | 32 | 1716 | 11236 |    |
| E |   | 2467 | 5010 | 7959 | 35 | 1488 | 6977 | 329 | 7765 | 6946 | 11424 |    |
| F |   | 3597 | 7553 | 5300 | 9313 | 1961 | 7199 | 5874 | 7877 | 155 | 144 |    |
| G |   | 83 | 250 | 4712 | 5571 | 3392 | 3037 | 2498 | 4327 |    |    |    |
| H |   |   |   |   |   |   |   |   |   |    |    |    |

NFS-60 cells + hG-CSF = D10, E10
NFS-60 cells − hG-CSF = F10, F11 plate 2 (raw cell counts from macsquant)

|   | 1 | 2 | 3 | 4 | 5 | 6 | 7 | 8 | 9 | 10 | 11 | 12 |
|---|---|---|---|---|---|---|---|---|---|----|----|----|
| A |   |   |   |   |   |   |   |   |   |    |    |    |
| B |   | 2163 | 2437 | 2323 | 765 | 6598 | 228 | 189 | 2341 | 31059 | 123 |    |
| C |   | 2414 | 4401 | 3424 | 4750 | 4077 | 8728 | 4965 | 1601 | 35189 | 595 |    |
| D |   | 3689 | 140 | 3297 | 246 | 5842 | 682 | 323 | 8088 | 1429 | 9152 |    |
| E |   | 3367 | 5114 | 6515 | 8878 | 3107 | 108 | 83 | 139 | 2002 | 8101 |    |
| F |   | 2826 | 2271 | 52 | 4344 | 8881 | 6388 |   |   |    |    |    |
| G |   | 2089 | 19 | 2575 |   |   |   |   |   |    |    |    |
| H |   |   |   |   |   |   |   |   |   |    |    |    |

| ID | Description Name | Humanization % hum. V-FR | #m-res. V-FR | #m-res. V-FR exposed | #highly-promisc. TCEs | Antigen binding (SPR) K_D (nM) | K_off (10^-4 × s^-1) | Thermal stability (DSC) T_m1 (°C) | T_m2 (°C) | T_m3 (°C) | Main peak (%) | Aggregation (UPLC-SEC) HMW (%) | LMW (%) |
|---|---|---|---|---|---|---|---|---|---|---|---|---|---|
| 0 | murine* | 82.1 | 29 | 21 | >6 | 0.06 | 0.5 | N/A | N/A | N/A | N/A | N/A | N/A |
| 1 | chimeric | 82.1 | 29 | 21 | 6 | 0.10 | 1.2 | 71 | 80 | 82 | 100 | 0 | 0 |
| 7 | h1L/h1H | 100 | 0 | 0 | 1 | 0.29 | 1.7 | 71 | 81 | 85 | 100 | 0 | 0 |
| 8 | h1L/h2H | 97.5 | 4 | 0 | 2 | 0.29 | 1.7 | 71 | 81 | 84 | 100 | 0 | 0 |
| 9 | h1L/h3H | 96.3 | 6 | 2 | 2 | 0.19 | 1.7 | 71 | 82 | 84 | 99.9 | 0.1 | 0 |
| 10 | h1L/h4H | 95.1 | 8 | 4 | 2 | 0.16 | 1.5 | 71 | 80 | 81 | 99.1 | 0.9 | 0 |
| 12 | h2L/h1H | 99.4 | 1 | 0 | 1 | 0.20 | 1.1 | 71 | 82 | 84 | 100 | 0 | 0 |
| 13 | h2L/h2H | 96.9 | 5 | 0 | 2 | 0.20 | 1.2 | 71 | 81 | 84 | 100 | 0 | 0 |
| 14 | h2L/h3H | 95.7 | 7 | 2 | 2 | 0.15 | 1.3 | 71 | 81 | 83 | 99.9 | 0.1 | 0 |
| 15 | h2L/h4H | 94.4 | 9 | 4 | 2 | 0.12 | 1.0 | 71 | 79 | 81 | 100 | 0 | 0 |

SEQUENCE LISTING

<160> NUMBER OF SEQ ID NOS: 30

<210> SEQ ID NO 1
<211> LENGTH: 5
<212> TYPE: PRT
<213> ORGANISM: Mus musculus

<400> SEQUENCE: 1

Ile Tyr Thr Met His
1               5

<210> SEQ ID NO 2
<211> LENGTH: 17
<212> TYPE: PRT
<213> ORGANISM: Mus musculus

<400> SEQUENCE: 2

Tyr Ile Asn Pro Ser Ile Gly Tyr Ala Asn Tyr Asn Gln Lys Phe Arg
1               5                   10                  15

Asp

<210> SEQ ID NO 3
<211> LENGTH: 10
<212> TYPE: PRT
<213> ORGANISM: Mus musculus

<400> SEQUENCE: 3

Gly Gly Tyr Gly Asp Ser Leu Phe Ala Tyr
1               5                   10

<210> SEQ ID NO 4
<211> LENGTH: 16
<212> TYPE: PRT
<213> ORGANISM: Mus musculus

<400> SEQUENCE: 4

Arg Ser Ser Lys Ser Leu Leu His Ser Asn Gly Ile Thr Tyr Leu Tyr
1               5                   10                  15

<210> SEQ ID NO 5
<211> LENGTH: 7
<212> TYPE: PRT
<213> ORGANISM: Mus musculus

<400> SEQUENCE: 5

Gln Met Ser Asn Leu Ala Ser
1               5

<210> SEQ ID NO 6
<211> LENGTH: 9
<212> TYPE: PRT
<213> ORGANISM: Mus musculus

<400> SEQUENCE: 6

Ala Gln Asn Leu Glu Leu Pro Tyr Thr
1               5

<210> SEQ ID NO 7
<211> LENGTH: 119
<212> TYPE: PRT
<213> ORGANISM: Mus musculus

<400> SEQUENCE: 7

Gln Val His Leu Gln Gln Ser Gly Ala Glu Leu Ala Arg Pro Gly Ala

```
                1               5                   10                  15
            Ser Val Lys Met Ser Cys Lys Ala Ser Gly Tyr Thr Phe Pro Ile Tyr
                            20                  25                  30

Thr Met His Trp Ile Lys Gln Arg Pro Gly Gln Gly Leu Glu Trp Ile
                        35                  40                  45

Gly Tyr Ile Asn Pro Ser Ile Gly Tyr Ala Asn Tyr Asn Gln Lys Phe
                    50                  55                  60

Arg Asp Lys Ala Thr Leu Thr Ala Asp Lys Ser Ser Thr Ala Tyr
            65                  70                  75                  80

Met Gln Leu Ser Ser Leu Thr Ser Glu Asp Ser Ala Val Tyr Tyr Cys
                            85                  90                  95

Ala Arg Gly Gly Tyr Gly Asp Ser Leu Phe Ala Tyr Trp Gly Gln Gly
                        100                 105                 110

Thr Leu Val Thr Val Ser Ala
                        115

<210> SEQ ID NO 8
<211> LENGTH: 112
<212> TYPE: PRT
<213> ORGANISM: Mus musculus

<400> SEQUENCE: 8

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
            85                  90                  95

Leu Glu Leu Pro Tyr Thr Phe Gly Gly Gly Thr Lys Leu Glu Ile Lys
        100                 105                 110

<210> SEQ ID NO 9
<211> LENGTH: 5
<212> TYPE: PRT
<213> ORGANISM: Mus musculus

<400> SEQUENCE: 9

Pro Tyr Thr Met His
1               5

<210> SEQ ID NO 10
<211> LENGTH: 17
<212> TYPE: PRT
<213> ORGANISM: Mus musculus

<400> SEQUENCE: 10

Tyr Ile Asn Pro Ser Ile Asn Tyr Thr Asn Tyr Asn Gln Lys Phe Lys
1               5                   10                  15

Asp

<210> SEQ ID NO 11
<211> LENGTH: 9
```

<212> TYPE: PRT
<213> ORGANISM: Mus musculus

<400> SEQUENCE: 11

Arg Gly Ser Tyr Gly Asn Phe Asp Tyr
1               5

<210> SEQ ID NO 12
<211> LENGTH: 16
<212> TYPE: PRT
<213> ORGANISM: Mus musculus

<400> SEQUENCE: 12

Arg Ser Asn Lys Ser Leu Leu His Ser Asn Gly Ile Thr Tyr Leu Tyr
1               5                   10                  15

<210> SEQ ID NO 13
<211> LENGTH: 7
<212> TYPE: PRT
<213> ORGANISM: Mus musculus

<400> SEQUENCE: 13

Gln Met Ser Asn Leu Ala Ser
1               5

<210> SEQ ID NO 14
<211> LENGTH: 9
<212> TYPE: PRT
<213> ORGANISM: Mus musculus

<400> SEQUENCE: 14

Ala Gln Asn Leu Glu Leu Pro Leu Thr
1               5

<210> SEQ ID NO 15
<211> LENGTH: 118
<212> TYPE: PRT
<213> ORGANISM: Mus musculus

<400> SEQUENCE: 15

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Pro Tyr
                20                  25                  30

Thr Met His Trp Val Lys Gln Arg Pro Gly Gln Asp Leu Glu Trp Ile
            35                  40                  45

Gly Tyr Ile Asn Pro Ser Ile Asn Tyr Thr Asn Tyr Asn Gln Lys Phe
        50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Arg Gly Ser Tyr Gly Asn Phe Asp Tyr Trp Gly Gln Gly Thr
                100                 105                 110

Thr Leu Thr Val Ser Ser
            115

<210> SEQ ID NO 16
<211> LENGTH: 112
<212> TYPE: PRT
<213> ORGANISM: Mus musculus

<400> SEQUENCE: 16

| | | | | | | | | | | | | | | |
|---|---|---|---|---|---|---|---|---|---|---|---|---|---|---|
|Asp|Ile|Val|Met|Thr|Gln|Ala|Ala|Phe|Ser|Asn|Pro|Val|Thr|Leu|Gly
1| | | |5| | | | |10| | | | |15|

Thr Ser Ala Ser Ile Ser Cys Arg Ser Asn Lys Ser Leu Leu His Ser
           20                   25                   30

Asn Gly Ile Thr Tyr Leu Tyr Trp Tyr Leu Gln Lys Pro Gly Gln Ser
        35                   40                   45

Pro Gln Leu Leu Ile Tyr Gln Met Ser Asn Leu Ala Ser Gly Val Pro
50                   55                   60

Asp Arg Phe Ser Ser Gly Ser Gly Thr Asp Phe Thr Leu Arg Ile
65                   70                   75                   80

Ser Arg Val Glu Ala Glu Asp Val Gly Val Tyr Tyr Cys Ala Gln Asn
                 85                   90                   95

Leu Glu Leu Pro Leu Thr Phe Gly Ala Gly Thr Lys Leu Glu Leu Lys
        100                   105                  110

<210> SEQ ID NO 17
<211> LENGTH: 357
<212> TYPE: DNA
<213> ORGANISM: Mus musculus

<400> SEQUENCE: 17

```
caggtccacc tgcagcagtc tggggctgaa ctggcaagac ctggggcctc agtgaagatg     60
tcctgcaagg cttctggcta cacctttcct atctacacga tgcactggat aaaacagagg    120
cctggacagg gtctggaatg gattggatac attaatccta gcattggtta tgctaattac    180
aatcagaagt tcagggacaa ggccacattg actgcagaca atcctccag cacagcctac     240
atgcaactga gcagcctgac atctgaggac tctgcagtct attactgtgc aagaggggg     300
tatggtgact ccctctttgc ttactggggc caaggactc tggtcactgt ctctgca       357
```

<210> SEQ ID NO 18
<211> LENGTH: 336
<212> TYPE: DNA
<213> ORGANISM: Mus musculus

<400> SEQUENCE: 18

```
gatattgtga tgacgcaggc tgcattctcc aatccagtca ctcttggaac atcagcttcc     60
atctcctgca ggtctagtaa gagtctccta catagtaatg gcatcactta tttgtattgg    120
tatctgcaga agccaggcca gtctcctcag ctcctgattt atcagatgtc aaccttgcc     180
tcaggagtcc cagacaggtt cagtagcagt gggtcaggaa ctgatttcac actgagaatc    240
agcagagtgg aggctgagga tgtgggtgtt tattactgtg ctcaaaatct agaacttccg    300
tacacgttcg gagggggac caagctggaa ataaaa                              336
```

<210> SEQ ID NO 19
<211> LENGTH: 354
<212> TYPE: DNA
<213> ORGANISM: Mus musculus

<400> SEQUENCE: 19

```
caggtccagc tgcagcagtc tggggctgaa ctggcaagac ctggggcctc agtgaagatg     60
tcctgcaagg cttctggcta cacctttact ccctacacga tgcactgggt gaaacagagg    120
cctggacagg gtctggaatg gattggatac attaatccta gcattaatta ctactaattac    180
aatcagaagt tcaggacaa ggccacattg actgcagaca atcctccag cacagcctat     240
```

```
atgcaactga gcagcctgac atctgaggac tctgcagtct atttctgtgc aagaagaggg      300
tcttatggta actttgacta ctggggccaa ggcaccactc tcacagtctc ctca            354
```

<210> SEQ ID NO 20
<211> LENGTH: 336
<212> TYPE: DNA
<213> ORGANISM: Mus musculus

<400> SEQUENCE: 20

```
gatattgtga tgacgcaggc tgcattctcc aatccagtca ctcttggaac atcagcttcc       60
atctcctgca ggtctaataa gagtctccta catagtaatg gcatcactta tttgtattgg      120
tatctgcaga agccaggcca gtctcctcag ctcctgattt atcagatgtc caaccttgcc      180
tcaggagtcc cagacaggtt cagtagcagt gggtcaggaa ctgatttcac actgagaatc      240
agcagagtgg aggctgagga tgtgggtgtt tattactgtg ctcaaaatct agaacttccg      300
ctcacgttcg gtgctgggac caagctggag ctgaaa                                336
```

<210> SEQ ID NO 21
<211> LENGTH: 6
<212> TYPE: PRT
<213> ORGANISM: Artificial Sequence
<220> FEATURE:
<223> OTHER INFORMATION: Poly-histidine tag

<400> SEQUENCE: 21

His His His His His His
1               5

<210> SEQ ID NO 22
<211> LENGTH: 15
<212> TYPE: PRT
<213> ORGANISM: Artificial Sequence
<220> FEATURE:
<223> OTHER INFORMATION: GGGGS Linker

<400> SEQUENCE: 22

Gly Gly Gly Gly Ser Gly Gly Gly Gly Ser Gly Gly Gly Gly Ser
1               5                   10                  15

<210> SEQ ID NO 23
<211> LENGTH: 112
<212> TYPE: PRT
<213> ORGANISM: Artificial Sequence
<220> FEATURE:
<223> OTHER INFORMATION: 1B11 chimeric light chain (cL)

<400> SEQUENCE: 23

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
                20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Ala Ser Gly Val Pro
        50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Leu Glu Ile Lys

<210> SEQ ID NO 24
<211> LENGTH: 119
<212> TYPE: PRT
<213> ORGANISM: Artificial Sequence
<220> FEATURE:
<223> OTHER INFORMATION: 1B11 chimeric heavy chain (cH)

<400> SEQUENCE: 24

```
Gln Val His Leu Gln Gln Ser Gly Ala Glu Leu Ala Arg Pro Gly Ala
1               5                   10                  15

Ser Val Lys Met Ser Cys Lys Ala Ser Gly Tyr Thr Phe Pro Ile Tyr
            20                  25                  30

Thr Met His Trp Ile Lys Gln Arg Pro Gly Gln Gly Leu Glu Trp Ile
        35                  40                  45

Gly Tyr Ile Asn Pro Ser Ile Gly Tyr Ala Asn Tyr Asn Gln Lys Phe
    50                  55                  60

Arg Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Tyr Gly Asp Ser Leu Phe Ala Tyr Trp Gly Gln Gly
            100                 105                 110

Thr Leu Val Thr Val Ser Ala
        115
```

<210> SEQ ID NO 25
<211> LENGTH: 112
<212> TYPE: PRT
<213> ORGANISM: Artificial Sequence
<220> FEATURE:
<223> OTHER INFORMATION: 1B11 humanized light chain 1 (h1L)

<400> SEQUENCE: 25

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gln Gly Thr Lys Leu Glu Ile Lys
            100                 105                 110
```

<210> SEQ ID NO 26
<211> LENGTH: 112
<212> TYPE: PRT
<213> ORGANISM: Artificial Sequence
<220> FEATURE:
<223> OTHER INFORMATION: 1B11 humanized light chain 2 (h2L)

<400> SEQUENCE: 26

```
Asp Ile Val Met Thr Gln Ser Pro Leu Ser Leu Pro Val Thr Pro Gly
1               5                   10                  15
```

```
Glu Pro Ala Ser Ile Ser Cys Arg Ser Ser Lys Ser Leu Leu His Ser
                20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Ala Ser Gly Val Pro
    50                  55                  60

Asp Arg Phe Ser Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gln Gly Thr Lys Leu Glu Ile Lys
            100                 105                 110
```

<210> SEQ ID NO 27
<211> LENGTH: 119
<212> TYPE: PRT
<213> ORGANISM: Artificial Sequence
<220> FEATURE:
<223> OTHER INFORMATION: 1B11 humanized heavy chain 1 (h1H)

<400> SEQUENCE: 27

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Ile Tyr
                20                  25                  30

Thr Met His Trp Val Arg Gln Ala Pro Gly Gln Gly Leu Glu Trp Met
            35                  40                  45

Gly Tyr Ile Asn Pro Ser Ile Gly Tyr Ala Asn Tyr Asn Gln Lys Phe
    50                  55                  60

Arg Asp Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Gly Asp Ser Leu Phe Ala Tyr Trp Gly Gln Gly
            100                 105                 110

Thr Leu Val Thr Val Ser Ser
            115
```

<210> SEQ ID NO 28
<211> LENGTH: 119
<212> TYPE: PRT
<213> ORGANISM: Artificial Sequence
<220> FEATURE:
<223> OTHER INFORMATION: 1B11 humanized heavy chain 2 (h2H)

<400> SEQUENCE: 28

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Ile Tyr
                20                  25                  30

Thr Met His Trp Ile Arg Gln Ala Pro Gly Gln Gly Leu Glu Trp Ile
            35                  40                  45

Gly Tyr Ile Asn Pro Ser Ile Gly Tyr Ala Asn Tyr Asn Gln Lys Phe
    50                  55                  60

Arg Asp Arg Ala Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
```

```
                    85                  90                  95

Ala Arg Gly Gly Tyr Gly Asp Ser Leu Phe Ala Tyr Trp Gln Gly
            100                 105                 110

Thr Leu Val Thr Val Ser Ser
        115

<210> SEQ ID NO 29
<211> LENGTH: 119
<212> TYPE: PRT
<213> ORGANISM: Artificial Sequence
<220> FEATURE:
<223> OTHER INFORMATION: 1B11 humanized heavy chain 3 (h3H)

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Ile Tyr
            20                  25                  30

Thr Met His Trp Ile Lys Gln Ala Pro Gly Gln Gly Leu Glu Trp Ile
        35                  40                  45

Gly Tyr Ile Asn Pro Ser Ile Gly Tyr Ala Asn Tyr Asn Gln Lys Phe
    50                  55                  60

Arg Asp Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Gly Asp Ser Leu Phe Ala Tyr Trp Gln Gly
            100                 105                 110

Thr Leu Val Thr Val Ser Ser
        115

<210> SEQ ID NO 30
<211> LENGTH: 119
<212> TYPE: PRT
<213> ORGANISM: Artificial Sequence
<220> FEATURE:
<223> OTHER INFORMATION: 1B11 humanized heavy chain 4 (h4H)

<400> SEQUENCE: 30

Gln Val His Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Ile Tyr
            20                  25                  30

Thr Met His Trp Ile Lys Gln Ala Pro Gly Gln Gly Leu Glu Trp Ile
        35                  40                  45

Gly Tyr Ile Asn Pro Ser Ile Gly Tyr Ala Asn Tyr Asn Gln Lys Phe
    50                  55                  60

Arg Asp Lys Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Gly Asp Ser Leu Phe Ala Tyr Trp Gln Gly
            100                 105                 110

Thr Leu Val Thr Val Ser Ser
        115
```

ANTI-G-CSF ANTIBODIES AND USES THEREOF

CROSS REFERENCE TO RELATED APPLICATIONS

This application is a 371 of PCT Application No. PCT/CA2018/050143, filed on Feb. 7, 2018, which claims priority to U.S. Provisional Patent Application Ser. No. 62/455,991, filed on Feb. 7, 2017. The entirety of the contents of the referenced applications are hereby incorporated by reference.

BACKGROUND OF THE INVENTION

Cancer is one of the leading causes of death in the developed world and over 14 million new cases of cancer occur globally each year. Genetic and environmental factors can cause cancer and the risk of cancer increases significantly with age. Rates of cancer occurrences are increasing as people live longer and as lifestyle changes occur in the developing world. Cancer growth can be supported by ineffective immune system activation and chronic inflammation.

Infection or inflammation is often associated with the release of cytokines which play a biological role in the clearance of infection. During chronic inflammation, these same cytokines can play an important role in sustaining inflammation and disease symptoms. In addition, there is growing evidence that cytokines can influence pain by modifying neuronal signaling. Granulocyte colony stimulating factor (G-CSF) plays an important role in both cancer and chronic inflammatory diseases such as arthritis.

SUMMARY OF THE INVENTION

According to one aspect of the disclosure, there is provided an isolated or purified antibody, or antigen-binding fragment thereof, that binds to granulocyte colony stimulating factor (G-CSF), that comprises a heavy chain CDR1 referenced as SEQ ID NO: 1 or SEQ ID NO: 1 having a conservative substitution therein; a heavy chain CDR2 referenced as SEQ ID NO: 2 or SEQ ID NO: 2 having a conservative substitution therein; a heavy chain CDR3 referenced as SEQ ID NO: 3 or SEQ ID NO: 3 having a conservative substitution therein; a light chain CDR1 referenced as SEQ ID NO: 4 or SEQ ID NO: 4 having a conservative substitution therein; a light chain CDR2 referenced as SEQ ID NO: 5 or SEQ ID NO: 5 having a conservative substitution therein; and a light chain CDR3 referenced as SEQ ID NO: 6 or SEQ ID NO: 6 having a conservative substitution therein. In one instance, the isolated or purified antibody, or antigen-binding fragment thereof, comprises a heavy chain variable region referenced as SEQ ID NO: 7 and a light chain variable region referenced as SEQ ID NO: 8. In another instance, such an antibody is referred to as 1B11.

According to another aspect of the disclosure, there is provided an isolated or purified antibody, or antigen-binding fragment thereof, that binds to granulocyte colony stimulating factor (G-CSF), that comprises a heavy chain CDR1 referenced as SEQ ID NO: 9 or SEQ ID NO: 9 having a conservative substitution therein; a heavy chain CDR2 referenced as SEQ ID NO: 10 or SEQ ID NO: 10 having a conservative substitution therein; a heavy chain CDR3 referenced as SEQ ID NO: 11 or SEQ ID NO: 11 having a conservative substitution therein; a light chain CDR1 referenced as SEQ ID NO: 12 or SEQ ID NO: 12 having a conservative substitution therein; a light chain CDR2 referenced as SEQ ID NO: 13 or SEQ ID NO: 13 having a conservative substitution therein; and a light chain CDR3 referenced as SEQ ID NO: 14 or SEQ ID NO: 14 having a conservative substitution therein. In one instance, the isolated or purified antibody, or antigen-binding fragment thereof, comprises a heavy chain variable region referenced as SEQ ID NO: 15 and a light chain variable region referenced as SEQ ID NO: 16. In another instance, such an antibody is referred to as 3B3.

According to another aspect of the disclosure, there is provided an isolated or purified antibody, or antigen-binding fragment thereof, that binds to granulocyte colony stimulating factor (G-CSF), that comprises a heavy chain referenced as SEQ ID NO: 24, SEQ ID NO: 27, SEQ ID NO: 28, SEQ ID NO: 29, or SEQ ID NO: 30, all having a conservative substitution therein; and a light chain referenced as SEQ ID NO: 23, SEQ ID NO: 25, or SEQ ID: NO: 26, all having a conservative substitution therein.

According to another aspect of the disclosure, there is provided a nucleic acid encoding an antibody, or antigen-binding fragment thereof, described herein. In one instance, an anti-G-CSF antibody described herein has a variable heavy chain encoded by SEQ ID NO: 17 and a variable light chain encoded by SEQ ID NO: 18. In another instance, an anti-G-CSF antibody described herein has a variable heavy chain encoded by SEQ ID NO: 19 and a variable light chain encoded by SEQ ID NO: 20. An expression vector and/or a host cell may be prepared that comprises a nucleic acid sequence described herein or encoding a polypeptide sequence described herein.

In some embodiments, an isolated anti-G-CSF antibody, or antigen-binding fragment thereof, described herein comprises a binding affinity ($K_D$) to G-CSF of 2 nM or less as measured by surface plasmon resonance at 37° C.

In some embodiments, an antibody, or antigen-binding fragment thereof, described herein can be an IgG, an IgM, an IgE, an IgA, or an IgD, or is derived therefrom. When an antibody, or antigen-binding fragment thereof, is an IgG, the IgG can be an IgG1, an IgG2a, an IgG2b, an IgG3, or an IgG4.

In some embodiments, an antibody, or antigen-binding fragment thereof, described herein can comprise, in some instances, part or all of an Fc region.

In some embodiments, an antibody described herein can be, for example, a monoclonal antibody, a grafted antibody, a chimeric antibody, a human antibody, a humanized antibody, and the like.

In some embodiments, an antibody, or antigen-binding fragment thereof, described herein can be, for example, also a de-immunized antibody.

In some embodiments, an antigen-binding fragment can be a Fab fragment, a Fab' fragment, a F(ab)$_2$ fragment, an Fv fragment, an scFv fragment, a single chain binding polypeptide, a Fd fragment, a variable heavy chain, a variable light chain, a dAb fragment, single domain antibody, and the like.

In some embodiments, the isolated or purified antibody, or antigen-binding fragment thereof, has been engineered for increased clearance of G-CSF from circulation in the subject. In some embodiments, the bispecific antibody binds to G-CSF and an Fc receptor to allow for increased rate of clearance of the bound G-CSF from circulation in the subject.

In some embodiments, an antibody or antigen-binding fragment thereof, described herein can be conjugated to a therapeutic agent. A therapeutic agent can be, for example, a toxin, a drug, an enzyme, a cytokine, a radionuclide, a photodynamic agent, or the like.

In some embodiments, a toxin can be, for example, a ricin A chain, a mutant *Pseudomonas* exotoxins, a diphtheria toxoid, a streptonigrin, a boamycin, a saporin, a gelonin, a pokeweed antiviral protein, or the like.

In some embodiments, a drug can be, for example, daunorubicin, methotrexatee, calicheamicin, or other therapeutic agents known in the art.

In some embodiments, a radionuclide includes, but is not limited to, a radiometal.

In some embodiments, a cytokine can be, for example, a transforming growth factor (TGF; e.g., TGF-beta), an interleukin (IL), an interferon (IFN), or a tumor necrosis factor (TNF).

In some embodiments, a photodynamic agent can be, for example, a photoporphyrin or a derivative thereof.

According to another aspect of the disclosure, there is provided a pharmaceutical composition that comprises an antibody, or antigen-binding fragment thereof, described herein and a pharmaceutically acceptable carrier or excipient.

In some embodiments, the pharmaceutical composition further comprises an angiogenesis inhibitor that may be, for example, an anti-VEGF agent or a chemotherapeutic agent.

In some embodiments, a pharmaceutical composition may be formulated for administration orally, sublingually, via inhalation, transdermally, subcutaneously, intravenously, intra-arterially, intra-articularly, peri-articularly, or intra-muscularly.

According to another aspect of the disclosure, there is provided a method of treating a cancer in a subject in need thereof comprising administering to the subject a pharmaceutical composition described herein.

In some embodiments, a cancer may be, for example, a lung cancer, a breast cancer, an ovarian cancer, a colon cancer, a pancreatic cancer, a brain cancer, or a skin cancer.

According to another aspect of the disclosure, there is provided a method of treating arthritis in a subject in need thereof comprising administering to the subject a pharmaceutical composition described herein.

In some embodiments, a pharmaceutical composition can be administered intravenously, orally, sublingually, via inhalation, transdermally, subcutaneously, intra-arterially, intra-articularly, peri-articularly or intramuscularly.

In some embodiments, administration of the antibody, or antigen-binding fragment thereof, inhibits or neutralizes G-CSF activity.

In some embodiments, the antibody, or antigen-binding fragment thereof, increases dendritic cell development, dendritic cell maturation, or a combination thereof.

In some embodiments, after administration of the antibody, or antigen-binding fragment thereof, or a pharmaceutical composition comprising it, a subject exhibits a reduction in suppression of T-cells.

In some embodiments, kits, pharmaceutical packages, and other compositions may comprise the antibody, or antigen-binding fragment, pharmaceutical compositions, or the like described herein.

Additional aspects of the present disclosure will be apparent in view of the description which follows.

INCORPORATION BY REFERENCE

All publications, patents, and patent applications mentioned in this specification are herein incorporated by reference to the same extent as if each individual publication, patent, or patent application was specifically and individually indicated to be incorporated by reference.

The sequences described throughout the application are herein incorporated by reference.

BRIEF DISCLOSURE OF THE DRAWINGS

The novel features of the invention are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIGS. 1A-B. Several anti-G-CSF antibody clones neutralize the proliferation of NFS-60 cells in response to human G-CSF. A) $2.5 \times 10^3$ NFS-60 cells were cultured with 0.125 ng/mL of recombinant human G-CSF for 6 days in the presence of anti-G-CSF antibody clone supernatants (1/5 dilution). The panels show the plate layouts identifying the well location of each clone and right panels show the respective cell counts for each well. B) On day 6, cells were counted using MACSQUANT®.

FIG. 2. Anti-G-CSF antibodies neutralize a low concentration of 0.125 ng/mL human G-CSF (hG-CSF). $2.5 \times 10^3$ NFS-60 cells were cultured with 0.125 ng/mL of either recombinant human G-CSF for 6 days in the presence of anti-G-CSF antibody clone supernatants (1/5 dilution). On day 6 cells were counted using MACSQUANT®. *$p<0.05$ $p<0.01$ *$p<0.001$ ****$p<0.0001$ using a t-test FIG. 3. Anti-G-CSF antibodies neutralize a high concentration of 0.625 ng/mL human G-CSF (hG-CSF). $2.5 \times 10^3$ NFS-60 cells were cultured with 0.625 ng/mL of recombinant human G-CSF for 6 days in the presence of anti-G-CSF antibody clone supernatants (1/5 dilution). On day 6 cells were counted using MACSQUANT®. *$p<0.05$ $p<0.01$ *$p<0.001$ ****$p<0.0001$ using a t-test FIG. 4. Anti-G-CSF clones demonstrate greater activity against human than mouse G-CSF suggesting little cross reactivity across species. $2.5 \times 10^3$ NFS-60 cells were cultured with 0.125 ng/mL of either recombinant human G-CSF (left) or recombinant mouse G-CSF (right) for 6 days in the presence of anti-G-CSF antibody clone supernatants (1/5 dilution). On day 6 cells were counted using MACSQUANT®. All results are in triplicate and show the mean+SD. P values were calculated using a one way ANOVA followed by a Dunnett's multiple comparison test for significance compared to the G-CSF control. *$p<0.05$ $p<0.01$ *$p<0.001$ ****$p<0.0001$ FIGS. 5A-B. Anti-human G-CSF clones demonstrate activity against both glycosylated and non-glycosylated human G-CSF. $2.5 \times 10^3$ NFS-60 cells were cultured with either unglycosylated *E. coli* produced recombinant human G-CSF (left; A) or with glycosylated, CHO expressed human G-CSF (right; B) for 6 days in the presence of anti-G-CSF antibody clone supernatants (1/5 dilution) or purified antibody (10 µg/mL). On day 6 cells were counted using MACSQUANT®. All results are in triplicate and show the mean±SD and all results have a p-value <0.0001. The 0.1 and 0.2 designations refer to subclones for each primary antibody clone.

FIGS. 6A-D. 1B11.2 (A), 3A3.2 (B), 3B2.2 (C) and 2B3.2 (D) neutralized bioactivity of G-CSF in a dose-dependent manner. $2.5 \times 10^3$ NFS-60 cells were cultured with 0.125 ng/mL of recombinant human G-CSF for 6 days in the presence of anti-G-CSF antibody clone supernatants at various dilutions. On day 6 cells were counted using MACSQUANT®. All results are in triplicate and show the mean+SD.

FIG. 7. Neutralizing activity of 3B3 compared to 1B11. $2.5 \times 10^3$ NFS-60 cells were cultured with 0.125 ng/mL of recombinant human G-CSF for 6 days in the presence of various concentrations of purified anti-G-CSF antibody clone 3B3 (squares) or 1B11 (circles). On day 6 cells were counted using MACSQUANT®. All results are in triplicate and show the mean±SD.

FIG. 8. Anti-human G-CSF clones 1B11 and 3B3 reverse the effects of G-CSF on flt3L-induced bone marrow dendritic cell development. Mouse bone marrow was cultured with recombinant Flt3L (200 ng/mL) in the presence of various concentrations of supernatants from human G-CSF producing NOP12 tumors for 9 days in the presence or absence of anti-G-CSF clones 1B11 or 3B3 (10 µg/mL). Day 9 cell counts (A). MHC Class II and CD11c expression on the cells (B) was assessed as a measure of the frequency of mature dendritic cells (MHC Class II+CD11c+).

FIGS. 9A-B. Anti-human G-CSF clones 1B11 and 3B3 reverse the effects of G-CSF on MHC Class II expression on GM-CSF-induced bone marrow dendritic cells. Mouse bone marrow was cultured with GM-CSF (1/1000 dilution of 293T-G-CSF supernatant) in the presence of 1% (left; A) or 5% (right; B) supernatant from human G-CSF producing NOP12 tumors for 9 days in the presence or absence of anti-G-CSF clones 1B11 or 3B3 (10 µg/mL). MHC Class II expression on the cells was assessed as a measure of dendritic cell development. Histograms represent MHC Class II expression on cells grown without antibody (red), clone 1B11 (blue), or 3B3 (orange).

FIG. 10. Anti-G-CSF clones 1B11 and 3B3 block G-CSF signaling in primary human neutrophils. Various concentrations of human G-CSF (Genscript) were preincubated with 10 µg/mL of purified antibody clone 1B11, 3B3, or an isotype control. After 30 mins, the G-CSF/antibody mixture was added to a plate containing $5 \times 10^5$ purified human neutrophils per well. The plate was incubated for 20 mins after which the cells were immediately fixed and stained for intracellular phosphorylated Stat3 (P-Tyr 705) according to the manufacturers protocol (BD Biosciences). Neutrophils cultured without cytokine and without antibody served as negative and positive controls respectively. Percent maximum Stat3 phosphorylation was calculated for each sample as [MFI (mean fluorescence intensity) experimental sample]/[MFI of the positive control]×100%. This figure demonstrates that clone 3B3 and 1B11 both block early G-CSF signaling in human neutrophils and that clone 3B3 demonstrates 2-3× more neutralizing activity than 1B11. 3B3 (bottom set of circles); 1B11 (middle set of circles) and isotype control (top set of circles).

FIGS. 11A-B. Neutralization of in vivo tumor G-CSF production reduces the frequency and T cell suppressive ability of MDSCs. C57Bl/6 mice were inoculated with $1 \times 10^6$ MC38 colon carcinoma cells engineered to express human G-CSF. After 7 days, animals were treated 3 times per week with 200 µg of anti-G-CSF clone 1B11, or 3B3 or an isotype control antibody. A) On day 25 the animals were euthanized and the spleens were removed and analyzed for the presence of CD11b+Ly6G+ cells (MDSCs) by flow cytometry. B) Spleens from tumor bearing mice were used as a source of suppressor cells (MDSCs) and added at various ratios to OT-I TCR transgenic splenocytes labeled with a proliferation dye. Whole OVA (200 µg/mL) was added to the cultures as a source of antigen. The OT-I cells also expressed YFP under control of the IFN-gamma promoter which allows one to detect IFN-gamma production based on YFP expression. On day 4, the cells were stimulated with PMA (50 ng/mL) and analyzed by flow cytometry for proliferation and IFN-gamma production. OT-I splenocytes cultured with OVA alone in the absence of MDSCs and OT-I splenocytes cultured with non-tumor bearing splenocytes which lack MDSCs (no tumor group) served as positive controls. OT-I splenocytes cultured in the absence of OVA served as a negative control. The numbers in the upper left quadrant represent OT-I T cells which have undergone at least one division and are capable of producing IFN-gamma. There is clear suppression of OT-I proliferation at the 10 to 1 tumor splenocyte to OT-I splenocyte ratio. Splenocytes from 1B11 and 3B3 treated mice have a reduced ability to suppress OT-I proliferation when compared to the isotype control treated group.

FIG. 12 is a table illustrating the characteristics of 15 humanized variants of 1B11 antibody.

Figure 16B:
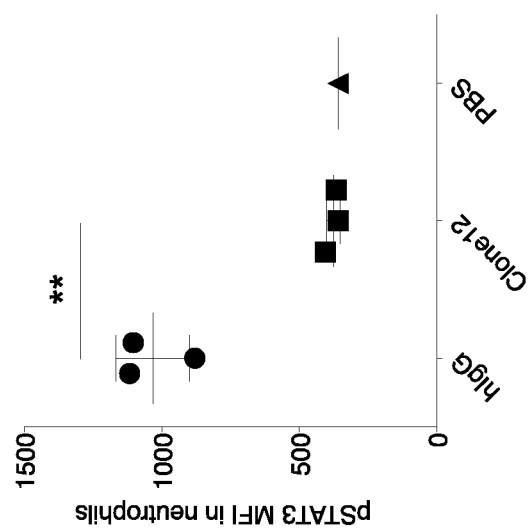
Figure 16A:
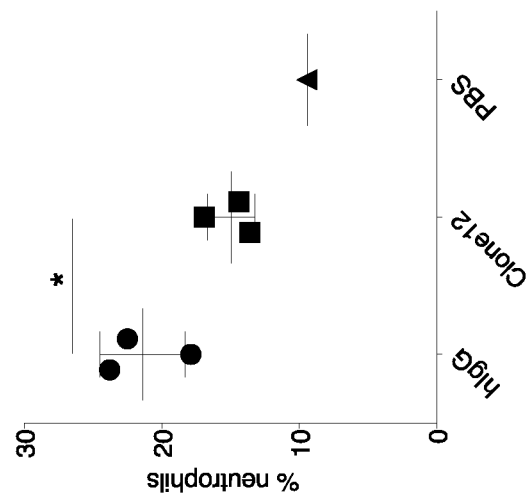

FIGS. 16A and B are graphs illustrating reduction of G-CSF induced neutrophilia and blocking of neutrophil pSTAT 3 signaling by humanized 1B11 variant 12 antibody.

DETAILED DESCRIPTION OF THE INVENTION

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Cabs, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); and The Antibodies (M. Zanetti and J. D. Capra, eds., Harwood Academic Publishers, 1995).

The term "about" includes equal to, and a range that takes into account experimental error in a given measurement and can refer to plus or minus 5, 4, 3, 2 or 1% or anywhere in-between.

As used herein, "substantially pure", "isolated" or "purified" refers to material which is at least 50% pure (i.e., free from contaminants), more preferably at least 90% pure, more preferably at least 95% pure, more preferably at least 98% pure, more preferably at least 99% pure. Antibodies can be isolated and purified from the culture supernatant or ascites mentioned above by saturated ammonium sulfate precipitation, euglobulin precipitation method, caproic acid method, caprylic acid method, ion exchange chromatography (DEAE or DE52), or affinity chromatography using anti-Ig column or a protein A, G or L column using art-recognized conventional methods.

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, .alpha.-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Complement dependent cytotoxicity" and "CDC" refer to the lysing of a target in the presence of complement. The complement activation pathway is initiated by the binding of the first component of the complement system (C1q) to a molecule (e.g., an antibody) complexed with a cognate antigen. To assess complement activation, a CDC assay, e.g., as described in Gazzano-Santoro et al., *J. Immunol. Methods*, 202:163 (1996), may be performed.

As used herein "antibody-dependent cell-mediated cytotoxicity" and "ADCC" refer to a cell-mediated reaction in which nonspecific cytotoxic cells that express Fc receptors (FcRs) (e.g., natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in an animal model such as that disclosed in Clynes et al., 1998, *PNAS USA,* 95:652-656.

The terms "apoptosis" or "programmed cell death," refers to the physiological process by which unwanted or useless cells are eliminated during development and other normal biological processes. Apoptosis is a mode of cell death that occurs under normal physiological conditions and the cell is an active participant in its own demise ("cellular suicide"). It is most often found during normal cell turnover and tissue homeostasis, embryogenesis, induction and maintenance of immune tolerance, development of the nervous system and endocrine-dependent tissue atrophy. Cells undergoing apoptosis show characteristic morphological and biochemical features. These features include chromatin aggregation, nuclear and cytoplasmic condensation, partition of cytoplasm and nucleus into membrane bound vesicles (apoptotic bodies), which contain ribosomes, morphologically intact mitochondria and nuclear material. In vivo, these apoptotic bodies are rapidly recognized and phagocytized by macrophages, dendritic cells or adjacent epithelial cells. Due to this efficient mechanism for the removal of apoptotic cells in vivo no inflammatory response is elicited. In vitro, the apoptotic bodies as well as the remaining cell fragments ultimately swell and finally lyse. This terminal phase of in vitro cell death has been termed "secondary necrosis." Apoptosis can be measured by methods known to those skilled in the art like DNA fragmentation, exposure of Annexin V, activation of caspases, release of cytochrome c, etc. A cell that has been induced to die is termed herein as an "apoptotic cell."

Apoptosis can be tested using a standard Annexin V Apoptosis Assay: NIH:OVCAR-3 cells are grown in 6-well plates (NUNC) and irradiated or treated with an antagonist (or in combination with another anti-cancer drug) for 4-48 hours, washed and stained with Annexin V-FITC (BD-Pharmingen) for 1 hour. Cells are analyzed by flow cytometry (Becton-Dickinson, CellQuest), counterstained with Propidium Iodide and analyzed again in the flow cytometer.

As used herein, the term "granulocyte colony stimulating factor" and "G-CSF" refers to a glycoprotein that is mainly produced by fibroblasts and endothelial cells from bone marrow stroma and by immunocompetent cells (monocytes, macrophages). The receptor for G-CSF (G-CSFR) is part of the cytokine and hematopoietin receptor superfamily. As used herein, G-CSF includes all mammalian species of native sequence G-CSF, e.g., human, canine, feline, equine, bovine, etc.

Antibodies

As used herein, an "anti-G-CSF antibody" refers to an antibody that is able to bind to G-CSF and inhibit G-CSF biological activity and/or downstream pathway(s) mediated by G-CSF signaling. An anti-G-CSF antibody encompasses antibodies that block, antagonize, suppress or reduce (including significantly) G-CSF biological activity, including downstream pathways mediated by G-CSF signaling. For purpose of the present application, it will be explicitly understood that the term "anti-G-CSF antibody" encompasses all the previously identified terms, titles, and functional states and characteristics whereby the G-CSF itself, an G-CSF biological activity (including, but not limited to, its ability to treat a cancer), or the consequences of the biological activity, are substantially nullified, decreased, or neutralized in any meaningful degree. In one embodiment, an anti-G-CSF antibody binds G-CSF and neutralizes its activity.

Provided herein is an isolated or a purified antibody, or antigen-binding fragment thereof, that binds to granulocyte colony stimulating factor (G-CSF), that comprises a heavy chain CDR1 referenced as SEQ ID NO: 1 or SEQ ID NO: 1 having a conservative substitution therein; a heavy chain CDR2 referenced as SEQ ID NO: 2 or SEQ ID NO: 2 having a conservative substitution therein; a heavy chain CDR3 referenced as SEQ ID NO: 3 or SEQ ID NO: 3 having a conservative substitution therein; a light chain CDR1 referenced as SEQ ID NO: 4 or SEQ ID NO: 4 having a conservative substitution therein; a light chain CDR2 referenced as SEQ ID NO: 5 or SEQ ID NO: 5 having a conservative substitution therein; and a light chain CDR3 referenced as SEQ ID NO: 6 or SEQ ID NO: 6 having a conservative substitution therein. In one instance, the isolated or purified antibody, or antigen-binding fragment thereof, comprises a heavy chain variable region referenced as SEQ ID NO: 7 and a light chain variable region referenced as SEQ ID NO: 8. In another instance, such an antibody is referred to as 1B11.

Also provided herein is an isolated or purified antibody, or antigen-binding fragment thereof, that binds to granulocyte colony stimulating factor (G-CSF), that comprises a heavy chain CDR1 referenced as SEQ ID NO: 9 or SEQ ID NO: 9 having a conservative substitution therein; a heavy chain CDR2 referenced as SEQ ID NO: 10 or SEQ ID NO: 10 having a conservative substitution therein; a heavy chain CDR3 referenced as SEQ ID NO: 11 or SEQ ID NO: 11 having a conservative substitution therein; a light chain CDR1 referenced as SEQ ID NO: 12 or SEQ ID NO: 12 having a conservative substitution therein; a light chain CDR2 referenced as SEQ ID NO: 13 or SEQ ID NO: 13 having a conservative substitution therein; and a light chain CDR3 referenced as SEQ ID NO: 14 or SEQ ID NO: 14 having a conservative substitution therein. In one instance, the isolated or purified antibody, or antigen-binding fragment thereof, comprises a heavy chain variable region referenced as SEQ ID NO: 15 and a light chain variable region referenced as SEQ ID NO: 16. In another instance, such an antibody is referred to as 3B3.

It would be understood that the antibodies described herein can be modified as described below or as known in the art.

"Antibodies" useful in the present invention encompass, but are not limited to, monoclonal antibodies, polyclonal antibodies, antibody fragments (e.g., Fab, Fab', F(ab')$_2$, Fv, Fc, etc.), chimeric antibodies, bispecific antibodies, multispecific antibodies, heteroconjugate antibodies, single chain (ScFv), mutants thereof, fusion proteins comprising an antibody portion (e.g., a domain antibody), humanized antibodies, human antibodies, single domain antibodies, and any other modified configuration of the immunoglobulin molecule that comprises an antigen recognition site of the required specificity, including glycosylation variants of antibodies, amino acid sequence variants of antibodies, and covalently modified antibodies. The term "chimeric" refers to an antibody in which a portion of the heavy and/or light chain is derived from a particular source or species, while the remainder of the heavy and/or light chain is derived from a different source or species.

Depending on the amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The subunit structures and three-dimensional configurations of different classes of immunoglobulins are well known in the art.

The "light chains" of antibodies (immunoglobulins) from any vertebrate species can be assigned to one of two clearly distinct types, called kappa or ("κ" or "K") and lambda or ("λ"), based on the amino acid sequences of their constant domains.

As used herein, a "monoclonal antibody" refers to an antibody obtained from a population of substantially homogeneous antibodies, i.e., the individual antibodies comprising the population are identical except for possible naturally-occurring mutations that may be present in minor amounts. In contrast to polyclonal antibody preparations, which typically include different antibodies directed against different determinants (epitopes), each monoclonal antibody is directed against a single determinant on the antigen (epitope). The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, *Nature,* 256:495, or may be made by recombinant DNA methods such as described in U.S. Pat. No. 4,816,567. The monoclonal antibodies may also be isolated from phage libraries generated using the techniques described in McCafferty et al., 1990, *Nature,* 348:552-554, for example. Other methods are known in the art and are contemplated for use herein.

As used herein, "humanized" antibodies refer to forms of non-human (e.g., murine) antibodies that are specific chimeric immunoglobulins, immunoglobulin chains, or fragments thereof (such as Fv, Fab, Fab', F(ab')$_2$, scFv, or other antigen-binding subsequences of antibodies) that contain minimal sequence derived from non-human immunoglobulin. For the most part, humanized antibodies are human immunoglobulins (recipient antibody) in which residues from a complementarity determining region (CDR) of the recipient are replaced by residues from a CDR of a non-human species (donor antibody) such as mouse, rat, or rabbit having the desired specificity, affinity, and biological activity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, a humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in, for example, WO 99/58572. Other forms of humanized antibodies have one or more CDRs (one, two, three, four, five or six) which are altered with respect to the original antibody, which are also termed one or more CDRs "derived from" one or more CDRs from the original antibody.

As used herein, a "human antibody" means an antibody having an amino acid sequence corresponding to that of an antibody produced by a human and/or has been made using any of the techniques for making human antibodies known in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., 1996, *Nature Biotechnology,* 14:309-314; Sheets et al., 1998, *PNAS USA,* 95:6157-6162; Hoogenboom and Winter, 1991, *J. Mol. Biol.,* 227:381; Marks et al., 1991, *J. Mol. Biol.,* 222:581). Human antibodies can also be made by introducing human immunoglobulin loci into transgenic animals, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or may have been immunized in vitro). See, e.g., Cole et al., Monoclonal Antibodies and Cancer Therapy, Alan R. Liss, p. 77 (1985); Boerner et al., 1991, *J. Immunol.,* 147 (1):86-95; and U.S. Pat. No. 5,750,373.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al., Sequences of Proteins of Immunological Interest, (5th ed., 1991, National Institutes of Health, Bethesda Md.)); and (2) an approach based on crystallographic studies of antigen-antibody complexes (Al-lazikani et al. (1997) *J. Molec. Biol.* 273:927-948)). As used herein, a CDR may refer to CDRs defined by either approach or by a combination of both approaches.

A "constant region" of an antibody refers to the constant region of the antibody light chain or the constant region of the antibody heavy chain, either alone or in combination.

"Epitope" refers to that portion of an antigen or other macromolecule capable of forming a binding interaction with the variable region binding pocket of an antibody. Such binding interactions can be manifested as an intermolecular contact with one or more amino acid residues of one or more CDRs. Antigen binding can involve, for example, a CDR3 or a CDR3 pair or, in some cases, interactions of up to all six CDRs of the $V_H$ and $V_L$ chains. An epitope can be a linear peptide sequence (i.e., "continuous") or can be composed of noncontiguous amino acid sequences (i.e., "conformational" or "discontinuous"). An antibody can recognize one or more amino acid sequences; therefore an epitope can define more than one distinct amino acid sequence. Epitopes recognized by antibodies can be determined by peptide mapping and sequence analysis techniques well known to one of skill in the art. Binding interactions are manifested as intermolecular contacts between an epitope on an antigen and one or more amino acid residues of a CDR.

An epitope that "preferentially binds" or "specifically binds" (used interchangeably herein) to an antibody or a polypeptide is a term well understood in the art, and methods to determine such specific or preferential binding are also well known in the art. An antibody specifically binds or preferentially binds to a target if it binds with greater affinity, avidity, more readily, and/or with greater duration than it binds to other substances. For example, an antibody that specifically or preferentially binds to a G-CSF epitope is an antibody that binds this epitope with greater affinity, avidity, more readily, and/or with greater duration than it binds to other G-CSF epitopes or non-G-CSF epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding where the affinity of the antibody, or antigen-binding fragment thereof, is at least at least 2-fold greater, at least 3-fold greater, at least 4-fold greater, at least 5-fold greater, at least 6-fold greater, at least 7-fold greater, at least 8-fold greater, at least 9-fold greater, 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater than the affinity of the antibody for unrelated amino acid sequences.

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat et al., (Sequences of Proteins of Immunological Interest, 5th Ed. Public Health Service, National Institutes of Health, Bethesda, Md., 1991). The Fc region of an immunoglobulin generally comprises two constant domains, CH2 and CH3.

As used herein, "Fc receptor" and "FcR" describe a receptor that binds to the Fc region of an antibody.

A "functional Fc region" possesses at least one effector function of a native sequence Fc region. Exemplary "effector functions" include C1q binding; complement dependent cytotoxicity (CDC); Fc receptor binding; antibody-dependent cell-mediated cytotoxicity (ADCC); phagocytosis; down-regulation of cell surface receptors (e.g., B cell receptor; BCR), etc. Such effector functions generally require the Fc region to be combined with a binding domain (e.g., an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95%, at least about 96%, at least about 97%, at least about 98%, at least about 99% sequence identity therewith.

The terms "hypervariable region" and "CDR" when used herein, refer to the amino acid residues of an antibody which are responsible for antigen-binding. The CDRs comprise amino acid residues from three sequence regions which bind in a complementary manner to an antigen and are known as CDR1, CDR2, and CDR3 for each of the $V_H$ and $V_L$ chains. In the light chain variable domain, the CDRs typically correspond to approximately residues 24-34 (CDRL1), 50-56 (CDRL2) and 89-97 (CDRL3), and in the heavy chain variable domain the CDRs typically correspond to approximately residues 31-35 (CDRH1), 50-65 (CDRH2) and 95-102 (CDRH3) according to Kabat et al. (Id.). It is understood that the CDRs of different antibodies may contain insertions, thus the amino acid numbering may differ. The Kabat numbering system accounts for such insertions with a numbering scheme that utilizes letters attached to specific residues (e.g., 27A, 27B, 27C, 27D, 27E, and 27F of CDRL1 in the light chain) to reflect any insertions in the numberings between different antibodies. Alternatively, in the light chain variable domain, the CDRs typically correspond to approximately residues 26-32 (CDRL1), 50-52 (CDRL2) and 91-96 (CDRL3), and in the heavy chain variable domain, the CDRs typically correspond to approximately residues 26-32 (CDRH1), 53-55 (CDRH2) and 96-101 (CDRH3) according to Chothia and Lesk, *J. Mol. Biol.*, 196: 901-917 (1987)).

As used herein, "framework region" or "FR" refers to framework amino acid residues that form a part of the antigen binding pocket or groove. In some embodiments, the framework residues form a loop that is a part of the antigen binding pocket or groove and the amino acids residues in the loop may or may not contact the antigen. Framework regions generally comprise the regions between the CDRs. In the light chain variable domain, the FRs typically correspond to approximately residues 0-23 (FRL1), 35-49 (FRL2), 57-88 (FRL3), and 98-109 and in the heavy chain variable domain the FRs typically correspond to approximately residues 0-30 (FRH1), 36-49 (FRH2), 66-94 (FRH3), and 103-133 according to Kabat et al. (Id.). As discussed above with the Kabat numbering for the light chain, the heavy chain too accounts for insertions in a similar manner (e.g., 35A, 35B of CDRH1 in the heavy chain). Alternatively, in the light chain variable domain, the FRs typically correspond to approximately residues 0-25 (FRL1), 33-49 (FRL2) 53-90 (FRL3), and 97-109 (FRL4), and in the heavy chain variable domain, the FRs typically correspond to approximately residues 0-25 (FRH1), 33-52 (FRH2), 56-95 (FRH3), and 102-113 (FRH4) according to Chothia and Lesk Mol. Biol., 196: 901-917 (1987)).

The loop amino acids of a FR can be assessed and determined by inspection of the three-dimensional structure of an antibody heavy chain and/or antibody light chain. The three-dimensional structure can be analyzed for solvent accessible amino acid positions as such positions are likely to form a loop and/or provide antigen contact in an antibody variable domain. Some of the solvent accessible positions can tolerate amino acid sequence diversity and others (e.g., structural positions) are, generally, less diversified. The three dimensional structure of the antibody variable domain can be derived from a crystal structure or protein modeling.

The term "$k_{on}$", as used herein, is intended to refer to the rate constant for association of an antibody to an antigen.

The term "$K_{off}$", as used herein, is intended to refer to the rate constant for dissociation of an antibody from the antibody/antigen complex.

As used herein, the term "affinity" refers to the equilibrium constant for the reversible binding of two agents and is expressed as $K_D$. The binding affinity ($K_D$) of an antibody described herein can be about 0.02 pM to about 250 nM, or any integer therebetween. In some embodiments, the binding affinity is any of about 250 nM, about 225 nM, about 200 nM, about 175 nM, about 150 nM, about 125 nM, 100 nM, about 75 nM, about 50 nM, about 25 nM, about 10 nM, about 5 nM, about 4 nM, about 3 nM, about 2.5 nM, about 2 nM, about 1.5 nM, about 1 nM, about 1 nM, about 750 pM, about 500 pM, about 275 pM, about 250 pM, about 225 pM, about 100 pM, about 75 pM, about 60 pM, about 50 pM, about 25 pM, about 20 pM, about 15 pM, about 10 pM, about 5 pM, about 2 pM, about 1 pM, about 0.5 pM, about 0.1 pM, about 0.05 pM, or about 0.02 pM, about 1 femtomolar (fM), or any integer therebetween.

Binding affinity may be determined using surface plasmon resonance (SPR), Kinexa Biocensor, scintillation proximity assays, enzyme linked immunosorbent assay (ELISA), ORIGEN immunoassay (IGEN), fluorescence quenching, fluorescence transfer, yeast display, or any combination thereof. Binding affinity may also be screened using a suitable bioassay.

As used herein, the term "avidity" refers to the resistance of a complex of two or more agents to dissociation after dilution. Apparent affinities can be determined by methods such as an enzyme linked immunosorbent assay (ELISA) or any other technique familiar to one of skill in the art. Avidities can be determined by methods such as a Scatchard analysis or any other technique familiar to one of skill in the art.

An antibody, or antigen-binding fragment thereof, can be modified by making one or more substitutions in the amino acid sequence using a conservative or a non-conservative substitution.

The phrase "conservative amino acid substitution" refers to grouping of amino acids on the basis of certain common properties. A functional way to define common properties between individual amino acids is to analyze the normalized frequencies of amino acid changes between corresponding proteins of homologous organisms (Schulz, G. E. and R. H. Schirmer, Principles of Protein Structure, Springer-Verlag). According to such analyses, groups of amino acids may be defined where amino acids within a group exchange preferentially with each other, and therefore resemble each other most in their impact on the overall protein structure. Examples of amino acid groups defined in this manner include:

(i) a charged group, consisting of Glu and Asp, Lys, Arg and His;
(ii) a positively-charged group, consisting of Lys, Arg and His;
(iii) a negatively-charged group, consisting of Glu and Asp;
(iv) an aromatic group, consisting of Phe, Tyr and Trp;
(v) a nitrogen ring group, consisting of His and Trp;
(vi) a large aliphatic non-polar group, consisting of Val, Leu and Ile;
(vii) a slightly-polar group, consisting of Met and Cys;
(viii) a small-residue group, consisting of Ser, Thr, Asp, Asn, Gly, Ala, Glu, Gln and Pro;
(ix) an aliphatic group consisting of Val, Leu, Ile, Met and Cys; and
(x) a small hydroxyl group consisting of Ser and Thr.

In addition to the groups presented above, each amino acid residue may form its own group, and the group formed by an individual amino acid may be referred to simply by the one and/or three letter abbreviation for that amino acid commonly used in the art as described above.

A "conserved residue" is an amino acid that is relatively invariant across a range of similar proteins. Often conserved residues will vary only by being replaced with a similar amino acid, as described above for "conservative amino acid substitution."

The letter "x" or "xaa" as used in amino acid sequences herein is intended to indicate that any of the twenty standard amino acids may be placed at this position unless specifically noted otherwise. For the purposes of peptidomimetic design, an "x" or a "xaa" in an amino acid sequence may be replaced by a mimic of the amino acid present in the target sequence, or the amino acid may be replaced by a spacer of essentially any form that does not interfere with the activity of the peptidomimetic.

"Homology" or "identity" or "similarity" refers to sequence similarity between two peptides or between two nucleic acid molecules. Homology and identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. A sequence which is "unrelated" or "non-homologous" shares less than 40% identity, though preferably less than 25% identity with a sequence of the present invention. In comparing two sequences, the absence of residues (amino acids or nucleic acids) or presence of extra residues also decreases the identity and homology/similarity.

The term "homology" describes a mathematically based comparison of sequence similarities which is used to identify genes or proteins with similar functions or motifs. The nucleic acid (nucleotide, oligonucleotide) and amino acid (protein) sequences of the present invention may be used as a "query sequence" to perform a search against public databases to, for example, identify other family members, related sequences or homologs. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to nucleic acid molecules of the invention. BLAST amino acid searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and BLAST) can be used (see, www.ncbi.nlm.nih.gov).

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. *Applied Math.,* 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., *Nucleic Acids Research* 12(1): 387 (1984)), BLASTP, BLASTN, and FASTA (Altschul, S. F. et al., *J. Molec. Biol.* 215: 403-410 (1990) and Altschul et al. *Nuc. Acids Res.* 25: 3389-3402 (1997)). The BLAST X program is publicly available from NCBI and other sources (BLAST Manual, Altschul, S., et al., NCBI NLM NIH Bethesda, Md. 20894;

Altschul, S., et al., *J. Mol. Biol.* 215: 403-410 (1990). The well-known Smith Waterman algorithm may also be used to determine identity.

If needed, an antibody or an antigen binding fragment thereof described herein can be assessed for immunogenicity and, as needed, be deimmunized (i.e., the antibody is made less immunoreactive by altering one or more T cell epitopes of an antibody). Analysis of immunogenicity and T-cell epitopes present in the antibodies and antigen-binding fragments described herein can be carried out via the use of software and specific databases. Exemplary software and databases include iTope™ developed by Antitope of Cambridge, England. iTope™, which is an in silico technology for analysis of peptide binding to human MHC class II alleles.

The iTope™ software predicts peptide binding to human MHC class II alleles and thereby provides an initial screen for the location of such "potential T cell epitopes." iTope™ software predicts favorable interactions between amino acid side chains of a peptide and specific binding pockets within the binding grooves of 34 human MHC class II alleles. The location of key binding residues is achieved by the in silico generation of 9mer peptides that overlap by one amino acid spanning the test antibody variable region sequence. Each 9mer peptide can be tested against each of the 34 MHC class II allotypes and scored based on their potential "fit" and interactions with the MHC class II binding groove. Peptides that produce a high mean binding score (>0.55 in the iTope™ scoring function) against >50% of the MHC class II alleles are considered as potential T cell epitopes. In such regions, the core 9 amino acid sequence for peptide binding within the MHC class II groove is analyzed to determine the MHC class II pocket residues (P1, P4, P6, P7 and P9) and the possible T cell receptor (TCR) contact residues (P-1, P2, P3, P5, P8).

After identification of any T-cell epitopes, amino acid residue changes, substitutions, additions, and/or deletions can be introduced to remove the identified T-cell epitope. Such changes can be made so as to preserve antibody structure and function while still removing the identified epitope. Exemplary changes can include, but are not limited to, conservative amino acid changes.

Provided herein are neutralizing antibodies or antigen-binding fragments that bind to G-CSF and inhibit the activity of G-CSF.

Percentage (%) of inhibition/neutralization by an anti-G-CSF antibody or antigen-binding fragment thereof of at least 2-fold, at least 3-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, at least 60-fold, or greater than negative controls is indicative of a antibody or antigen-binding fragment thereof inhibits or neutralizes G-CSF. Percentage of inhibition of G-CSF by an anti-G-CSF antibody or antigen-binding fragment thereof of less than 2-fold greater than negative controls is indicative of an antibody or antigen-binding fragment thereof that does not inhibit G-CSF.

Antibodies, or antigen-binding fragments thereof, described herein can also be used as immunoconjugates. As used herein, for purposes of the specification and claims, immunoconjugates refer to conjugates comprised of the anti-G-CSF antibodies or fragments thereof according to the present invention and at least one therapeutic label. Therapeutic labels include antitumor agents and angiogenesis-inhibitors. Such antitumor agents are known in the art and include, but are not limited to, toxins, drugs, enzymes, cytokines, radionuclides, and photodynamic agents. Toxins include, but are not limited to, ricin A chain, mutant *Pseudomonas* exotoxins, diphtheria toxoid, streptonigrin, boamycin, saporin, gelonin, and pokeweed antiviral protein. Drugs include, but are not limited to, daunorubicin, methotrexate, and calicheamicin. Radionuclides include radiometals. Cytokines include, but are not limited to, transforming growth factor beta (TGF-β), interleukins, interferons, and tumor necrosis factors; examples of each of these cytokines and their functions are well known in the art. Photodynamic agents include, but are not limited to, porphyrins and their derivatives. Additional therapeutic labels will be known in the art and are also contemplated herein. The methods for complexing the anti-G-CSF mAbs or antigen-binding fragments thereof with at least one agent are well known to those skilled in the art (i.e., antibody conjugates as reviewed by Ghetie et al., 1994, *Pharmacol. Ther.* 63:209-34). Such methods may utilize one of several available heterobifunctional reagents used for coupling or linking molecules. Linkers for conjugating antibodies to other moieties are well known in the art and are contemplated herein.

Methods for conjugating or linking polypeptides are well known in the art. Associations (binding) between antibodies and labels include any means known in the art including, but not limited to, covalent and non-covalent interactions, chemical conjugation as well as recombinant techniques.

Antibodies, or antigen-binding fragments thereof, can be modified using techniques known in the art for various purposes such as, for example, by addition of polyethylene glycol (PEG). PEG modification (PEGylation) can lead to one or more of improved circulation time, improved solubility, improved resistance to proteolysis, reduced antigenicity and immunogenicity, improved bioavailability, reduced toxicity, improved stability, and easier formulation (for a review, see, Francis et al., *International Journal of Hematology* 68:1-18, 1998).

Other methods of improving the half-life of antibody-based fusion proteins in circulation are also known such as, for example, described in U.S. Pat. Nos. 7,091,321 and 6,737,056, each of which is hereby incorporated by reference. Additionally, antibodies and antigen-binding fragments thereof may be produced or expressed so that they do not contain fucose on their complex N-glycoside-linked sugar chains. The removal of the fucose from the complex N-glycoside-linked sugar chains is known to increase effector functions of the antibodies and antigen-binding fragments, including but not limited to, antibody dependent cell-mediated cytotoxicity (ADCC) and complement dependent cytotoxicity (CDC). Similarly, antibodies or antigen-binding fragments thereof that can bind G-CSF can be attached at their C-terminal end to all or part of an immunoglobulin heavy chain derived from any antibody isotype, e.g., IgG, IgA, IgE, IgD and IgM and any of the isotype sub-classes, particularly IgG1, IgG2b, IgG2a, IgG3 and IgG4.

Antibodies, or antigen-binding fragments thereof, that bind to G-CSF can also be used for purification of G-CSF and/or to detect G-CSF levels in a sample or subject. Compositions of antibodies and antigen-binding fragments described herein can be used as non-therapeutic agents (e.g., as affinity purification agents). Generally, in one such embodiment, a protein of interest is immobilized on a solid phase such a Sephadex resin or filter paper, using conventional methods known in the art. The immobilized protein is contacted with a sample containing the target of interest (or fragment thereof) to be purified, and thereafter the support is washed with a suitable solvent that will remove substantially all the material in the sample except the target protein, which is bound to the immobilized antibody. Finally, the support is washed with another suitable solvent, such as glycine buffer, pH 5.0, which will release the target protein.

An antibody or antigen-binding fragment thereof can be conjugated to, or recombinantly engineered with, an affinity tag (e.g., a purification tag). Affinity tags such as, for example, His6 tags (His-His-His-His-His-His; SEQ ID NO: 21) are conventional in the art.

Methods of Making Antibodies

The antibodies described herein may be made by any method known in the art. The route and schedule of immunization of the host animal are generally in keeping with established and conventional techniques for antibody stimulation and production, as further described herein. General techniques for production of human and mouse antibodies are known in the art and are described herein and below in the Examples.

It is contemplated that any mammalian subject including humans or antibody producing cells therefrom can be manipulated to serve as the basis for production of mammalian, including human, hybridoma cell lines. Typically, the host animal is inoculated intraperitoneally, intramuscularly, orally, subcutaneously, intraplantar, and/or intradermally with an amount of immunogen, including as described herein.

Immunization of a host animal with a human protein, or a fragment containing a target amino acid sequence conjugated to an adjuvant that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaradehyde, succinic anhydride, $SOCl_2$, or any other adjuvant known in the art, can yield a population of antibodies.

Hybridomas can be prepared from the lymphocytes of immunized animals and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce monoclonal antibodies. The hybridomas are expanded and subcloned, if desired, and supernatants are assayed for anti-immunogen activity by conventional immunoassay procedures (e.g., radioimmunoassay, enzyme immunoassay, fluorescence immunoassay, etc.).

Hybridomas that may be used as source of antibodies encompass all derivatives, progeny cells of the parent hybridomas that produce monoclonal antibodies, or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired.

Undesired activity, if present, can be removed, for example, by running the preparation over adsorbents made of the immunogen attached to a solid phase and eluting or releasing the desired antibodies off the immunogen.

Antibodies may be made recombinantly and expressed using any method known in the art.

Antibodies may be made recombinantly by phage display technology. See, for example, U.S. Pat. Nos. 5,565,332; 5,580,717; 5,733,743; and 6,265,150; and Winter et al., Annu. Rev. Immunol. 12:433-455 (1994). Alternatively, the phage display technology (McCafferty et al., Nature 348: 552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S, and Chiswell, David J., Current Opinion in Structural Biology, 3:564-571 (1993). Several sources of V-gene segments can be used for phage display. Clackson et al., Nature 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., J. Mol. Biol. 222:581-597 (1991), or Griffith et al., EMBO J. 12:725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." Marks, et al., Bio/Technol. 10:779-783 (1992)). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., Nucl. Acids Res. 21:2265-2266 (1993). Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody is obtained (see PCT Publication No. WO 93/06213, published Apr. 1, 1993). Unlike traditional humanization of rodent antibodies by CDR grafting, this technique provides completely human antibodies, which have no framework or CDR residues of rodent origin.

There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; and 6,180,370.

A number of "humanized" antibody molecules comprising an antigen-binding site derived from a non-human immunoglobulin have been described, including chimeric antibodies having rodent or modified rodent V regions and their associated complementary determining regions (CDRs) fused to human constant domains. See, for example, Winter et al. Nature 349:293-299 (1991), Lobuglio et al. Proc. Nat. Acad. Sci. USA 86:4220-4224 (1989), Shaw et al. J. Immunol. 138:4534-4538 (1987), and Brown et al. Cancer Res. 47:3577-3583 (1987).

Other references describe rodent CDRs grafted into a human supporting framework region (FR) prior to fusion with an appropriate human antibody constant domain. See, for example, Riechmann et al. Nature 332:323-327 (1988), Verhoeyen et al., Science, 239:1534-1536 (1988), and Jones et al., Nature, 321:522-525 (1986). Another reference describes rodent CDRs supported by recombinantly veneered rodent framework regions. See, for example, European Patent Publication No. 0519596. These "humanized" molecules are designed to minimize unwanted immunological response toward rodent anti-human antibody molecules which limits the duration and effectiveness of therapeutic applications of those moieties in human recipients. For example, the antibody constant region can be engineered such that it is immunologically inert (e.g., does not trigger complement lysis). See, e.g., PCT Publication No. WO 99/058572; and UK Patent Application No. 9809951.8.

Other methods of humanizing antibodies that may also be utilized are disclosed by Daugherty et al., Nucl. Acids Res., 19:2471-2476 (1991) and in U.S. Pat. Nos. 6,180,377; 6,054,297; 5,997,867; 5,866,692; 6,210,671; and 6,350,861; and in PCT Publication No. WO 01/27160.

In yet another alternative, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are XENOMOUSE™ from Abgenix, Inc. (Fremont, Calif.) and HUMAB-MOUSE® and TC MOUSE™ from Medarex, Inc. (Princeton, N.J.).

It will be apparent that although the above discussion pertains to humanized antibodies, the general principles discussed are applicable to customizing antibodies for use, for example, in dogs, cats, primate, equines and bovines. It is further apparent that one or more aspects of humanizing an antibody described herein may be combined, e.g., CDR grafting, framework mutation and CDR mutation.

If desired, an antibody of interest may be sequenced using any known method and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity, or other characteristics of the antibody. For example, the constant region may be engineered to more resemble human constant regions to avoid immune response if the antibody is used in clinical trials and treatments in humans.

Also provided herein are methods of making any of these antibodies or polypeptides. The antibodies of this invention can be made using any conventional procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody could be produced by an automated polypeptide synthesizer employing the solid phase method. See also, U.S. Pat. Nos. 5,807,715; 4,816,567; and 6,331,415.

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. Vaccine 19:2756 (2001); Lonberg, N. and D. Huszar Int. Rev. Immunol 13:65 (1995); and Pollock, et al., J Immunol Methods 231:147 (1999). Methods for making derivatives of antibodies, e.g., single chain, etc. are known in the art.

As used herein, "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected with a polynucleotide(s) of this invention.

DNA encoding an antibody may be readily isolated and sequenced using conventional procedures (e.g., by using oligonucleotide probes that are capable of binding specifically to genes encoding the heavy and light chains of the monoclonal antibodies). Hybridoma cells may serve as a preferred source of such DNA. Once isolated, the DNA may be placed into expression vectors (such as expression vectors disclosed in PCT Publication No. WO 87/04462), which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA also may be modified, for example, by substituting the coding sequence for human heavy and light chain constant domains in place of the homologous murine sequences, Morrison et al., Proc. Nat.

*Acad. Sci.* 81:6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an antibody described herein.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

In some instances, it may be desirable to genetically manipulate an antibody sequence to obtain greater affinity to G-CSF and greater efficacy in inhibiting and/or neutralizing G-CSF. It will be apparent to one of skill in the art that one or more polynucleotide changes can be made to the antibody and still maintain its binding ability to G-CSF.

An expression vector can be used to direct expression of an antibody. One skilled in the art is familiar with administration of expression vectors to obtain expression of an exogenous protein in vivo. See, e.g., U.S. Pat. Nos. 6,436,908; 6,413,942; and 6,376,471.

Single chain variable region fragments ("scFv") of antibodies are described herein. Single chain variable region fragments may be made by linking light and/or heavy chain variable regions by using a short linking peptide. Bird et al. (1988) *Science* 242:423-426. An example of a linking peptide is (GGGGS)3 (SEQ ID NO: 22) which bridges approximately 3.5 nm between the carboxy terminus of one variable region and the amino terminus of the other variable region. Linkers of other sequences have been designed and used. Bird et al. (Id). Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

Other forms of single chain antibodies, such as diabodies and single domain antibodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger, P., et al., *Proc. Natl. Acad. Sci. USA,* 90:6444-6448 (1993); and Poljak, R. J., et al., *Structure,* 2:1121-1123 (1994)).

For example, bispecific antibodies, monoclonal antibodies that have binding specificities for at least two different antigens, can be prepared using the antibodies disclosed herein. Methods for making bispecific antibodies are known in the art (see, e.g., Suresh et al., 1986, *Methods in Enzymology* 121:210). Traditionally, the recombinant production of bispecific antibodies was based on the coexpression of two immunoglobulin heavy chain-light chain pairs, with the two heavy chains having different specificities (Millstein and Cuello, 1983, *Nature,* 305, 537-539). Bispecific antibodies can be composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690.

According to one approach to making bispecific antibodies, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

Heteroconjugate antibodies, comprising two covalently joined antibodies, are also within the scope of the invention. Such antibodies have been used to target immune system cells to unwanted cells (U.S. Pat. No. 4,676,980). Heteroconjugate antibodies may be made using any convenient cross-linking methods. Suitable cross-linking agents and techniques are well known in the art, and are described in U.S. Pat. No. 4,676,980.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

Anti-G-CSF antibodies, and antigen-binding fragments thereof, can be identified or characterized using methods known in the art, whereby reduction, amelioration, or neutralization of a G-CSF biological activity is detected and/or measured.

Antibodies may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an anti-G-CSF antibody binds. Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with an anti-G-CSF antibody. In another example, the epitope to which the anti-G-CSF antibody binds can be determined in a systematic screening by using overlapping peptides derived from the anti-G-CSF sequence and determining binding by the anti-G-CSF antibody. According to the gene fragment expression assays, the open reading frame encoding G-CSF is fragmented either randomly or by specific genetic constructions and the reactivity of the expressed fragments of G-CSF with the antibody to be tested is determined. The gene fragments may, for example, be produced by PCR and then transcribed and translated into protein in vitro, in the presence of radioactive amino acids. The binding of the antibody to the radioactively labeled G-CSF fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant G-CSF in which various fragments of the G-CSF polypeptide have been replaced (swapped) with sequences from a closely related, but antigenically distinct protein. By assessing binding of the antibody to the mutant G-CSF, the importance of the particular G-CSF fragment to antibody binding can be assessed.

Yet another method which can be used to characterize an anti-G-CSF antibody is to use competition assays with other antibodies known to bind to the same antigen, i.e., various fragments on G-CSF, to determine if the anti-G-CSF antibody binds to the same epitope as other antibodies. Competition assays are well known to those of skill in the art.

Also provided herein are affinity matured antibodies. For example, affinity matured antibodies can be produced by procedures known in the art (Marks et al., 1992, *Bio/Technology*, 10:779-783; Barbas et al., 1994, *Proc Nat. Acad. Sci, USA* 91:3809-3813; Schier et al., 1995, *Gene*, 169:147-155; Yelton et al., 1995, *J Immunol.*, 155:1994-2004; Jackson et al., 1995, *J Immunol.*, 154(7):3310-9; Hawkins et al, 1992, *J Mol. Biol.*, 226:889-896; and WO2004/058184).

In some embodiments, the anti-G-CSF antibodies are engineered antibodies. For example, sweeping antibodies, which may have increased binding to cell surface neonatal Fc receptor at neural pH to increase clearance of the bound antigen with the antibody from circulation in a subject, can be produced by procedures known in the art (Higuchi et al., 2013: 8(5), e63236). Bispecific/biparatopic antibodies, which forms large immune complexes that binds to Fcγ receptors and allows for clearance of the bound-antigen from circulation in a subject, can be produced by procedures known in the art (Kasturirangan et al., 2017, *J. Biol. Chem.*, 10: 4361-4370).

The following methods may be used for adjusting the affinity of an antibody and for characterizing a CDR. One way of characterizing a CDR of an antibody and/or altering (such as improving) the binding affinity of a polypeptide, such as an antibody, termed "library scanning mutagenesis". Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased or no binding are identified. Methods for determining binding affinity are well-known in the art. Binding affinity may be determined using Biacore surface plasmon resonance analysis, which detects differences in binding affinity of about 2-fold or greater. Biacore is particularly useful when the starting antibody already binds with a relatively high affinity, for example a $K_D$ of about 10 nM or lower.

In some embodiments, every amino acid position in a CDR is replaced (in some embodiments, one at a time) with all 20 natural amino acids using art recognized mutagenesis methods (some of which are described herein). This generates small libraries of clones (in some embodiments, one for every amino acid position that is analyzed), each with a complexity of 20 members (if all 20 amino acids are substituted at every position).

In some embodiments, the library to be screened comprises substitutions in two or more positions, which may be in the same CDR or in two or more CDRs. Thus, the library may comprise substitutions in two or more positions in one CDR. The library may comprise substitution in two or more positions in two or more CDRs. The library may comprise substitution in 3, 4, 5, or more positions, said positions found in two, three, four, five or six CDRs. The substitution may be prepared using low redundancy codons. See, e.g., Table 2 of Balint et al., *Gene*, 137(1):109-18 (1993). The CDR may be CDRH3 and/or CDRL3. The CDR may be one or more of CDRL1, CDRL2, CDRL3, CDRH1, CDRH2, and/or CDRH3. The CDR may be a Kabat CDR, a Chothia CDR, or an extended CDR.

Candidates with improved binding may be sequenced, thereby identifying a CDR substitution mutant which results in improved affinity (also termed an "improved" substitution). Candidates that bind may also be sequenced, thereby identifying a CDR substitution which retains binding.

Multiple rounds of screening may be conducted. For example, candidates (each comprising an amino acid substitution at one or more position of one or more CDR) with improved binding are also useful for the design of a second library containing at least the original and substituted amino acid at each improved CDR position (i.e., amino acid position in the CDR at which a substitution mutant showed improved binding). Preparation, and screening or selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acids (including all 20 amino acids), and positions in the CDRs which cannot be changed or which can only be changed to a few amino acids.

Candidates with improved affinity may be combined in a second library, which includes the improved amino acid, the original amino acid at that position, and may further include additional substitutions at that position, depending on the complexity of the library that is desired, or permitted using the desired screening or selection method. In addition, if desired, adjacent amino acid position can be randomized to at least two or more amino acids. Randomization of adjacent amino acids may permit additional conformational flexibility in the mutant CDR, which may in turn, permit or facilitate the introduction of a larger number of improving mutations. The library may also comprise substitution at positions that did not show improved affinity in the first round of screening.

The second library is screened or selected for library members with improved and/or altered binding affinity using any method known in the art, including screening using Biacore surface plasmon resonance analysis, and selection using any method known in the art for selection, including phage display, yeast display, and ribosome display.

Compositions

Therapeutic formulations of an antibody described herein may be for storage by mixing an antibody having the desired degree of purity with optional pharmaceutically acceptable carriers, excipients or stabilizers (Remington, The Science and Practice of Pharmacy 20th Ed. Mack Publishing (2000)), in the form of lyophilized formulations or aqueous solutions.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well-known conventional methods (see, for example, Remington's Pharmaceutical Sciences, 18th edition, A. Gennaro, Ed., Mack Publishing Co., Easton, Pa., 1990; and Remington, The Science and Practice of Pharmacy 20th Ed. Mack Publishing, 2000).

Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosacchandes, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulations to be used for in vivo administration may be sterilized. This may be accomplished by, for example, filtration through sterile filtration membranes, or any other art-recognized method for sterilization. Antibody compositions are generally placed into a container having a sterile access port, for example, an intravenous solution bag or vial having a stopper pierceable by a hypodermic injection needle. Other methods for sterilization and filtration are known in the art and are contemplated herein.

In one embodiment of the present invention, the compositions are formulated to be free of pyrogens such that they are acceptable for administration to a subject. Testing compositions for pyrogens and preparing pharmaceutical compositions free of pyrogens are well understood to one of ordinary skill in the art.

The compositions according to the present invention may be in unit dosage forms such as solutions or suspensions, tablets, pills, capsules, powders, granules, or suppositories, etc., for intravenous, oral, parenteral or rectal administration, or administration by inhalation or insufflation.

The phrase "pharmaceutically acceptable" refers to molecular entities and compositions that are physiologically tolerable and do not typically produce an allergic or similar untoward reaction, such as gastric upset, dizziness and the like, when administered to a subject.

In some instances, an antibody can be bound to one or more carriers. Carriers can be active and/or inert. Examples of well-known carriers include polypropylene, polystyrene, polyethylene, dextran, nylon, amylases, glass, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

A term "unit dose" when used in reference to a therapeutic composition or pharmaceutical composition refers to physically discrete units suitable as unitary dosage for humans, each unit containing a predetermined quantity of active material calculated to produce the desired therapeutic effect in association with the required diluent; i.e., carrier, or vehicle.

The compositions can be administered in a manner compatible with the dosage formulation, and in a therapeutically effective amount. The quantity to be administered depends on the subject to be treated, capacity of the subject's immune system to utilize the active ingredient, and degree of binding capacity desired. Precise amounts of active ingredient required to be administered depend on the judgment of the practitioner and are peculiar to each individual. Suitable regimes for initial administration and booster shots are also variable, but are typified by an initial administration followed by repeated doses at one or more hour intervals by a subsequent injection or other administration. Booster doses can also be given at 2-week, 2-month, 6-month intervals, or at any other appropriate interval. Alternatively, continuous intravenous infusion sufficient to maintain concentrations in the blood are contemplated.

One embodiment contemplates the use of the antibodies described herein to manufacture a medicament for treating a condition, disease or disorder described herein. Medicaments can be formulated based on the physical characteristics of the subject needing treatment, and can be formulated in single or multiple formulations based on the stage of the condition, disease or disorder. Medicaments can be packaged in a suitable package with appropriate labels for the distribution to hospitals and clinics wherein the label is for the indication of treating a subject having a disease described herein. Medicaments can be packaged as a single or multiple units. Instructions for the dosage and administration of the compositions can be included with the packages as described below. The invention is further directed to medicaments of an antibody or antigen binding fragment thereof described herein and a pharmaceutically acceptable carrier.

Provided herein are compositions of antibodies and antigen-binding fragments thereof that bind G-CSF and include those such as described elsewhere herein. Antibodies and antigen-binding fragments thereof that bind G-CSF as described herein can be used for the treatment of various forms cancer (e.g., primary tumors and metastases).

A composition (an antibody or an antigen-binding fragment described herein) can be administered alone or in combination with a second composition either simultaneously or sequentially dependent upon the condition to be treated. In one embodiment, a second therapeutic treatment is an angiogenesis inhibitor (e.g., an anti-VEGF agent or a chemotherapeutic agent). When two or more compositions are administered, the compositions can be administered in combination (either sequentially or simultaneously). A composition can be administered in a single dose or multiple doses. An anti-VEGF agent contemplated for use in the methods described herein include, but are not limited to, ranibizumab (LUCENTIS®), aflibercept (VEGF-Trap), sunitinib (SUTENT®), sorafenib (NEXAVAR®), axitinib, pegaptanib and pazopanib.

One embodiment of the present invention contemplates the use of any of the compositions of the present invention to make a medicament for treating a cancer. Medicaments can be formulated based on the physical characteristics of the subject needing treatment, and can be formulated in single or multiple formulations based on the disorder. Medicaments of the present invention can be packaged in a suitable pharmaceutical package with appropriate labels for the distribution to hospitals and clinics wherein the label is for the indication of treating a cancer as described herein in a subject. Medicaments can be packaged as a single or multiple units. Instructions for the dosage and administration of the pharmaceutical compositions of the present invention can be included with the pharmaceutical packages.

Methods of Treatment

An "individual" or a "subject" to be treated by a method herein may be a mammal, more preferably a human. Mammals also include, but are not limited to, farm animals, sport animals, and pets, including, but not limited to, primates, equines, bovines, alpacas, dogs, cats, rabbits, mice and rats.

It will be appreciated that a "subject in need thereof" may be suffering from a disease, such as a cancer, or a metastasis thereof, but may not yet be symptomatic for the disease. For example, where the cancer is colon cancer (which is associated with the mutant K-ras protein), a subject with a mutant K-ras protein in some cells of the colon is a subject according to the invention even though that subject may not yet be symptomatic for colon cancer. The subject in need thereof may also be a subject with arthritis or other inflammatory diseases.

"Signs or symptoms of illness" are clinically recognized manifestations or indications of disease.

As used herein, a "therapeutically effective dosage" or a "therapeutically effective amount" of a pharmaceutical composition described herein is an amount sufficient to effect beneficial or desired results. Beneficial or desired results include results such as lessening the severity or delaying the progression of the disease, including biochemical, histological and/or behavioral symptoms of the disease, its complications and intermediate pathological phenotypes presenting during development of the disease. A therapeutically-effective amount of a therapeutic agent (including agonist, antagonist, and/or the like) can vary based on different factors, such as the disease state, age, sex, and weight of the subject, and the ability of the therapeutic agent to elicit a desired response in the subject. A therapeutically-effective amount is also one in which any toxic or detrimental effects of the substance/molecule, agonist, or antagonist are outweighed by the therapeutically-beneficial effects.

As is understood in the clinical context, an effective dosage of a pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved. Accordingly, in some instances, one or more therapeutic agents may be administered to the subject. In other instances, treatment with a pharmaceutical composition described herein is conducted prior to, or after, one or more other treatment modalities described herein.

The term "treatment", "treat", or "treating" refers to clinical intervention in an attempt to alter the natural course of the individual being treated, and can be performed either for prophylaxis or during the course of clinical pathology. Effects of treatment can include preventing occurrence or recurrence of disease, alleviating symptoms, diminishing any direct or indirect pathological consequences of disease, preventing metastasis, decreasing the rate of disease progression, ameliorating the disease state, minimizing the clinical impairment or symptoms resulting from the disease, diminishing any pain or discomfort suffered by the subject, remission or improved prognosis, and extending the survival of a subject beyond that which would otherwise be expected in the absence of such treatment. Treatment can result from a reduction of suppression of immune functions caused by a disease, such as suppression of T cells and the like.

By "treating" a subject suffering from a cancer or a metastasis thereof, it is meant that the subject's symptoms can be partially alleviated, totally alleviated, or remain static following treatment according to the invention. A subject that has been treated can exhibit a partial or total alleviation of tumor load. In one non-limiting example, a subject suffering from a highly metastatic cancer (e.g., breast cancer) is treated where additional metastasis either do not occur, or are reduced in number as compared to a subject who does not receive treatment. In another non-limiting example, a subject is treated where the subject's solid cancer either becomes reduced in size or does not increase in size as compared to a subject who does not receive treatment. In yet another non-limiting example, the number of cancer cells in a treated subject either does not increase or is reduced as compared to the number of cancer cells in a subject who does not receive treatment. Improvement can also be defined, for example, as decreased cell proliferation, decreased numbers of cells, increased apoptosis, and/or increased survival of the subject being treated. Treatment of cancer also includes inhibiting or preventing the development or spread of the cancerous cells or by limiting, suspending, terminating, or otherwise controlling the maturation and proliferation of cells involved in the cancer Various formulations of an anti-G-CSF antibody may be used for administration. In some embodiments, the anti-G-CSF antibody may be administered neat. In some embodiments, the anti-G-CSF antibody and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and non-parenteral drug delivery are set forth in Remington, The Science and Practice of Pharmacy 20th Ed. Mack Publishing (2000).

In some embodiments, these antibodies are formulated for administration to a subject by known procedures, including, without limitation, oral administration, parenteral administration (e.g., epifascial, intracapsular, intracutaneous, intradermal, intramuscular, intraorbital, intraperitoneal, intraspinal, intrasternal, intravascular, intravenous, parenchymatous, or subcutaneous administration) transdermal administration, and the like. Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

For oral administration, the formulation of the antibodies can be presented as capsules, tablets, powders, granules, or as a suspension. The formulation can have conventional additives, such as lactose, mannitol, corn starch, or potato starch. The formulation can also be presented with binders, such as crystalline cellulose, cellulose derivatives, acacia, corn starch, or gelatins. Additionally, the formulation can be presented with disintegrators, such as corn starch, potato starch, or sodium carboxymethylcellulose. The formulation can also be presented with dibasic calcium phosphate anhydrous or sodium starch glycolate. Finally, the formulation can be presented with lubricants, such as talc or magnesium stearate.

For parenteral administration, the antibody can be suspended in a sterile aqueous solution which is preferably isotonic with the blood of the subject. Such a formulation can be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulations can be presented in unit or multi-dose containers, such as sealed ampules or vials. The formulation can be delivered by any mode of injection, including, without limitation, epifascial, intracapsular, intracutaneous, intradermal, intramuscular, intraorbital, intraperitoneal, intraspinal, intrasternal, intravascular, intravenous, parenchymatous, or subcutaneous.

Anti-G-CSF antibodies can also be administered via inhalation, as described herein.

Generally, for administration of anti-G-CSF antibodies, an initial candidate dosage can be about 2 mg/kg. For the purpose of the present invention, a typical daily dosage can be up to 3 µg/kg, up to about 30 µg/kg, up to about 300 µg/kg, up to about 3 mg/kg, up to 30 mg/kg, up to 100 mg/kg or more, or any integer therebetween, depending on the factors mentioned above. For example, a dosage of about 1 mg/kg, about 2.5 mg/kg, about 5 mg/kg, about 10 mg/kg, or about 25 mg/kg may be used.

For repeated administrations over several days or longer, depending on the condition, the treatment is sustained until a desired suppression of symptoms occurs or until sufficient therapeutic levels are achieved, for example, to reduce pain. An exemplary dosing regimen comprises administering an initial dose of about 2 mg/kg, followed by a weekly maintenance dose of about 1 mg/kg of the anti-G-CSF antibody, or followed by a maintenance dose of about 1 mg/kg every other week.

However, other dosage regimens may be useful, depending on the pattern of pharmacokinetic decay that the practitioner wishes to achieve. For example, in some embodiments, dosing from one-four times a week is contemplated. The progress of this therapy is easily monitored by conventional techniques and assays. The dosing regimen can vary over time.

The appropriate dosage of an anti-G-CSF antibody will depend on the anti-G-CSF antibody employed, the type and stage of disease to be treated, previous surgery and/or therapy, the subject's clinical history and response to the antibody, and the discretion of the attending physician.

Typically the clinician will administer an anti-G-CSF antibody, until a dosage is reached that achieves the desired result. Dose and/or frequency can vary over course of treatment.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system.

Frequency of administration may be determined and adjusted over the course of therapy. Alternatively, sustained continuous release formulations of anti-G-CSF antibodies may be appropriate. Various formulations and devices for achieving sustained release are known in the art. To assess efficacy of an anti-G-CSF antibody, an indicator of the disease can be followed.

As further used herein, treatment of cancer includes stasis, partial or total elimination of a cancerous growth or tumor. Treatment or partial elimination includes, for example, a fold reduction in growth or tumor size and/or volume such as about 2-fold, about 3-fold, about 4-fold, about 5-fold, about 10-fold, about 20-fold, about 50-fold, or any fold reduction in between. Similarly, treatment or partial elimination can include a percent reduction in growth or tumor size and/or volume of about 1%, about 2%, about 3%, about 4%, about 5%, about 10%, about 20%, about 30%, about 40%, about 50%, about 60%, about 70%, about 80%, about 90%, about 95%, about 99%, 100%, or any percentage reduction in between.

Diagnosis or assessment of cancers is well-established in the art. Assessment may be performed based on subjective measures, such as patient characterization of symptoms. Assessment may also be performed based on objective measures such as, for example, testing a blood or tissue sample for one or more cancer antigens. Further types of assessments are described below.

Treatment efficacy can be assessed by methods well-known in the art.

Non-limiting examples of tumors include a lung cancer, a breast cancer, an ovarian cancer, a colon cancer, a pancreatic cancer, a brain cancer, or a skin cancer.

The term "tumor" is used herein to refer to a cancerous tissue (as compared to expression by normal tissue of the same type). Tumors can include solid tumors and semi-solid tumors. Tumors may also, in some instances, be metastatic.

Lung Cancer

In a method described herein, a subject in need thereof having a lung cancer is administered a therapeutically effective amount of a pharmaceutical composition that comprises an antibody, or antigen-binding fragment thereof described herein.

The most common type of lung cancer is non-small cell lung cancer (NSCLC), which accounts for approximately 80-85% of lung cancers and is divided into squamous cell carcinomas, adenocarcinomas, and large cell undifferentiated carcinomas. Small cell lung cancer accounts for approximately 15-20% of lung cancers.

Lung cancer staging is an assessment of the degree of spread of the cancer from its original source. It is an important factor affecting the prognosis and potential treatment of lung cancer. Non-small cell lung carcinoma is staged from IA ("one A"; best prognosis) to W ("four"; worst prognosis). Small cell lung carcinoma is classified as limited stage if it is confined to one half of the chest and within the scope of a single radiotherapy field; otherwise, it is extensive stage.

Non-small cell lung cancer may be staged using EUS (endoscopic ultrasound) or CT or MRI scan or at surgery to classify the extent of disease according to the TNM system. These subjects undergo staging as part of the process of considering prognosis and treatment. The AJCC recommends TNM staging followed by further grouping.

Primary tumor (T): TX: The primary tumor cannot be assessed, or there are malignant cells in the sputum or bronchoalveolar lavage but not seen on imaging or bronchoscopy; Tis: Carcinoma in situ. T0: No evidence of primary tumor. T1: Tumor less than 3 cm in its greatest dimension, surrounded by lung or visceral pleura and without bronchoscopic invasion into the main bronchus. T2: A tumor with any of: more than 3 cm in greatest dimension; extending into the main bronchus (but more than 2 cm distal to the carina), and obstructive pneumonitis (but not involving the entire lung). T3: A tumor with any of: invasion of the chest wall, diaphragm, mediastinal pleura, or parietal pericardium; extending into the main bronchus, within 2 cm of the carina, but not involving the carina; and obstructive pneumonitis of the entire lung. T4: A tumor with any of: invasion of the mediastinum, heart, great vessels, trachea, esophagus, vertebra, or carina; separate tumor nodules in the same lobe; and malignant pleural effusion. Lymph nodes (N): NX: Lymph nodes cannot be assessed; N0: No lymph nodes involved; N1: Metastasis to ipsilateral peribronchial or ipsilateral hilar lymph nodes; N2: Metastasis to ipsilateral mediastinal or subcarinal lymph nodes; and N3: Metastasis to any of: ipsilateral supraclavicular lymph nodes; ipsilateral scalene lymph nodes; and contralateral lymph nodes. Distant metastasis (M): MX: Distant metastasis cannot be assessed; M0: No distant metastasis; and M1: Distant metastasis is present.

Where combination therapy is contemplated for treatment of lung cancer, the one or more additional therapeutic treatments is surgery, radiotherapy (e.g., thoracic radiotherapy, radiation therapy with charged particles, Uracil-tegafur and Platinum-based chemotherapy (e.g., cisplatin, carboplatin, oxaliplatin, etc.), vinorelbine, Erlotinib (TARCEVA®), Gefitinib (IRESSA®), anti-epidermal growth factor receptor antibodies (e.g., Cetuximab), anti-vascular endothelial growth factor antibodies (e.g., Bevacizumab), small molecule inhibitors of tyrosine kinases, direct inhibitors of proteins involved in lung cancer cell proliferation, Aurora kinase inhibitors, laser-induced thermotherapy, RNAi therapy, whole tumor cells genetically modified to secrete granulocyte macrophage-colony stimulating factor (GM-CSF) (also known as GVAX), or any combination thereof. Additional therapeutic treatments include Taxol, pemetrexed, anti-CTLA-4 (YERVOY), anti-PD-1 (OPDIVO, KEYTRUDA), anti-PDL1 (BMS-936559, MPDL3280A), Others in development Pidilizumab (CT-011, anti-PD-1) by Medivation/CureTech, MEDI4736 (anti-PD-L1) by AstraZeneca, and Avelumab (MSB0010718C, anti-PD-L1) by Merck-Sorono.

In other instances, where combination therapy is contemplated for treatment of lung cancer, the one or more additional therapeutic treatments is immunotherapy including, but not limited to Chimeric-antigen receptor (CAR)-redirected T cells (CAR-T) cell therapy or adoptive T cell therapy (ACT).

Breast Cancer

In a method described herein, a subject in need thereof having a breast cancer is administered a therapeutically effective amount of a pharmaceutical composition that comprises an antibody, or antigen-binding fragment thereof described herein. As used herein, "breast cancer" also encompasses a phenotype that displays a predisposition towards developing breast cancer in an individual.

A breast cancer to be treated using the methods described herein includes any type of breast cancer that can develop in a female subject. For example, the breast cancer may be characterized as Luminal A (ER+ and/or PR+, HER2–, low Ki67), Luminal B (ER+ and/or PR+, HER2+(or HER2– with high Ki67), Triple negative/basal-like (ER–, PR–, HER2–) or HER2 type (ER–, PR–, HER2+). In another example, the breast cancer may be resistant to therapy or therapies such as alkylating agents, platinum agents, taxanes, vinca agents, anti-estrogen drugs, aromatase inhibitors, ovarian suppression agents, endocrine/hormonal agents, bisphophonate therapy agents or targeted biological therapy agents.

A lobular carcinoma in situ and a ductal carcinoma in situ are breast cancers that have developed in the lobules and ducts, respectively, but have not spread to the fatty tissue surrounding the breast or to other areas of the body. Infiltrating (or invasive) lobular and ductal carcinoma are cancers that have developed in the lobules and ducts, respectively, and have spread to either the breast's fatty tissue and/or other parts of the body. In one aspect, provided herein is a method of treating breast cancer, such as a ductal carcinoma in duct tissue in a mammary gland, a breast cancer that is Her2– and/or ER– and/or PR–. Other cancers of the breast that would benefit from treatment by the methods are medullary carcinomas, colloid carcinomas, tubular carcinomas, and inflammatory breast cancer.

In one embodiment, breast cancer is staged according to the TNM system. Prognosis is closely linked to results of staging, and staging is also used to allocate patients to treatments both in clinical trials and clinical practice.

Briefly, the information for staging is as follows: TX: Primary tumor cannot be assessed. T0: No evidence of tumor. Tis: Carcinoma in situ, no invasion; T1: Tumor is 2 cm or less; T2: Tumor is more than 2 cm but not more than 5 cm; T3: Tumor is more than 5 cm; T4: Tumor of any size growing into the chest wall or skin, or inflammatory breast cancer. NX: Nearby lymph nodes cannot be assessed N0: cancer has not spread to regional lymph nodes. N1: cancer has spread to 1 to 3 maxillary or one internal mammary lymph node N2: cancer has spread to 4 to 9 maxillary lymph nodes or multiple internal mammary lymph nodes N3: One of the following applies: cancer has spread to 10 or more maxillary lymph nodes, or cancer has spread to the lymph nodes under the clavicle (collar bone), or cancer has spread to the lymph nodes above the clavicle, or cancer involves maxillary lymph nodes and has enlarged the internal mammary lymph nodes, or cancer involves 4 or more maxillary lymph nodes, and tiny amounts of cancer are found in internal mammary lymph nodes on sentinel lymph node biopsy. MX: presence of distant spread (metastasis) cannot be assessed. M0: no distant spread. M1: spread to distant organs (not including the supraclavicular lymph node) has occurred.

Where combination therapy is contemplated for treatment of breast cancer, the one or more additional therapeutic treatments is surgery, monoclonal antibodies (e.g., Her-2 antibodies, herceptin), adjuvant chemotherapy such as single agent chemotherapy or combination chemotherapy (e.g., anthracycline- and taxane-based polychemotherapies, taxol, or target-specific trastuzumab with or without endocrine manipulation with or without PMRT, vinorelbine), adriamycin, cyclophosphamide, xeloda, taxotere, selective estrogen receptor modulators such as Tamoxifen and Raloxifene, allosteric estrogen receptor modulators such as Trilostane, radiation (e.g., interstitial brachytherapy, Mammosite device, 3-dimensional conformal external radiation and intraoperative radiotherapy), Aromatase inhibitors that suppress total body synthesis (e.g., anastrozole, exemestane and letrozole), RNAi therapy, intravenous analogs of rapamycin that are immunosuppressive and anti-proliferative such as Temsirolimus (CCI779), or any combination thereof. Additional therapies include, but are not limited to, anti-CTLA-4 (YERVOY), anti-PD-1 (OPDIVO, KEYTRUDA), anti-PDL1 (BMS-936559, MPDL3280A), Others in development Pidilizumab (CT-011, anti-PD-1) by Medivation/CureTech, MEDI4736 (anti-PD-L1) by AstraZeneca, and Avelumab (MSB0010718C, anti-PD-L1) by Merck-Sorono.

In other instances, where combination therapy is contemplated for treatment of lung cancer, the one or more additional therapeutic treatments is immunotherapy including, but not limited to Chimeric-antigen receptor (CAR)-redirected T cells (CAR-T) cell therapy or adoptive T cell therapy (ACT).

Ovarian Cancer

In a method described herein, a subject in need thereof having an ovarian cancer is administered a therapeutically effective amount of a pharmaceutical composition that comprises an antibody, or antigen-binding fragment thereof described herein.

Ovarian cancer is classified according to the histology of the tumor, obtained in a pathology report. Surface epithelial-stromal tumor, also known as ovarian epithelial carcinoma, is the most typical type of ovarian cancer. It includes serous tumor, endometrioid tumor and mucinous cystadenocarcinoma. Sex cord-stromal tumor, including estrogen-producing granulosa cell tumor and virilizing Sertoli-Leydig cell tumor or arrhenoblastoma, accounts for 8% of ovarian cancers. Germ cell tumor accounts for approximately 30% of ovarian tumors but only 5% of ovarian cancers because most germ cell tumors are teratomas and most teratomas are benign. Germ cell tumor tends to occur in young women and girls. The prognosis depends on the specific histology of germ cell tumor, but overall is favorable. Mixed tumors contain elements of more than one of the above classes of tumor histology.

Ovarian cancer can also be a secondary cancer, the result of metastasis from a primary cancer elsewhere in the body. Common primary cancers are breast cancer and gastrointestinal cancer (in which case the ovarian cancer is a Krukenberg cancer). Surface epithelial-stromal tumor can originate in the peritoneum (the lining of the abdominal cavity), in which case the ovarian cancer is secondary to primary peritoneal cancer, but treatment is basically the same as for primary surface epithelial-stromal tumor involving the peritoneum.

Ovarian cancer staging is by the FIGO staging system and uses information obtained after surgery, which can include a total abdominal hysterectomy, removal of both ovaries and fallopian tubes, the omentum, and pelvic (peritoneal) washings for cytology. The AJCC stage is the same as the FIGO stage.

Stage I refers to ovarian cancer limited to one or both ovaries: IA—involves one ovary; capsule intact; no tumor on ovarian surface; no malignant cells in ascites or peritoneal washings; IB—involves both ovaries; capsule intact; no tumor on ovarian surface; negative washings; and IC—tumor limited to ovaries with any of the following: capsule ruptured, tumor on ovarian surface, positive washings.

Stage II refers to pelvic extension or implants: IIA—extension or implants onto uterus or fallopian tube; negative washings; IIB—extension or implants onto other pelvic structures; negative washings; and IIC—pelvic extension or implants with positive peritoneal washings Stage III refers to microscopic peritoneal implants outside of the pelvis; or limited to the pelvis with extension to the small bowel or omentum: IIIA—microscopic peritoneal metastases beyond pelvis; IIIB—macroscopic peritoneal metastases beyond pelvis less than 2 cm in size; and IIIC—peritoneal metastases beyond pelvis >2 cm or lymph node metastases Stage IV refers to distant metastases to the liver or outside the peritoneal cavity.

Para-aortic lymph node metastases are considered regional lymph nodes (Stage IIIC).

In some embodiments, the methods described herein treat an ovarian cancer selected from the following: an adenocarcinoma in the ovary and an adenocarcinoma that has migrated from the ovary into the abdominal cavity.

Where combination therapy is contemplated for treatment of ovarian cancer, the one or more additional therapeutic treatments is surgery, chemotherapy (e.g., doxorubicin, doxil, gemcitabine, Rubitecan, and platinum-based chemotherapeutics such as cisplatin, carboplatin and oxaliplatin), melphalan, paclitaxel, topoisomerase I inhibitors such as topotecan and irinotecan, taxane-based therapy, hormones, radiation therapy, whole body hypothermia, isoflavone derivatives such as Phenoxodial, cytotoxic macrolides such as Epothilones, angiogenesis inhibitors such as bevacizumab, signal transduction inhibitors such as trastuzumab, gene therapy, RNAi therapy, immunotherapy, monoclonal antibodies, phosphatidylinositol-like kinase inhibitors such as rapamycin, or any combination thereof. In one embodiment the combination is an anti-G-CSF antibody or antigen-binding fragment thereof and doxil. In another embodiment, the combination is an anti-G-CSF antibody or antigen-binding fragment thereof and topotecan. In yet another embodiment, the combination is an anti-G-CSF antibody or antigen-binding fragment thereof and a VEGF receptor inhibitor. Non-limiting examples of VEGF receptor inhibitors include bevacizumab (AVASTIN®), ranibizumab (LUCENTIS®), aflibercept (VEGF-Trap), sunitinib (SUTENT®), sorafenib (NEXAVAR®), axitinib, pegaptanib and pazopanib. The combination therapy of the antibodies and antigen-binding fragments described herein with the ovarian cancer therapies may also provide for lower doses of either therapy, or both, due to a synergistic effect from the co-administration of the therapies. Additional therapies include, but are not limited to, anti-CTLA-4 (YERVOY), anti-PD-1 (OPDIVO, KEYTRUDA), anti-PDL1 (BMS-936559, MPDL3280A), Others in development Pidilizumab (CT-011, anti-PD-1) by Medivation/CureTech, MEDI4736 (anti-PD-L1) by AstraZeneca, and Avelumab (MSB0010718C, anti-PD-L1) by Merck-Sorono.

In other instances, where combination therapy is contemplated for treatment of lung cancer, the one or more additional therapeutic treatments is immunotherapy including, but not limited to Chimeric-antigen receptor (CAR)-redirected T cells (CAR-T) cell therapy or adoptive T cell therapy (ACT).

Colon Cancer or Colorectal Cancer

In a method described herein, a subject in need thereof having a colon cancer is administered a therapeutically effective amount of a pharmaceutical composition that comprises an antibody, or antigen-binding fragment thereof described herein. Colorectal cancer (also called colon cancer or large bowel cancer) includes cancerous growths in the colon, rectum (anus) and appendix.

Dukes classification may be used to classify colorectal cancer based on stages A-D. Stage A refers to colorectal cancer that is limited to mucosa (i.e., has not invaded through the bowel wall). Stage B1 refers to extending into muscularis propria, but not penetrating through it (i.e., lymph nodes have not been invaded); whereas Stage B2 cancer has penetrated through the muscularis propria, but not penetrating through it (i.e., lymph nodes have not been invaded). Stage C1 refers to cancer that extends into the muscularis propria, but not penetrating through it (i.e., lymph nodes are involved); whereas Stage C2 refers to cancer that extends into the muscularis propria and penetrating through it (i.e., lymph nodes are involved). Stage D refers to distant metastatic spread. The TNM system may also be used to stage colorectal cancer according to conventional means known in the art.

Where combination therapy is contemplated for treatment of colon cancer or colorectal cancer, the one or more additional therapeutic treatments is surgery, radiation therapy, and chemotherapy (e.g., 5-fluorouracil, levamisole, leucovorin or semustine (methyl CCNU)), N-[2-(dimethylamino)ethyl]acridine-4-carboxamide and other related carboxamide anticancer drugs; non-topoisomerase II inhibitors, irinotecan, liposomal topotecan, taxane class of anticancer agents (e.g., paclitaxel or docetaxel), a compound of the xanthenone acetic acid class (e.g., 5,6-dimethylanthenone-4-acetic acid PMAA), laminarin, site-selective cyclic AMP Analogs (e.g., 8-chloroadenosine 3',5'-cyclic phosphate), pyranoindole inhibitors of Cox-2, carbazole inhibitors of Cox-2, tetrahydrocarbazole inhibitors of Cox-2, indene inhibitors of Cox-2, localized inhibitors of NSAIDS (e.g., anthranilic acids, aspirin (5-acetylsalicylic acid), azodisal sodium, carboheterocyclic acids, carprofen, chlorambucil, diclophenac, fenbufen, fenclofenac, fenoprofen, flufenamic acid, flurbiprofen, fluprofen, furosemide, gold sodium thiomalate, ibuprofen, indomethacin, indoprofen, ketoprofen, lonazolac, loxoprofen, meclofenamic acid, mefanamic acid, melphalan, naproxen, penicillamine, phenylacetic acids, proprionic acids, salicylic acids, salazosulfapyridine, sulindac, tolmetin, a pyrazolone butazone propazone NSAID, meloxicam, oxicams, piroxicam, feldene, piroxicam beta cyclodextran, tenoxicam, etodolac, and oxaprozin), an inhibitor of HER-2/neu, RNAi therapy, GM-CSF, monoclonal antibodies (e.g., anti-Her-2/neu antibodies, anti-CEA antibodies, A33 (HB 8779), 100-210 (HB 11764) and 100-310 (HB 11028)), erbitux, vectibix, hormonal therapy, pyrimidineamines, camptothecin derivatives (e.g., CPT-11), folinic acid (FA), Gemcitabine, Ara-C, platinum-based chemotherapeutics such as cisplatin, carboplatin and oxaliplatin, a cGMP-specific phosphodiesterase inhibitor, or any combination thereof. Additional therapies include, but are not limited to, anti-CTLA-4 (YERVOY), anti-PD-1 (OPDIVO, KEYTRUDA), anti-PDL1 (BMS-936559, MPDL3280A), Others in development Pidilizumab (CT-011, anti-PD-1) by Medivation/CureTech, MEDI4736 (anti-PD-L1) by AstraZeneca, and Avelumab (MSB0010718C, anti-PD-L1) by Merck-Sorono.

In other instances, where combination therapy is contemplated for treatment of lung cancer, the one or more additional therapeutic treatments is immunotherapy including, but not limited to Chimeric-antigen receptor (CAR)-redirected T cells (CAR-T) cell therapy or adoptive T cell therapy (ACT).

Pancreatic Cancer

In a method described herein, a subject in need thereof having a pancreatic cancer is administered a therapeutically effective amount of a pharmaceutical composition that comprises an antibody, or antigen-binding fragment thereof described herein.

Pancreatic cancers to be treated by the methods described herein include, but are not limited to, an epithelial carcinoma in the pancreatic duct tissue and an adenocarcinoma in a pancreatic duct. The most common type of pancreatic cancer is an adenocarcinoma, which occurs in the lining of the pancreatic duct.

Where combination therapy is contemplated for treatment of pancreatic cancer, the one or more additional therapeutic treatments is surgery, radiation therapy (RT), Fluorouracil (5-FU) and RT, systemic therapy, stenting, Gemcitabine (GEMZAR®), Gemcitabine and RT, Cetuximab, erlotinib (TARCEVA®), chemoradiation, bevacizumab (AVASTIN®), or any combination thereof. In yet another embodiment, the combination is an anti-G-CSF antibody or antigen-binding fragment thereof and a VEGF receptor inhibitor. Non-limiting examples of VEGF receptor inhibitors include bevacizumab (AVASTIN®), ranibizumab (LUCENTIS®), aflibercept (VEGF-Trap), sunitinib (SUTENT®), sorafenib (NEXAVAR®), axitinib, pegaptanib and pazopanib. Additional therapies include, but are not limited to, anti-CTLA-4 (YERVOY), anti-PD-1 (OPDIVO, KEYTRUDA), anti-PDL1 (BMS-936559, MPDL3280A), Others in development Pidilizumab (CT-011, anti-PD-1) by Medivation/CureTech, MEDI4736 (anti-PD-L1) by AstraZeneca, and Avelumab (MSB0010718C, anti-PD-L1) by Merck-Sorono.

In other instances, where combination therapy is contemplated for treatment of lung cancer, the one or more additional therapeutic treatments is immunotherapy including, but not limited to Chimeric-antigen receptor (CAR)-redirected T cells (CAR-T) cell therapy or adoptive T cell therapy (ACT).

Brain Cancer

In a method described herein, a subject in need thereof having a brain cancer is administered a therapeutically effective amount of a pharmaceutical composition that comprises an antibody, or antigen-binding fragment thereof described herein.

Antibodies, or antigen-binding fragments thereof, described herein can also be modified so that they are able to cross the blood-brain barrier. Such modification of the antibodies or antigen-binding fragments described herein allows for the treatment of brain diseases such as glioblastoma multiforme (GBM). Exemplary modifications to allow proteins such as antibodies or antigen-binding fragments to cross the blood-brain barrier are described in US Patent Application Publication 2007/0082380 which is hereby incorporated by reference with respect to modification of antibodies to cross the blood brain barrier.

Primary brain tumors to be treated using the methods described herein include, but are not limited to, meningiomas, astrocytomas such as glioblastomas (e.g., glioblastoma multiforme (GBM), and malignant medulloblastomas. Diagnosis is usually by medical examination along with computed tomography or magnetic resonance imaging. A diagnosis may be confirmed by a biopsy. Based on the findings, the tumors are divided into different grades of severity.

Where combination therapy is contemplated for treatment of brain cancer, treatment may also include surgery, radiation therapy, chemotherapy and/or anticonvulsant medication. Dexamethasone and furosemide may be used to decrease swelling around the tumor. Additional therapies include, but are not limited to, anti-CTLA-4 (YERVOY), anti-PD-1 (OPDIVO, KEYTRUDA), anti-PDL1 (BMS-936559, MPDL3280A), Others in development Pidilizumab (CT-011, anti-PD-1) by Medivation/CureTech, MEDI4736 (anti-PD-L1) by AstraZeneca, and Avelumab (MSB0010718C, anti-PD-L1) by Merck-Sorono.

In other instances, where combination therapy is contemplated for treatment of lung cancer, the one or more additional therapeutic treatments is immunotherapy including, but not limited to Chimeric-antigen receptor (CAR)-redirected T cells (CAR-T) cell therapy or adoptive T cell therapy (ACT).

Skin Cancer

In a method described herein, a subject in need thereof having an ovarian cancer is administered a therapeutically effective amount of a pharmaceutical composition that comprises an antibody, or antigen-binding fragment thereof described herein.

There are three main types of skin cancer: basal-cell skin cancer (BCC), squamous-cell skin cancer (SCC) and melanoma.

A melanoma is a malignant tumor of melanocytes which are found predominantly in skin but also in the bowel and the eye (uveal melanoma). It is one of the rarer types of skin cancer but causes the majority of skin cancer related deaths. Malignant melanoma is a serious type of skin cancer caused by uncontrolled growth of pigment cells, called melanocytes. Melanomas also include, but are not limited to, a choroidea melanoma, malignant melanomas, cutaneous melanomas and intraocular melanomas.

Melanoma may be divided into the following types: Lentigo maligna, Lentigo maligna melanoma, superficially spreading melanoma, acral lentiginous melanoma, mucosal melanoma, nodular melanoma, polypoid melanoma, desmoplastic melanoma, amelanotic melanoma, soft-tissue melanoma, and uveal melanoma.

Where combination therapy is contemplated for treatment of skin cancer, the one or more additional treatments include, but are not limited to, surgery, chemotherapy, (external beam radiotherapy or brachytherapy), topical chemotherapy (imiquimod or 5-fluorouracil), cryotherapy (freezing the cancer off), targeted therapy, photodynamic therapy, topical chemotherapy, electrodesiccation, curettage or a combination thereof. In a subject whose disease has spread to other areas of their bodies, palliative care may be used to improve quality of life. Additional therapies include, but are not limited to, anti-CTLA-4 (YERVOY), anti-PD-1 (OPDIVO, KEYTRUDA), anti-PDL1 (BMS-936559, MPDL3280A), Others in development Pidilizumab (CT-011, anti-PD-1) by Medivation/CureTech, MEDI4736 (anti-PD-L1) by AstraZeneca, and Avelumab (MSB0010718C, anti-PD-L1) by Merck-Sorono.

In other instances, where combination therapy is contemplated for treatment of lung cancer, the one or more additional therapeutic treatments is immunotherapy including, but not limited to Chimeric-antigen receptor (CAR)-redirected T cells (CAR-T) cell therapy or adoptive T cell therapy (ACT).

Arthritis

In a method described herein, a subject in need thereof having arthritis, including antibody-mediated inflammatory arthritis, such as rheumatoid arthritis, is administered a therapeutically effective amount of a pharmaceutical composition that comprises an anti-G-CSF antibody, or antigen-binding fragment thereof described herein.

Recent literature and publications, such as Lee et al., 2017, J. Immunol, 198:3565-35758, Campbell et al., 2016, J. Immunol., 197: 4392-4402, and Canadian Patent Application No. 2496485 indicate that blocking of G-CSF/G-CSF receptor signaling using antibodies, such as an anti-G-CSF antibody, can treat inflammatory arthritis, including reducing pain and improving prognosis.

Treatment of arthritis includes stasis, partial or total elimination of pain and/or inflammation.

Treatment also includes improvement of a subject's overall functioning.

Diagnosis or assessment of arthritis is well-established in the art. Assessment may be performed based on subjective measures, such as patient characterization of symptoms. Assessment may also be performed based on objective measures such as, for example, imaging, testing a blood or tissue sample for one or more biomarkers for arthritis, such as rheumatoid factor and anti-citrullinated protein antibodies. Assessment may also include anti-cyclic citrullinated peptide ELISA.

Treatment efficacy can be assessed by methods well-known in the art.

Where combination therapy is contemplated for treatment of inflammatory diseases, such as arthritis, the anti-G-CSF antibody or antigen-binding fragment thereof, may be combined with other anti-inflammatory agents or medications used to treat arthritis, including pain medications, known to a person skilled in the art.

Kits

Also provided herein are kits for use in the instant methods. Kits may include one or more containers comprising an anti-G-CSF antibody described herein and instructions for use in accordance with any of the methods described herein. Generally, these instructions comprise a description of administration of the anti-G-CSF antibody to treat a cancer according to any of the methods described herein. The kit may further comprise a description of selecting an individual suitable for treatment based on identifying whether that subject has symptoms of cancer or whether the subject is has a cancer, but is asymptomatic. In still other embodiments, the instructions comprise a description of administering anti-G-CSF antibody to a subject in need thereof.

The instructions relating to the use of an anti-G-CSF antibody generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating a cancer. Instructions may be provided for practicing any of the methods described herein.

The kits may be provided in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-G-CSF antibody described herein. The container may further comprise a second pharmaceutically active agent.

Kits may optionally provide additional components such as buffers and interpretive information. Normally, the kit comprises a container and a label or package insert(s) on or associated with the container.

EXAMPLES

The application may be better understood by reference to the following non-limiting examples, which are provided as exemplary embodiments of the application. The following examples are presented in order to more fully illustrate embodiments and should in no way be construed, however, as limiting the broad scope of the application.

Example 1: Methods of Making Anti-G-CSF Antibodies

Anti-G-CSF antibodies were produced by ImmunoPrecise Antibodies Ltd. (Victoria, BC) using their proprietary Rapid Prime technology.

Mice were immunized with recombinant human G-CSF (Genscript). Following the immunization and priming procedure, splenocytes were fused with the SP2/0 myeloma and screened for antibody producing cells.

Example 2: Method of Screening Binding of Anti-G-CSF Antibodies to G-CSF

Binding of anti-G-CSF antibodies produced by the methods of Example 1 was tested at ImmunoPrecise Antibodies Ltd. using a direct ELISA on plates coated with 0.1 μg/well with human G-CSF (Genscript) in carbonate buffer. Supernatants from 928 hybridoma clones were tested and the 180 clones with the strongest signal (absorbance >0.200) were selected for further testing. These 180 clones were further tested by direct ELISA against human G-CSF and a non-specific protein (human transferrin). 87 clones were found to bind specifically to human G-CSF and not transferrin.

Example 3: Neutralization Assays

Once antibodies were identified as binding specifically to human G-CSF, they were initially tested for neutralization capacity in 2 assays: (1) Inhibition of proliferation of a G-CSF-dependent cell line (NFS-60) and (2) inhibition of proliferation of mouse bone marrow cells cultured in FLT3L+G-CSF.

Inhibition of Proliferation of a GCSF-Dependent Cell Line (NFS60)

$2.5 \times 10^3$ NFS-60 cells were cultured in complete DMEM or RPMI media in the presence of 0.125 ng/mL human G-CSF (Genscript). Supernatants from 87 anti-human-G-CSF antibody clones (1/5 dilution of antibody supernatant) were added to the wells and cultured for 7 days at 37° C. (5% $CO_2$). Wells with and without G-CSF served as negative and positive controls.

Cells were counted on day 7 using the MACSQuant®. Several clones demonstrated a reduction in NFS-60 cell counts to a level near that of NFS-60 cells grown in the absence of G-CSF suggesting that those clones were neutralizing G-CSF activity.

FIG. 1. Plate layout and cell counts of NFS-60 cells cultured in G-CSF in the presence of supernatant from various anti-G-CSF clones (1/5 dilution). Each clone was tested as a single replicate but the assay was repeated 3 times.

Inhibition of Proliferation of Mouse Bone Marrow Cells Cultured in FLT3L+G-CSF

Mouse bone marrow cells [$10^6$ cells/mL] were cultured with recombinant FLT3L (200 ng/mL)+human G-CSF (0.125 ng/mL) in the presence of supernatant from the anti-G-CSF clones (1/5 dilution of supernatant) for 9 days. On day 9 the wells were visually inspected for changes in bone marrow cell proliferation. As bone marrow cells cultured in Flt3L in the presence of G-CSF demonstrate a 3-4-fold increase in cell number, any antibodies which neutralize G-CSF would be expected to cause a decrease in the number of cells in the culture. Cells cultured with and without G-CSF served as negative and positive controls.

Cells were visually inspected on day 9 and wells with a decrease in cell number were noted as containing a potentially neutralizing antibody. This assay was repeated twice and the results were combined with the results of the NFS-60 assay to create a shortlist of neutralizing clones for further testing.

Testing Shortlist of Neutralizing Clones

Neutralizing antibodies identified with both the FLT3L-DC screen and the NFS-60 screen were: 1B11, 1C7, 2F6, 3A3, 3B2, 3B3, 3G5, 9B7, 10B9, 1A1, 3G10, 6F5,7H6, 10G1, 6F3, 7F8, and 8H12. These antibodies were named based on the original screening plate (1-10) and corresponding well identifier (A-H; 1-12) from example 2 above. For example, clone 1B11 corresponds to the clone in plate #1 well B11.

Clones 1B11, 1C7, 2F6, 3A3, 3B2, 3B3, 3G5, 9B7, 10B9, 1A1, 3G10, 6F5,7H6, 10G1, 6F3, 7F8, and 8H12 were tested in triplicate for their ability to neutralize the proliferation of NFS-60 cells cultured with 0.125 ng/mL or 0.625 ng/mL human G-CSF.

Figure 2:
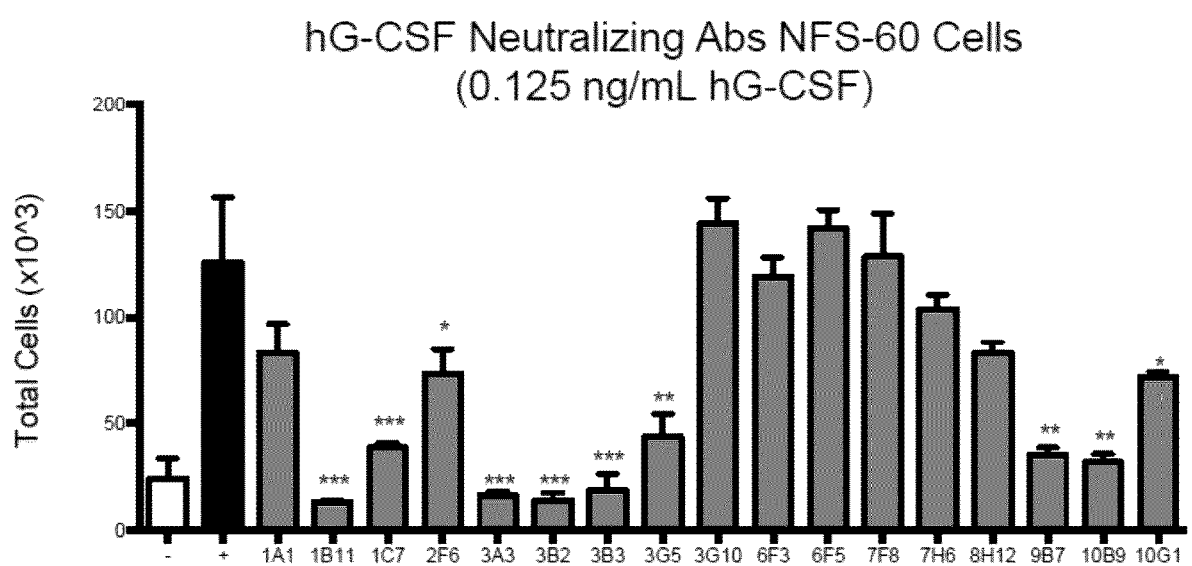

FIG. 2 shows the neutralizing activity of the antibodies using 0.125 ng/mL of human G-CSF. In this study, clone 1B11, 1C7, 2F6, 3A3, 3B2, 3B3, 3G5, 9B7, 10B9, and 10G1 all significantly reduced the proliferation of NFS60 cells. * p<0.05  p<0.01 * p<0.001 **** p<0.0001.

Figure 3:
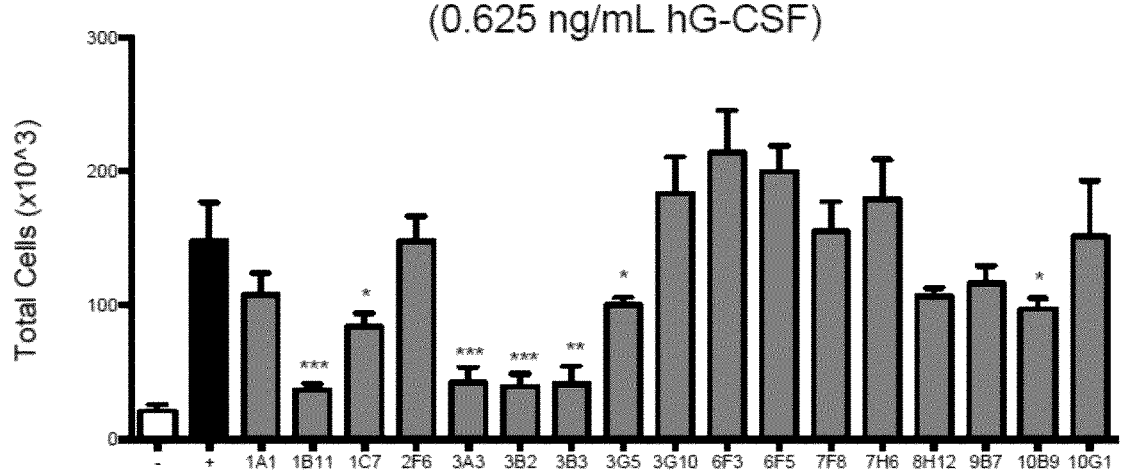

FIG. 3 demonstrates that clones 1B11, 3A3, 3B2, 3B3, 1C7, 3G5 and 10B9 neutralize a high concentration of human G-CSF (0.625 ng/mL). * p<0.05  p<0.01 * p<0.001 **** p<0.0001.

Antibodies 1B11, 1C7, 2F6, 3A3, 3B2, 3B3, 3G5, 9B7, 10B9, and 10G1 were identified as inhibiting human G-CSF dependent NFS-60 proliferation. (FIGS. 2 and 3). Clones 1B11, 3A3, 3B2, and 3B3 had the most significant reduction of NFS-60 proliferation in the presence of the higher concentration of G-CSF (0.625 ng/mL).

Minimal Activity of Anti-Human G-CSF Clones Against Mouse G-CSF

Clones 1B11, 1C7, 2F6, 3A3, 3B2, 3B3, 3G5, 9B7, 10B9, 1A1, 3G10, 6F5, 7H6, 10G1, 6F3, 7F8, and 8H12 were retested in triplicate for their ability to neutralize the proliferation of NFS-60 cells cultured with 0.125 ng/mL human or mouse G-CSF in order to test for cross-reactivity.

Figure 4:
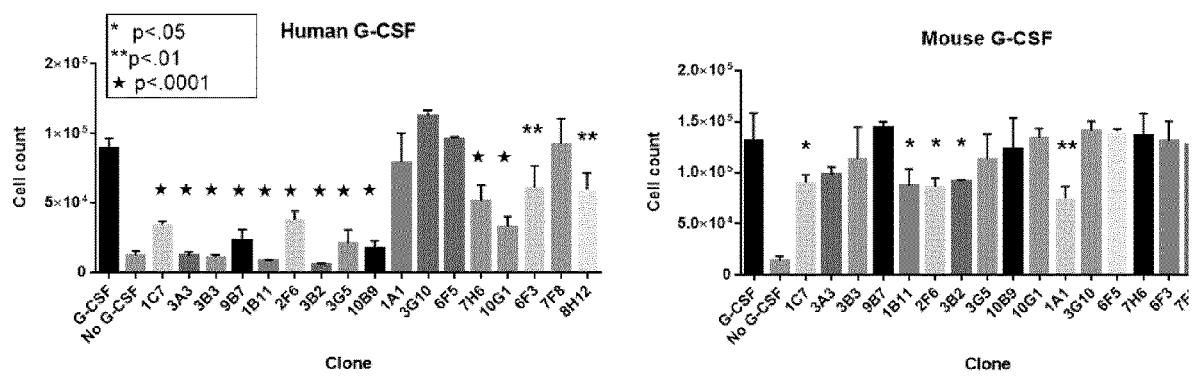

FIG. 4 shows that many of the clones that neutralized human G-CSF induced proliferation (left panel) had little or no activity against mouse G-CSF (right panel). Although some of the clones did appear to neutralize mouse G-CSF, the reduction in proliferation of the NFS-60 cells was marginal compared to the activity seen with human G-CSF (left panel).

Example 4: Subcloning and Neutralizing Activity

Nine of the neutralizing clones: 2F6, 3G5, 10B9, 9B7, 10G1, 1B11, 3A3, 3B2 and 3B3 were chosen for further development and subcloning based on their highly significant neutralization of human G-CSF (FIGS. 3 and 4).

Subcloning was performed by ImmunoPrecise Antibodies Ltd. and two stable high antibody producing subclones of each clone were delivered.

G-CSF Neutralizing Activity of Subclones

The subclones (2F6.1 and 0.2, 3G5.1 and 0.2, 10B9.1 and 0.2, 9B7. 1 and 0.2, 10G1.1 and 0.2, 1B11.2, and 3B3.2) were tested for their ability to neutralize either unglycosylated (*E. coli* produced, Genscript) or glycosylated (CHO produced, Genscript) human G-CSF using the NFS-60 assay.

Figures 5, 6:
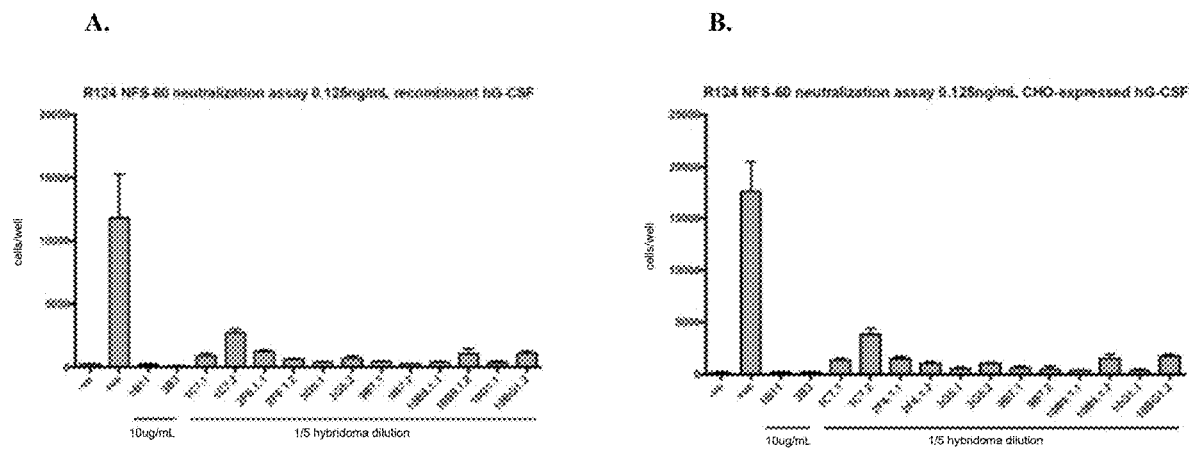

FIG. 5 shows that all of the subclones can neutralize the bioactivity of either glycosylated or unglycosylated human G-CSF.

$2.5 \times 10^3$ NFS-60 cells were cultured in complete DMEM or RPMI media in the presence of 0.125 ng/mL of unglycosylated (left panel; FIG. 5A) or glycosylated (right panel; FIG. 5B) human G-CSF (Genscript) in the presence of 20% anti-G-CSF antibody supernatant (clones 2F6.1 and 2F6.2, 3G5.1 and 3G5.2, 10B9.1 and 10B9.2, 9B7. 1 and 9B7.2, 10G1.1 and 10G1.2) or 10 µg/mL of purified antibody (clones 1B11.2 and 3B3.2) for 6 days. On day 6 the cells were counted using the MACSQuant® and compared to NFS-60 cells grown in the presence (positive control) or absence of G-CSF (negative control).

The subclones (1B11.2, 3A3.2, 3B2.2, and 3B3.2) were chosen as the lead candidates based on their consistent ability to neutralize the bioactivity of human G-CSF. tested for their ability to neutralize G-CSF induced NFS-60 cell proliferation in a dose dependent manner.

FIG. 6 shows that 1B11.2 (FIG. 6A), 3A3.2 (FIG. 6B), 3B2.2 (FIG. 6C), and 3B3.2 (FIG. 6D) all neutralize human G-CSF bioactivity in a dose-dependent manner.

$2.5 \times 10^3$ NFS-60 cells were cultured in complete DMEM or RPMI media in the presence of human G-CSF (0.125 ng/mL) and various concentrations of supernatants from the subclones. All tests were done in triplicate and data represents the mean+/−SD.

Example 5: Sequences

Clones 1B11, 3A3, 3B2, and 3B3, were sequenced by Genscript. Total RNA was extracted from frozen hybridoma cells and cDNA was synthesized from the RNA. PCR was then performed to amplify the variable regions (heavy and light chains) of the antibody, which were then cloned into a standard cloning vector separately and sequenced.

Clones 1B11 and 3A3 were found to have identical sequences and were determined to be the same antibody.

Clones 3B2 and 3B3 were found to have identical sequences and were determined to be the same antibody.

```
SEQUENCE LISTING
1B11
Heavy chain: Amino acids sequence (138 AA)
1B1 VH CDR1
                                         (SEQ ID NO: 1)
IYTMH IB1 VH CDR2
                                         (SEQ ID NO: 2)
YINPSIGYANYNQKFRD

1B1 VH CDR3
                                         (SEQ ID NO: 3)
GGYGDSLFAY

Light chain: Amino acids sequence (132 AA)
1B1 VL CDR1
                                         (SEQ ID NO: 4)
RSSKSLLHSNGITYLY

1B1 VL CDR2
                                         (SEQ ID NO: 5)
QMSNLAS

1B1 VL CDR3
                                         (SEQ ID NO: 6)
AQNLELPYT

1B11 VH
                                         (SEQ ID NO: 7)
QVHLQQSGAELARPGASVKMSCKASGYTFPIYTMH

WIKQRPGQGLEWIGYINPSIGYANYNQKFRDKATL

TADKSSSTAYMQLSSLTSEDSAVYYCARGGYGDSL

FAYWGQGTLVTVSA

1B11 VL
                                         (SEQ ID NO: 8)
DIVMTQAAFSNPVTLGTSASISCRSSKSLLHSNGI

TYLYWYLQKPGQSPQLLIYQMSNLASGVPDRFSSS

GSGTDFTLRISRVEAEDVGVYYCAQNLELPYTFGG

GTKLEIK
```

3B3

Heavy chain: Amino acids sequence (137 AA)

3B3 VH CDR1
(SEQ ID NO: 9)
PYTMH

3B3 VH CDR2
(SEQ ID NO: 10)
YINPSINYTNYNQKFKD

3B3 VH CDR3
(SEQ ID NO: 11)
RGSYGNFDY

Light chain: Amino acids sequence (132 AA)

3B3 VL CDR1
(SEQ ID NO: 12)
RSNKSLLHSNGITYLY

3B3 VL CDR1
(SEQ ID NO: 13)
QMSNLAS

3B3 VL CDR1
(SEQ ID NO: 14)
AQNLELPLT

3B3 VH
(SEQ ID NO: 15)
QVQLQQSGAELARPGASVKMSCKASGYTFTPYTMH
WVKQRPGQDLEWIGYINPSINYTNYNQKFKDKATL
TADKSSSTAYMQLSSLTSEDSAVYFCARRGSYGNF
DYWGQGTTLTVSS

3B3 VL
(SEQ ID NO: 16)
DIVMTQAAFSNPVTLGTSASISCRSNKSLLHSNGI
TYLYWYLQKPGQSPQLLIYQMSNLASGVPDRFSSS
GSGTDFTLRISRVEAEDVGVYYCAQNLELPLTFGA
GTKLELK

1B11 NUCLEIC ACID SEQUENCES
1B11 Variable heavy chain:
(SEQ ID NO: 17)
CAGGTCCACCTGCAGCAGTCTGGGGCTGAACTGGC

AAGACCTGGGGCCTCAGTGAAGATGTCCTGCAAGG

CTTCTGGCTACACCTTTCCTATCTACACGATGCAC

TGGATAAAACAGAGGCCTGGACAGGGTCTGGAATG

GATTGGATACATTAATCCTAGCATTGGTTATGCTA

ATTACAATCAGAAGTTCAGGGACAAGGCCACATTG

ACTGCAGACAAATCCTCCAGCACAGCCTACATGCA

ACTGAGCAGCCTGACATCTGAGGACTCTGCAGTCT

ATTACTGTGCAAGAGGGGGTATGGTGACTCCCTC

TTTGCTTACTGGGGCCAAGGGACTCTGGTCACTGT

CTCTGCA

1B11 Variable light chain:
(SEQ ID NO: 18)
GATATTGTGATGACGCAGGCTGCATTCTCCAATCC

AGTCACTCTTGGAACATCAGCTTCCATCTCCTGCA

GGTCTAGTAAGAGTCTCCTACATAGTAATGGCATC

ACTTATTTGTATTGGTATCTGCAGAAGCCAGGCCA

GTCTCCTCAGCTCCTGATTTATCAGATGTCCAACC

TTGCCTCAGGAGTCCCAGACAGGTTCAGTAGCAGT

GGGTCAGGAACTGATTTCACACTGAGAATCAGCAG

AGTGGAGGCTGAGGATGTGGGTGTTTATTACTGTG

CTCAAAATCTAGAACTTCCGTACACGTTCGGAGGG

GGGACCAAGCTGGAAATAAAA

3B3 NUCLEIC ACID SEQUENCES
3B3 Variable heavy chain:
(SEQ ID NO: 19)
CAGGTCCAGCTGCAGCAGTCTGGGGCTGAACTGGC

AAGACCTGGGGCCTCAGTGAAGATGTCCTGCAAGG

CTTCTGGCTACACCTTTACTCCCTACACGATGCAC

TGGGTGAAACAGAGGCCTGGACAGGATCTGGAATG

GATTGGATACATTAATCCTAGCATTAATTATACTA

ATTACAATCAGAAGTTCAAGGACAAGGCCACATTG

ACTGCAGACAAATCCTCCAGCACAGCCTATATGCA

ACTGAGCAGCCTGACATCTGAGGACTCTGCAGTCT

ATTTCTGTGCAAGAAGAGGGTCTTATGGTAACTTT

GACTACTGGGGCCAAGGCACCACTCTCACAGTCTC

CTCA

3B3 Variable light chain:
(SEQ ID NO: 20)
GATATTGTGATGACGCAGGCTGCATTCTCCAATCC

AGTCACTCTTGGAACATCAGCTTCCATCTCCTGCA

GGTCTAATAAGAGTCTCCTACATAGTAATGGCATC

ACTTATTTGTATTGGTATCTGCAGAAGCCAGGCCA

GTCTCCTCAGCTCCTGATTTATCAGATGTCCAACC

TTGCCTCAGGAGTCCCAGACAGGTTCAGTAGCAGT

GGGTCAGGAACTGATTTCACACTGAGAATCAGCAG

AGTGGAGGCTGAGGATGTGGGTGTTTATTACTGTG

CTCAAAATCTAGAACTTCCGCTCACGTTCGGTGCT

GGGACCAAGCTGGAGCTGAAA

SEQ ID NO: 21
His- His- His- His- His- His

SEQ ID NO: 22
(GGGGS)3

Example 6: Comparison of Neutralizing Activity of 3B3 and 1B11

$2.5 \times 10^3$ NFS-60 cells were cultured in complete DMEM or RPMI media in the presence of human G-CSF (0.125 ng/mL) and various concentrations of purified antibody for 6 days. On day 6 NFS-60 cells were counted using the MACSQuant®. Each antibody concentration was performed in triplicate and data represents the mean+/−SD.

Figure 7:
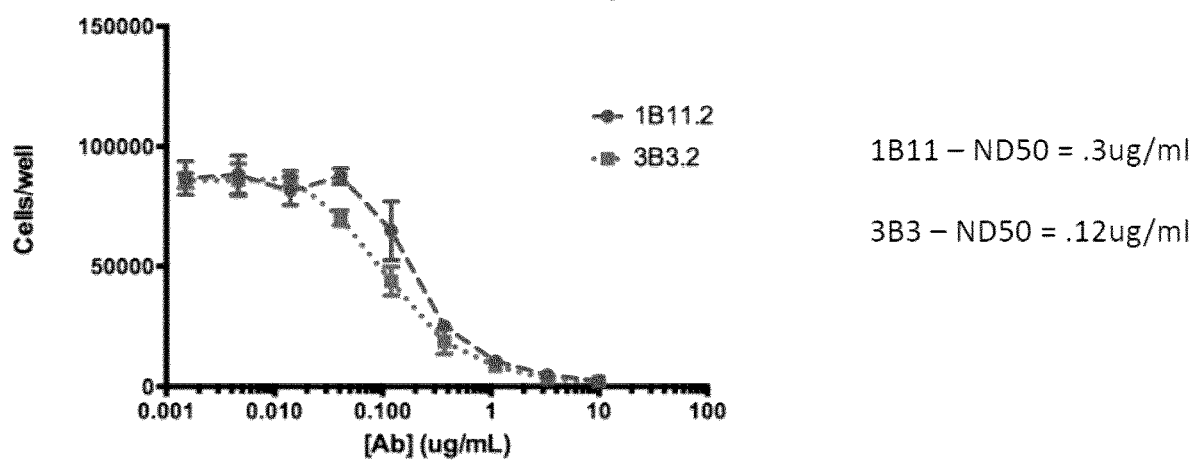

FIG. 7 is a dose response curve showing the proliferation of NFS-60 cells to human G-CSF (0.125 ng/mL) in the presence of various concentrations of neutralizing antibody.

Clone 3B3 was found to be about 2-3 times more effective at neutralizing the bioactivity of G-CSF compared to clone 1B11 as shown in FIG. 7.

$2.5 \times 10^3$ NFS-60 cells were cultured in complete DMEM or RPMI media in the presence of 0.125 ng/mL human G-CSF (Genscript®) in the presence of various dilutions of purified anti-G-CSF antibody clone 1B11 or 3B3 for 6 days. On day 6 the cells were counted using the MACSQuant®. Data shows the mean+/−SD for each antibody concentration.

Example 7: Affinity of Anti-G-CSF Antibody Clones

Affinities of clones 2F6, 1B11, 3G5, 10B9, 9B7, 10G1, and 3B3 were measured by SPR. The work was carried out at the National Research Council of Canada (Montreal, Quebec).

2.5% supernatants (except variants 1B11.2 and 10B9.1.2 used 4%) were captured on an anti-mouse Fc antibody, flowed with a 30, 10, 3.33, 1.11, and 0.37 nM concentration series of human G-CSF with buffer blank. Association (ka) and dissociation (kd) rates were measured using a BioRad ProteOn™ instrument. Affinity ($K_D$) was calculated as ka/kd.

TABLE 1 shows the affinities of the various anti-G-CSF clones.

| Clone ID | Injection #1 | | | | Injection #2 | | | | KD (M) Average |
|---|---|---|---|---|---|---|---|---|---|
| | ka 1/Ms | kd 1/s | KD M | Rmax RU | ka 1/Ms | kd 1/s | KD (M) | Rmax RU | |
| 2F6 | 7.75E+05 | 8.14E−04 | 1.05E−09 | 127.41 | 7.66E+05 | 8.10E−04 | 1.06E−09 | 121.08 | 1.1E−09 |
| 1B11 | 7.77E+05 | 5.15E−05 | 6.63E−11 | 67.58 | 7.58E+05 | 4.72E−05 | 6.22E−11 | 70.23 | 6.4E−11 |
| 3G5 | 2.16E+05 | 3.49E−04 | 1.61E−09 | 167.61 | 2.42E+05 | 3.38E−04 | 1.40E−09 | 146.37 | 1.5E−09 |
| 10B9 | 7.14E+05 | 1.05E−04 | 1.47E−10 | 56.45 | 5.75E+05 | 6.06E−05 | 1.05E−10 | 58.99 | 1.3E−10 |
| 9B7 | 6.39E+05 | 2.67E−04 | 4.18E−10 | 99.94 | 6.10E+05 | 2.77E−04 | 4.55E−10 | 111.9 | 4.4E−10 |
| 10G1 | 1.30E+06 | 5.73E−04 | 4.40E−10 | 87.83 | 1.22E+06 | 5.50E−04 | 4.52E−10 | 91.08 | 4.5E−10 |
| 3B3 | 9.14E+05 | 3.01E−04 | 3.29E−10 | 113.76 | 9.76E+05 | 2.86E−04 | 2.93E−10 | 113.91 | 3.1E−10 |

The affinities of the clones ranged from $1.5 \times 10^{-9}$ M (3G5) down to $6.4 \times 10^{-11}$ M (1B11). Clone 1B11 was the highest affinity clone (64 pM) and clone 3B3 (310 pM) demonstrated the best binding kinetics.

Figure 8:
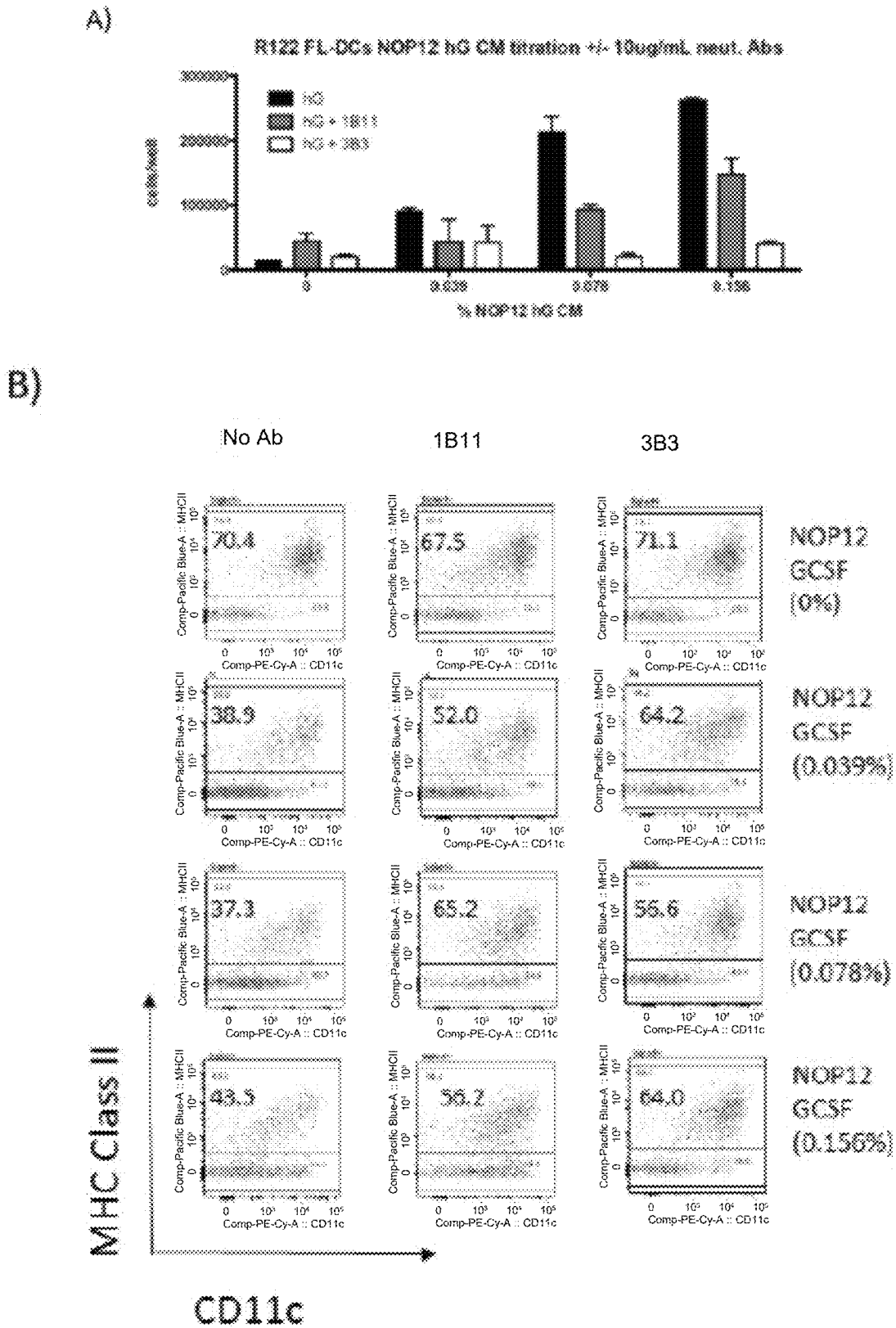

Example 8: Anti-G-CSF Antibody Clones 1B11 and 3B3 Reverse the Negative Effects of Human G-CSF on Dendritic Cell Development FIG. 8 shows that anti-G-CSF clones 1B11 and 3B3 can reverse the effects of mammary tumor derived G-CSF on the development of FLT3L induced dendritic cells in vitro.

The gene for mouse G-CSF was knocked out of the mouse mammary tumor cell line NOP12 which naturally produces mouse G-CSF. Subsequently the NOP12 cells were transfected with a plasmid encoding human G-CSF (SinoBiological) under the CMV promoter. Cells were selected for stable integration of the plasmid using hygromycin resistance. Culture media from NOP12 human G-CSF (NOP12hGCSF) clones was added at various concentrations to bone marrow cultures containing $10^6$ cells/mL and FLT3L (200 ng/mL). Anti-G-CSF antibodies 1B11 or 3B3 were added at 10 µg/mL. The cultures were harvested and counted on day 10 followed by FACS analysis for MHC Class II and CD11c.

FIG. 8A shows the cell counts for the cultures and demonstrates that the addition of supernatant from NOP12hGCSF cells without any blocking antibodies increases the cell counts in the cultures. The addition of either 1B11 or 3B3 significantly reduces the effects of the NOP12hGCSF supernatant. In addition, the neutralizing clones 1B11 and 3B3 also increase the frequency of mature dendritic cells in the cultures as measured by an increased frequency of CD11c+MHC II+ cells (FIG. 8B).

Overall, the results demonstrate that neutralizing G-CSF antibodies can overcome the effects tumor derived G-CSF has on FLT3L induced dendritic cell development.

In addition to looking at the effects of tumor derived G-CSF on FLT3L induced dendritic cell cultures, we also looked at whether it had any effect on GM-CSF induced DC cultures.

Figure 9:
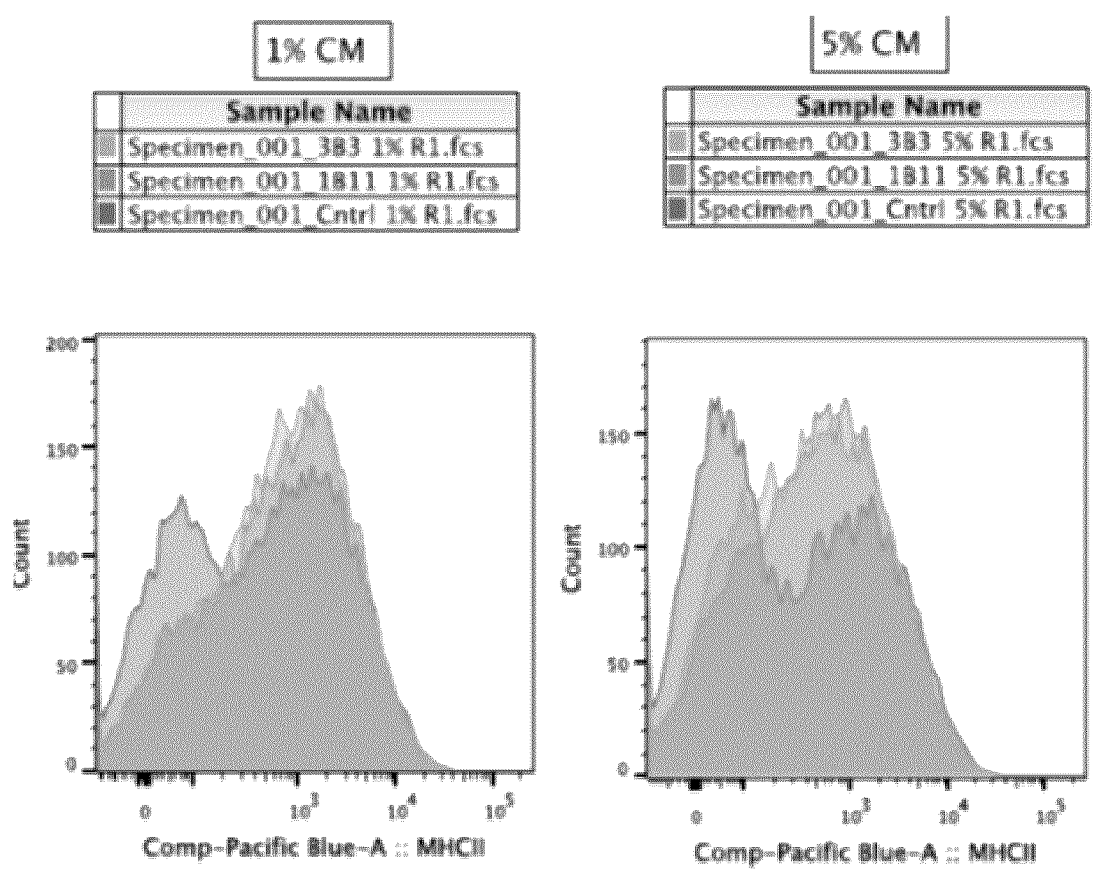

FIG. 9 shows that blocking G-CSF with clones 1B11 or 3B3 can overcome the effect of G-CSF from NOP12hGCSF cells on GM-CSF induced dendritic cell development as measured by MHC Class II expression on the cells.

FIG. 9. Bone marrow cells were plated ($2 \times 10^5$ cells/mL) in non-TC treated petri dishes (10 mL) or 24-well ultralow attachment plates (in 1 mL) with supernatant from 293T cells transfected with G-CSF (1/1000). Supernatant from NOP12Hgcsf cells was added at the start of the culture (1 or 5%) and antibodies against human G-CSF (1B11 or 3B3) were also added at the same time (10 µg/mL). On day 3 a half volume of fresh media was added to the culture. On day 6, a half volume of media was removed and add a half volume of fresh media was added. On day 8, a half volume of media was removed and add a half volume of fresh media was added. Cells were harvested and stained for FACS analysis on day 9 or 10.

Figure 10:
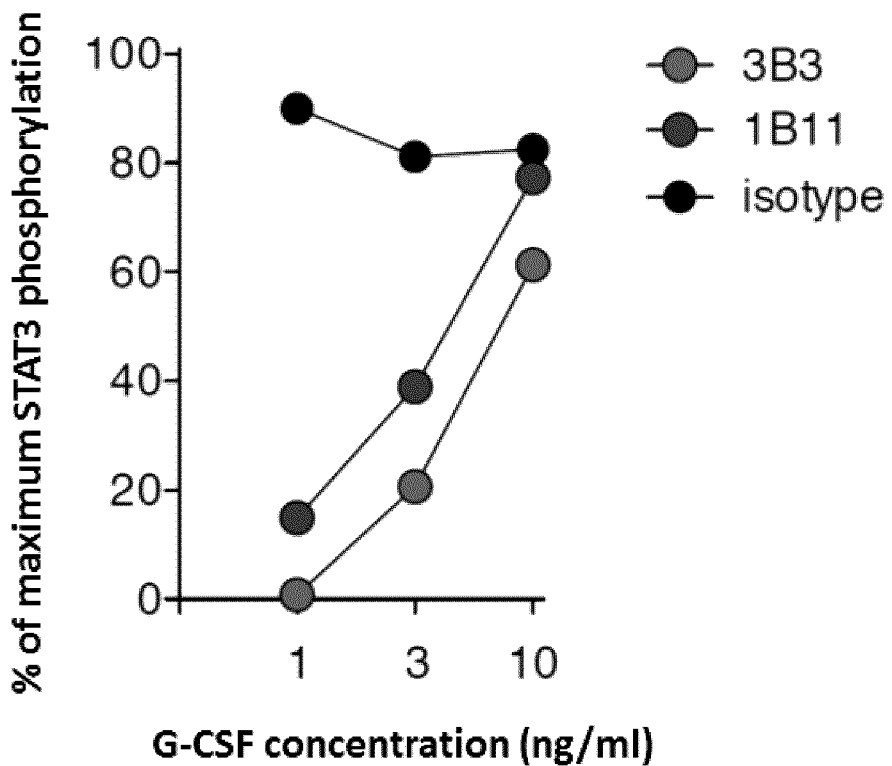

Example 9: Anti-G-CSF Antibody Clones 1B11 and 3B3 Block G-CSF Induced STAT3 Activation in Human Neutrophils FIG. 10 shows that anti-G-CSF clones 1B11 and 3B3 both block STAT3 activation in response to G-CSF stimulation in purified human neutrophils.

Anti-G-CSF clones 1B11 and 3B3 block G-CSF signaling in primary human neutrophils. Various concentrations of human G-CSF (Genscript) were preincubated with 10 µg/mL of purified antibody clone 1B11, 3B3, or an isotype control. After 30 mins, the G-CSF/antibody mixture was added to a plate containing $5 \times 10^5$ purified human neutrophils per well. The plate was incubated for 20 mins after which the cells were immediately fixed and stained for intracellular phosphorylated Stat3 (P-Tyr 705) according to the manufacturers protocol (BD Biosciences). Neutrophils cultured without cytokine and without antibody served as negative and positive controls respectively. Percent maximum Stat3 phosphorylation was calculated for each sample as [MFI (mean fluorescence intensity) experimental sample]/[MFI of the positive control]×100%. 3B3 (bottom set of circles); 1B11 (middle set of circles) and isotype control (top set of circles).

Figure 11A:
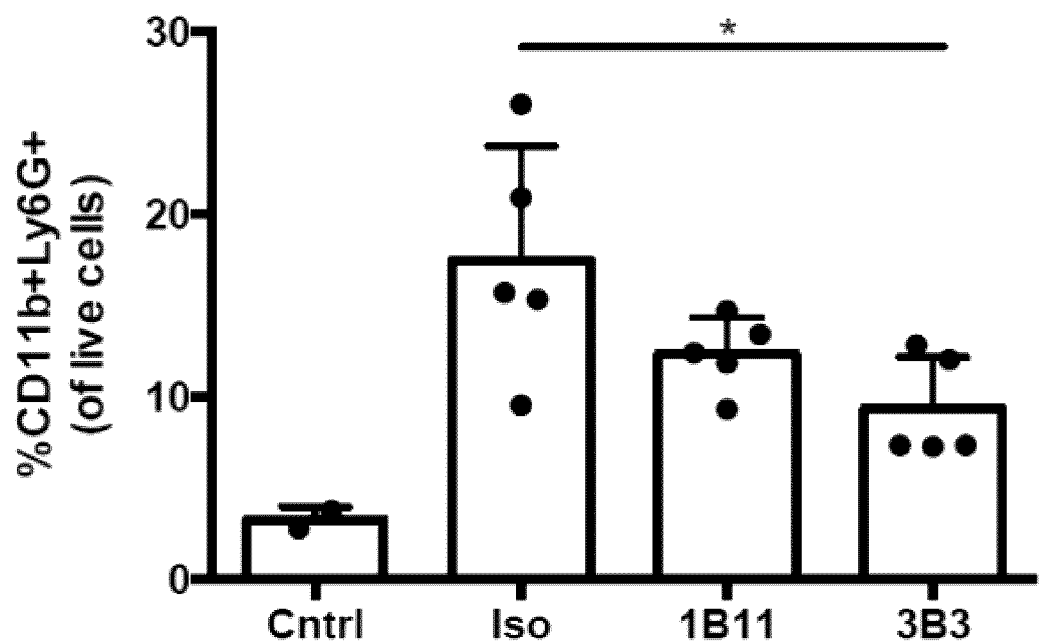
Figure 11B:
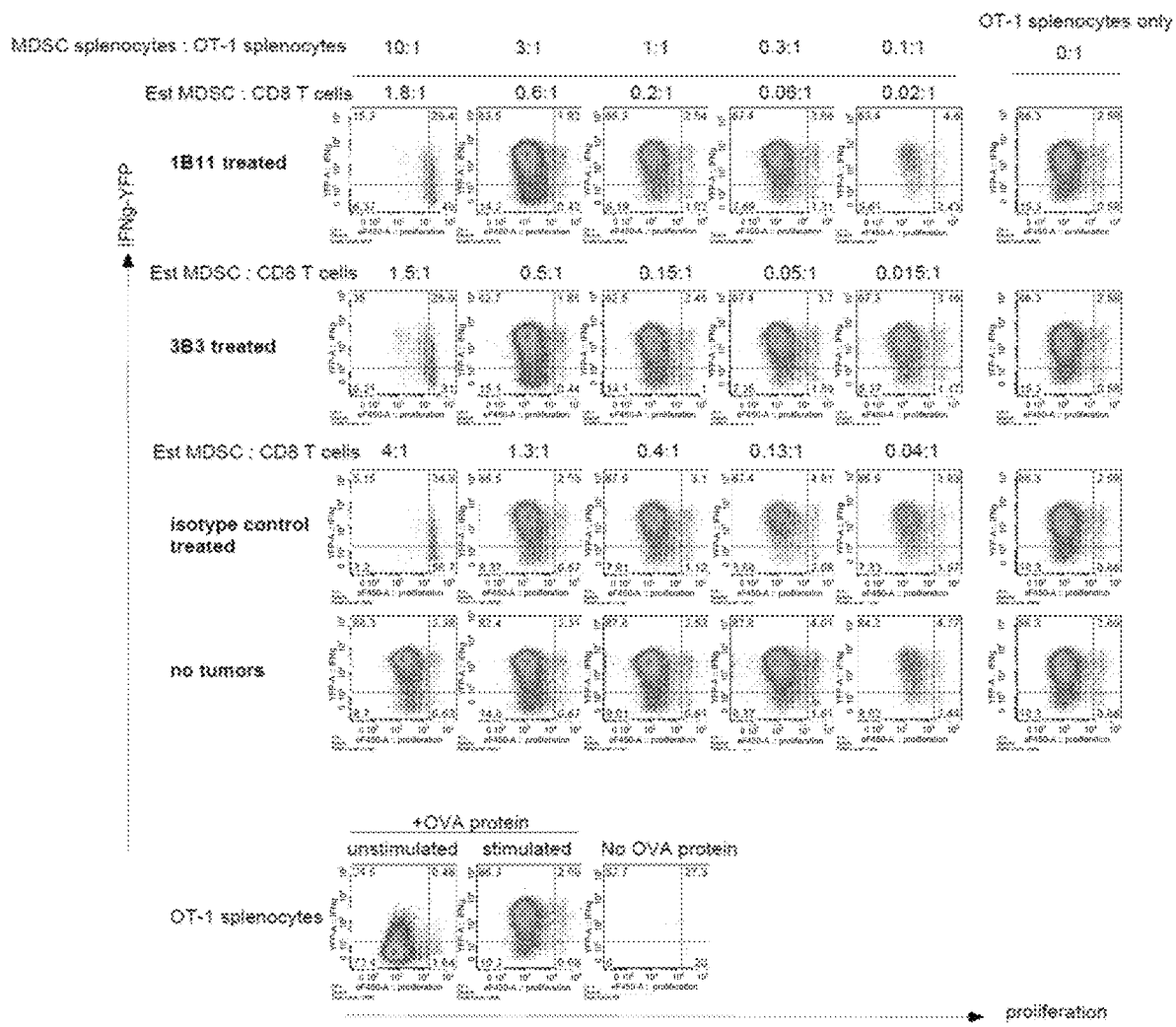

Example 10: Neutralization of In Vivo Tumor G-CSF Production Reduces the Frequency and T Cell Suppressive Ability of MDSCs FIG. 11 shows that anti-G-CSF clones 1B11 and 3B3 reduce the frequency and T cell suppressive activity of MDSCs in the spleens of mice inoculated with human G-CSF expressing MC38 tumors.

C57Bl/6 mice were inoculated with 1×10$^6$ MC38 colon carcinoma cells engineered to express human G-CSF. After 7 days, animals were treated 3 times per week with 200 µg of anti-GCSF clone 1B11, or 3B3 or an isotype control antibody. A) On day 25 the animals were euthanized and the spleens were removed and analyzed for the presence of CD11b+Ly6G+ cells (MDSCs) by flow cytometry. B) Spleens from tumor bearing mice were used as a source of suppressor cells (MDSCs) and added at various ratios to OT-I TCR transgenic splenocytes labeled with a proliferation dye. Whole OVA (200 µg/mL) was added to the cultures as a source of antigen. The OT-I cells also expressed YFP under control of the IFN-gamma promoter which allows one to detect IFN-gamma production based on YFP expression. On day 4, the cells were stimulated with PMA (50 ng/mL) and analyzed by flow cytometry for proliferation and IFN-gamma production. OT-I splenocytes cultured with OVA alone in the absence of MDSCs and OT-I splenocytes cultured with non-tumor bearing splenocytes which lack MDSCs (no tumor group) served as positive controls. OT-I splenocytes cultured in the absence of OVA served as a negative control. The numbers in the upper left quadrant represent OT-I T cells which have undergone at least one division and are capable of producing IFN-gamma. There is clear suppression of OT-I proliferation at the 10 to 1 tumor splenocyte to OT-I splenocyte ratio. Splenocytes from 1B11 and 3B3 treated mice have a reduced ability to suppress OT-I proliferation when compared to the isotype control treated group.

Example 11: Generation of Humanized 1B11 Anti-G-CSF Antibody

Using the heavy and light chain polypeptide sequences for clone 1B11, chimeric, hybrid, and humanized antibodies were generated through a combination of the following variable light chain and variable heavy chain sequences and associated constant domains:

```
1B11 chimeric light chain (cL):
                                        (SEQ ID NO: 23)
DIVMTQAAFSNPVTLGTSASISCRSSKSLLHSNGITYLYWYLQKPGQSP

QLLIYQMSNLASGVPDRFSSSGSGTDFTLRISRVEAEDVGVYYCAQNLE

LPYTFGGGTKLEIK

1B11 chimeric heavy chain (cH):
                                        (SEQ ID NO: 24)
QVHLQQSGAELARPGASVKMSCKASGYTFPIYTMHWIKQRPGQGLEWIG

YINPSIGYANYNQKFRDKATLTADKSSSTAYMQLSSLTSEDSAVYYCAR

GGYGDSLFAYWGQGTLVTVSA

1B11 humanized light chain 1 (h1L)
                                        (SEQ ID NO: 25)
DIVMTQSPLSLPVTPGEPASISCRSSKSLLHSNGITYLYWYLQKPGQSP

QLLIYQMSNLASGVPDRFSGSGSGTDFTLKISRVEAEDVGVYYCAQNLE

LPYTFGQGTKLEIK

1B11 humanized light chain 2 (h2L)
                                        (SEQ ID NO: 26)
DIVMTQSPLSLPVTPGEPASISCRSSKSLLHSNGITYLYWYLQKPGQSP

QLLIYQMSNLASGVPDRFSSSGSGTDFTLKISRVEAEDVGVYYCAQNLE

LPYTFGQGTKLEIK

1B11 humanized heavy chain 1 (h1H):
                                        (SEQ ID NO: 27)
QVQLVQSGAEVKKPGASVKVSCKASGYTFPIYTMHWVRQAPGQGLEWMG

YINPSIGYANYNQKFRDRVTITADTSTSTAYMELSSLRSEDTAVYYCAR

GGYGDSLFAYWGQGTLVTVSS

1B11 humanized heavy chain 2 (h2H):
                                        (SEQ ID NO: 28)
QVQLVQSGAEVKKPGASVKVSCKASGYTFPIYTMHWIRQAPGQGLEWIG

YINPSIGYANYNQKFRDRATLTADTSTSTAYMELSSLRSEDTAVYYCAR

GGYGDSLFAYWGQGTLVTVSS

1B11 humanized heavy chain 3 (h3H):
                                        (SEQ ID NO: 29)
QVQLVQSGAEVKKPGASVKVSCKASGYTFPIYTMHWIKQAPGQGLEWIG

YINPSIGYANYNQKFRDRATLTADKSTSTAYMELSSLRSEDTAVYYCAR

GGYGDSLFAYWGQGTLVTVSS

1B11 humanized heavy chain 4 (h4H):
                                        (SEQ ID NO: 30)
QVHLVQSGAEVKKPGASVKVSCKASGYTFPIYTMHWIKQAPGQGLEWIG

YINPSIGYANYNQKFRDKATLTADKSTSTAYMELSSLRSEDTAVYYCAR

GGYGDSLFAYWGQGTLVTVSS
```

In total, 15 clones were produced with the following combinations of heavy and light chains:

| Clone/Antibody Variant | Variable Light/ Variable Heavy |
| --- | --- |
| 1 | cL/cH |
| 2 | cL/h1H |
| 3 | cL/h2H |
| 4 | cL/h3H |
| 5 | cL/h4H |
| 6 | h1L/cH |
| 7 | h1L/h1H |
| 8 | h1L/h2H |
| 9 | h1L/h3H |
| 10 | h1L/h4H |
| 11 | h2L/H1H |
| 12 | h2L/h2H |
| 13 | h2L/h2H |
| 14 | h2L/h3H |
| 15 | h2L/h4H |

CHO-3E7 were transfected with the expression plasmids in serum-freed media to produce each of the 1B11 antibody variants identified above. Relative expression level of the antibodies was compared using polar advantage high-performance liquid chromatography (pA HPLC) and sodium dodecyl sulfate polyacrylamide gel electrophoresis (SDS-PAGE).

The 1B11 antibody variants purified using affinity chromatography is further purified by size exclusion chromatography. The purified anti-G-CSF antibodies are then subject to surface plasmon resonance (SPR) analysis and thermal stability measurements.

The SPR analysis uses an indirect-capture method which involves capturing the purified 1B11 antibody variants and controls onto an appropriate anti-Fc SPR surface, and flowing over top of the captured antibody a concentration series of the antigen and buffer blank for referencing. The indirect-capture method ensures simple Langmuir binding to allow for the determination of the binding kinetics and affinity of each 1B11 antibody variant.

Differential scanning calorimetry (DSC) was also performed on the 1B11 antibody chimeric and humanized variants to assess their thermal stability. DSC is an analytical technique known to persons skilled in the art (see Durowoju et al., J. Vis. Exp. 2017; (121): 55262). DSC measures the molar heat capacity of samples as a function of temperature. For polypeptide, DSC profiles provide information about thermal stability, and, to some extent, provides a structural "fingerprint" that can be used to assess structural conformation. DSC involves using a differential scanning calorimeter that measures the thermal transition temperature (melting temperature; $T_m$) and the energy required to disrupt the interactions stabilizing the tertiary structure (enthalpy; $\Delta H$) of polypeptides. Comparisons are made between formulations as well as production lots, and differences in derived values indicate differences in thermal stability and structural conformation.

FIG. 12 illustrates the binding characteristics for the ant-G-CSF antibody variants from clones 1, 7, 8, 9, 10, 12, 13, 14, and 15 with the $K_{off}$ value ranging from 1.0-1.7 ($10^{-4} \times s^{-1}$) and the thermal stability of these variant antibodies, which ranges from 71° C. to 85° C. FIG. 12 also illustrates the percentage of humanization of V-FR which ranges from 82.1% to 100%. Variant 7 anti-G-CSF antibody is the 100% humanized version of 1B11 IgG1 and variant 12 anti-G-CSF antibody has a single mouse residue retained in the CDR supporting region of 1B11 parental antibody.

FIG. 12 illustrates variant 12 antibody having a 200 pM affinity and an $K_{off}$ rate of $1.1 \times 10^{-4} \times s^{-1}$, and the antibody being thermostable (e.g., having a higher $T_m2$ and $T_m3$ than that of trastuzumab (Herceptin)). Herceptin has a $T_m1$ of 68° C. and $T_m2$ of 80° C. whereas variant 12 has a $T_m1$ of 71° C. and $T_m2$ of 82° C. The data from FIG. 12 also indicates that no aggregates formed when the variant 12 anti-G-CSF antibodies are produced.

Example 12: Neutralization Assays for Humanized 1B11 Antibodies

Neutralization assays were conducted for all 15 1B11 variant antibodies. The results were compared to parental 1B11 antibody. BaF3-hGCSFR cells were incubated with 10 ng/mL hG-CSF and 10 µg/mL humanized 1B11 antibodies for 15 minutes. Cells were subsequently fixed, permeabilized, and stained with anti-phospho-STAT3 antibody (Life Technologies) according to manufacturer's instructions. Samples were then collected via a flow cytometer and STAT3 levels were analyzed using Flowjo software.

Figure 13:
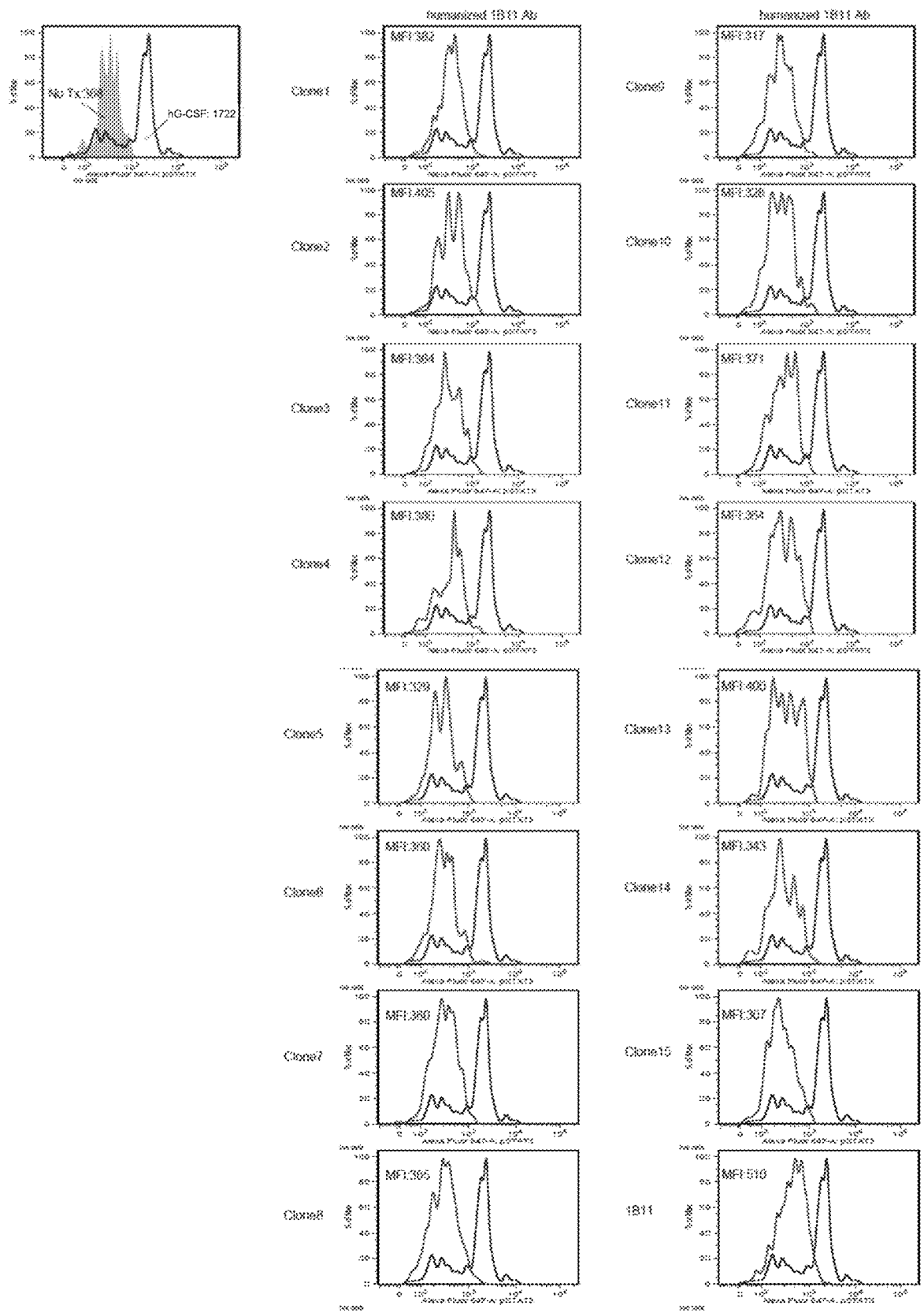
FIG. 13 are flow plots illustrating the blocking of G-CSF dependent STAT3 signaling in vitro by humanized variants of 1B11 antibodies.

FIG. 13 illustrates all 15 variants of 1B11 blocking G-CSF dependent STAT3 signaling in vitro. In the flow plots shown in FIG. 13, the grey shade indicates no treatment control; blue line indicates treatment with hG-CSF treated only; and red line indicates treatment with a humanized 1B11 antibody.

Example 13: Neutralizing Growth of NFS-60 Cells by Variants 7 and 12 Humanized 1B11 Antibodies NFS-60, which are responsive to hG-CSF, cells were used to test the neutralizing ability of variants 7 and 12 humanized 1B11 antibodies, using parental 1B11 antibody as control.

NFS60 cells were grown in the media with 0.125 ng/mL hG-CSF and different concentration (µg/mL) of variant 7 and 12 humanized 1B11 antibodies or parental 1B11 antibody. After 6 days, cells were collected, washed and mixed with a fixed number of counting beads. Subsequently, samples were analyzed on a flow cytometer and cell counts were determined based on the ratio of counting beads to NFS60 cells.

Figure 14:
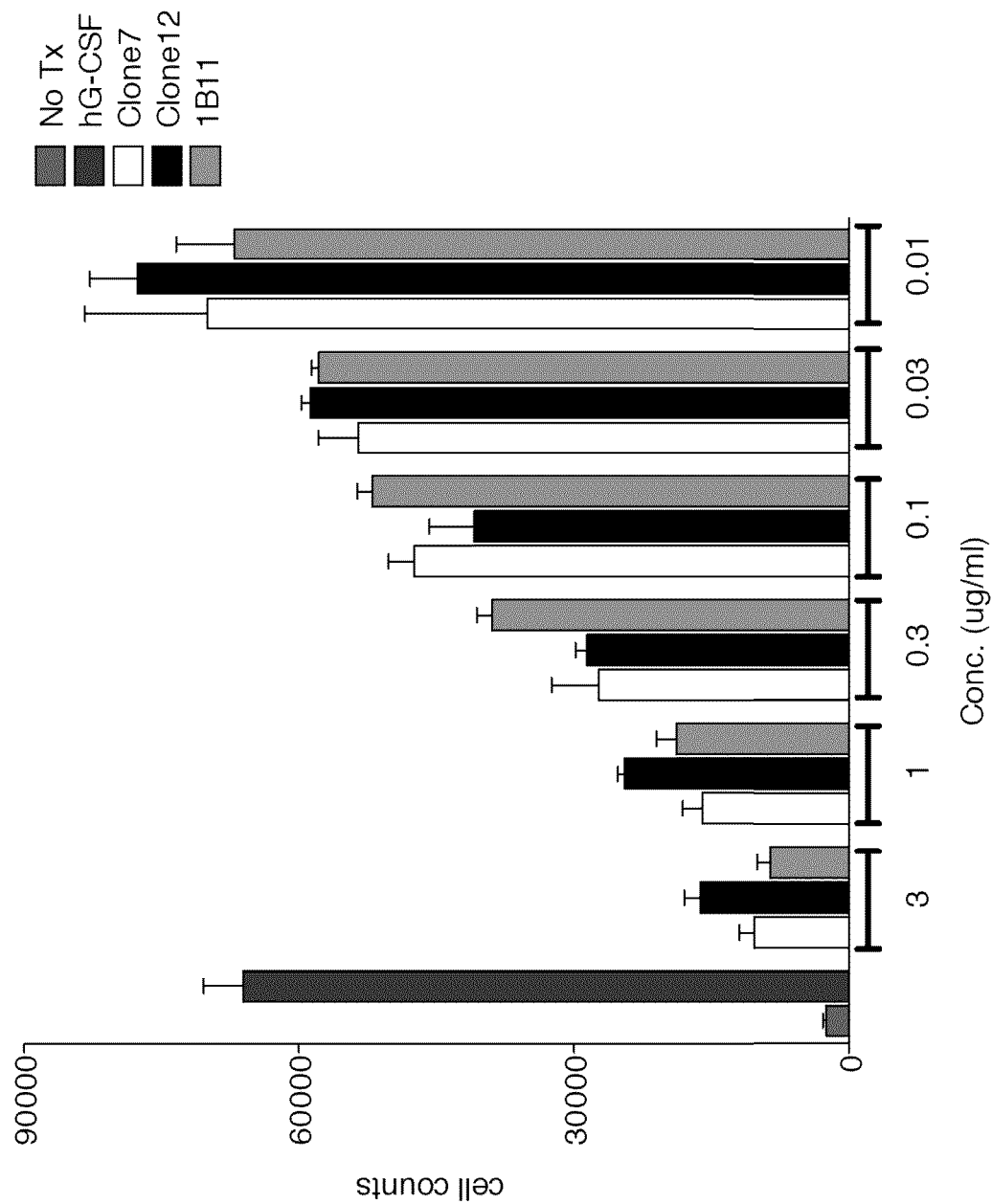
FIG. 14 is a bar graph illustrating the neutralization of G-CSF dependent growth of NFS60 cells by humanized 1B11 variant 7 and 12 antibodies.

FIG. 14 is a bar graph illustrating the cell counts for media with 0.01, 0.3, 0.1, 0.3, 1, and 3 µg/mL of 1B11 antibodies. Cells without treatment and with hG-CSF treatment only were used as control. FIG. 14 illustrates the parental 1B11 antibody and variants 7 and 12 humanized 1B11 antibodies all neutralize G-CSF dependent growth of NFS60 cells in a dose-dependent manner.

Example 14: Neutralization Assays for Variants 7 and 12 Humanized 1B11 Antibodies Neutralization assays were conducted for the variant 7 and 12 humanized 1B11 antibodies. The results were compared to parental 1B11 antibody.

For a first set of experiments (shown in the first three rows of the flow plot in FIG. 15), 10 ng/mL hG-CSF were pre-treated with various concentration (µg/mL) of parental or humanized 1B11 antibodies (i.e., variants 7 or 12) for 30 minutes. The mixture of hG-CSF and the humanized/parental 1B11 antibodies were added to BaF3-hGCSFR cells. The mixture was incubated for 15 minutes. Cells were subsequently fixed, permeabilized and stained with anti-phospho-STAT3 antibody (Life Technologies) according to manufacturer's instructions. Samples were then collected via a flow cytometer and STAT3 levels were analyzed using Flowjo software.

For a second set of experiments (shown in last three rows of the flow plot in FIG. 15), BaF3-hGCSFR cells were incubated with 10 ng/mL hG-CSF and various concentration of parental or humanized 1B11 antibodies for 15 minutes. Cells were subsequently fixed, permeabilized and stained with anti-phospho-STAT3 antibody (Life Technologies) according to manufacturer's instructions. Samples were then collected via a flow cytometer and STAT3 levels were analyzed using Flowjo software.

Figure 15:
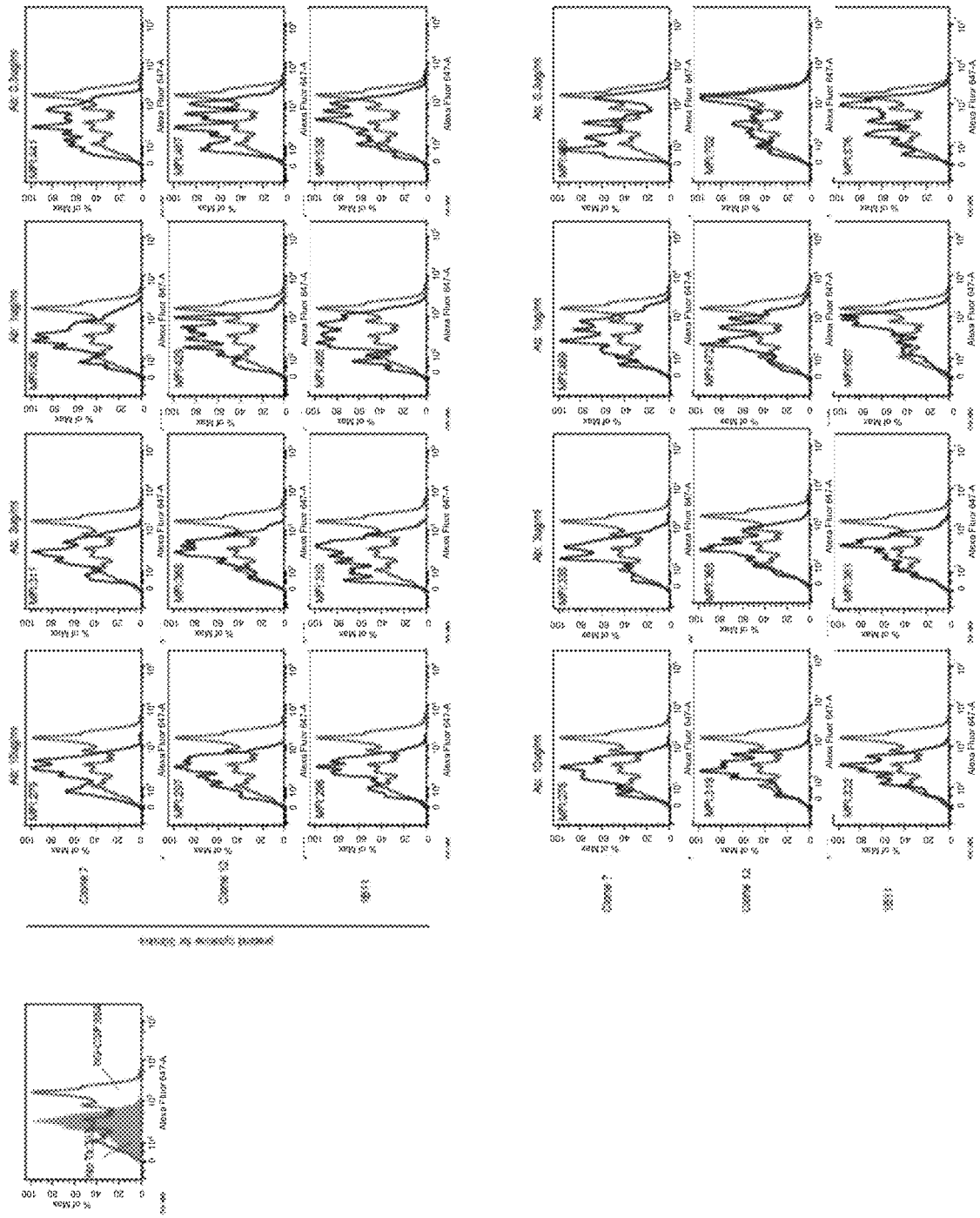
FIG. 15 are flow plots illustrating the neutralization of G-CSF dependent STAT3 activation in a dose-dependent manner by humanized 1B11 variant 7 and 12 antibodies.

In the flow plots in FIG. 15, the grey shade indicates no treatment control; red line indicates treatment with hG-CSF treated only; and blue line indicates treatment with a humanized 1B11 antibody variant or the parental 1B11 antibody.

Example 15: Neutralization Assays for Clone 12 Humanized 1B11 Antibody

Further neutralization assays were conducted for variant 12 humanized 1B11 antibody. For this assay, a single dose of variant 12 humanized 1B11 antibody at 20 mg/kg was injected intraperitoneally into a female 8 week old C57Bl/6 mice (n=3 per group, mean+/−SEM). Clinical grade recombinant human G-CSF (Filagastrim) was injected into the same mice subcutaneously 16 hours after injection of the variant 12 humanized 1B11 antibody. A baseline control mouse was injected with at the same time points and administration routes with phosphate buffered saline (PBS). To measure neutralization activity, blood from the mice was sampled at 1 hour after injection of the G-CSF and stained with antibodies against CD11b and Ly6G (Life Technologies) on ice. Subsequently the cells were washed, fixed, permeabilized, and stained with anti-phospho-STAT3 antibody (Life Technologies) according to manufacturers' instructions. After washing, the samples were mixed with counting beads and analyzed by flow cytometry for inhibition of circulating neutrophil (CD11b+Ly6G+) frequencies and blockade of pSTAT3 signaling activity in neutrophils. Statistical significance was assessed by Student's t-test (* p<0.05, ** p<0.01). The results are shown on FIGS. 16A and 16B, respectively.

As shown in FIGS. 16A and 16B, variant 12 humanized 1B11 antibody reduces G-CSF induced neutrophilia and blocks neutrophil pSTAT3 signaling.

Example 16: Therapy of Preformed Human Breast Cancer Tumors in Human Skin Grafted into SCID Mice The effect of the anti-G-CSF antibodies described herein can be assessed with respect to their anti-cancer effect on preformed human breast cancer tumors grown in human skin grafted into SCID mice.

Briefly, MCF-7 cells ($8 \times 10^6$ cells in 0.1 mL PBS) are transplanted intradermally into human full-thickness skin grafted into SCID mice when the grafts showed no signs of inflammation, contraction or rejection. The mice are left untreated until distinct palpable tumors (3 to 6 mm in diameter in most cases) appear. Mice with distinct tumors are divided into groups for the therapeutic studies. An anti-G-CSF antibody and an isotype-matched control IgG are diluted with sterile PBS containing mouse serum albumin (0.05% final concentration). For the antibody therapy, 1 to 20 mg/kg anti-G-CSF antibody or control IgG is intravenously (i.v.) administered via the tail vein of mice. The administration is given every two to three days.

During the treatment, mice are monitored daily for tumor size and morbidity. Mice are weighed twice a week using an electronic balance (OHAUS™ Model GT210). Tumor size is measured three times a week using an electronic caliper (PRO-MAX 6 inch caliper; Fowler Co., Newton, Mass.) connected to a computer using OPTODEMO™ software (Fowler Co.). The measured tumor diameters are converted to tumor volumes using the following formula: $V = length \times width \times height \times pi/6$. Statistical analysis of the data for the comparison of different groups of mice is carried out using Student's t-test.

Example 17: Mouse Model of Ovarian Cancer

To determine the ability of anti-G-CSF antibodies, or antigen-binding fragments thereof, to treat ovarian cancer, an ovarian cancer cell line can be used in SCID or nude mice.

Briefly, ovarian cancer cells are implanted into SCID or nude mice to generate ovarian tumors. Groups of mice bearing established tumors are treated by intravenous (i.v.) administration of escalating doses (starting at 1.8 mg/kg body weight) of anti-G-CSF antibody or control IgG. The treatment is performed 2 or 3 times per week. A VEGF inhibitor and/or other anticancer agent may be used in a separate test group. The mice are monitored and tumor growth is measured 2 or 3 times per week.

Example 18: Mouse Model of Colorectal Cancer

To determine the ability of anti-G-CSF antibodies, or antigen-binding fragments thereof, to treat colorectal cancer, a colorectal cancer cell line can be used in SCID, nude or immunocompetent mice.

Briefly, colorectal cancer cells are implanted into SCID, nude or immunocompetent mice to generate colorectal tumors. Groups of mice bearing established tumors are treated by i.v. administration of escalating doses (starting at 1.8 mg/kg body weight) of an anti-G-CSF antibody or control IgG. The treatment is performed 2 or 3 times per week. A VEGF inhibitor and/or other anticancer agent may be used in a separate test group. The mice are monitored and tumor growth is measured 2 or 3 times per week. Tumors may be imaged by standard imaging test, including PET and ultrasound. Treated tumors may be explanted to assess intracellular signaling pathways or vascularity by immunohistochemistry.

Example 19: Clinical Trial of Combination Therapy for Colorectal Cancer

This example describes a randomized, blinded, placebo-controlled, multicenter, Phase 2 study designed to provide a preliminary assessment of the safety and efficacy of an anti-G-CSF antibody in patients with colorectal cancer. Approximately about 100-about 800 patients are enrolled, with about 50 to about 400 patients being assigned to a treatment group and about 50 to about 400 patients assigned to a placebo group. The trial will consist of the administration of intravenous repeating doses of an anti-G-CSF antibody at from about 0.1 to about 20 mg/kg or placebo every one, two or three weeks for 6-10 cycles. A VEGF inhibitor and/or other anticancer agent may be used in a separate test group. The time frame of the study is estimated at about 6 months to about 5 years, with continued therapy for responders as indicated at the end of the initial study. Additional outcome measures are as follows:

Primary outcome measure: overall response rate. One goal of the study is to demonstrate an increase progression-free survival by 35% following treatment with an anti-G-CSF antibody.

Secondary outcome measures that can be assessed include overall response rate, duration of response, overall survival, serious and non-serious adverse events. For example, a treatment may prevent progression of the disease (i.e., stasis) or may result in an improvement. Alternately, or in addition, other goals can be measured with respect to one or more of the following: decreased tumor burden, decreased vascularity, reduced side effects, decreased adverse reactions, and/or increased patient compliance.

Example 20: Clinical Trial of Combination Therapy for Ovarian Cancer

This example describes a randomized, blinded, placebo-controlled, multicenter, Phase 2 study designed to provide a preliminary assessment of the safety and efficacy of combining an anti-G-CSF antibody with Doxil® in patients with ovarian cancer. Approximately about 100-about 800 patients are enrolled, with about 50-about 400 patients being assigned to a treatment group and about 50-about 400 patients assigned to a placebo group. The trial will consist of the administration of intravenous repeating doses of an anti-G-CSF antibody at from about 0.1 to about 20 mg/kg or placebo every one, two or four weeks combined with Doxil® at about 5 to about 50 mg/m² administered once every 4 weeks The time frame of the study is estimated at 6 months to about 5 years, with continued therapy for responders as indicated at the end of the initial study. Additional outcome measures are as follows:

Primary outcome measure: progression-free survival. One goal of the study is to demonstrate an increase in progression free survival from about 3-6 months in the Doxil® plus placebo arm to about 4-12 months (or more) in the Doxil® plus an anti-G-CSF antibody arm.

Secondary outcome measures that can be assessed include duration of response, time to tumor progression, overall survival, serious and non-serious adverse events. For example, a treatment may prevent progression of the disease (i.e., stasis) or may result in an improvement. Alternately, or in addition, other goals can be measured with respect to one or more of the following: decreased tumor burden, decreased vascularity, reduced side effects, decreased adverse reactions, and/or increased patient compliance.

Example 21: Clinical Trial of Platinum Based Combination Therapy for Ovarian Cancer This example describes a randomized, blinded, placebo-controlled, multicenter, Phase 2 study designed to provide a preliminary assessment of the safety and efficacy of combining an anti-G-CSF antibody with platinum based chemotherapy in patients with ovarian cancer. Approximately about 100-about 800 patients are enrolled, with from about 50 to about 400 patients being assigned to a treatment group and about 50-about 400 patients assigned to a placebo group. The trial will consist of the administration of intravenous repeating doses of an anti-G-CSF antibody at from about 0.1 to about 20 mg/kg or placebo every one, two or three weeks combined with a platinum based chemotherapy regimen (e.g., carboplatin and paclitaxel) by intravenous infusion with courses repeating throughout the study. The time frame of the study is estimated at about 6 months—about 5 years, with continued therapy for responders as indicated at the end of the initial study. Additional outcome measures are as follows:

Primary outcome measure: progression-free survival. One goal of the study is to demonstrate an increase in progression free survival from about 12-18 months in the topotecan plus placebo arm to about 12-24 months (or more) in platinum-based chemotherapy plus an anti-G-CSF antibody arm.

Secondary outcome measures that can be assessed include duration of response, time to tumor progression, overall survival, serious and non-serious adverse events. For example, a treatment may prevent progression of the disease (i.e., stasis) or may result in an improvement. Alternately, or in addition, other goals can be measured with respect to one or more of the following: decreased tumor burden, decreased vascularity, reduced side effects, decreased adverse reactions, and/or increased patient compliance.

Example 22: Therapy of Human Breast Cancer Tumors in Mice in SCID Mice

The effect of the anti-G-CSF antibodies described herein can be assessed with respect to their anti-cancer effect on preformed human breast cancer tumors grown in human skin grafted into SCID mice.

Briefly, MDA-MB-231 cells (1-2×10⁶ cells in 0.1 mL PBS) are transplanted subcutaneously into the flank of SCID mice. The mice are left untreated until distinct palpable tumors (3 to 6 mm in diameter in most cases) appear. Mice with distinct tumors are divided into groups for the therapeutic studies. An anti-G-CSF antibody and an isotype-matched control IgG are diluted with sterile PBS containing mouse serum albumin (0.05% final concentration). For the antibody therapy, 1 to 20 mg/kg anti-G-CSF antibody or control IgG is intravenously (i.v.) administered via the tail vein of mice or intra-peritoneally (i.p.). The administration is given every two to three days.

During the treatment, mice are monitored daily for tumor size and morbidity. Mice are weighed twice a week using an electronic balance (OHAUS™ Model GT210). Tumor size is measured three times a week using an electronic caliper (PRO-MAX 6 inch caliper; Fowler Co., Newton, Mass.) connected to a computer using OptoDemo™ software (Fowler Co.). The measured tumor diameters are converted to tumor volumes using the following formula: V=length× width×height×pi/6. Statistical analysis of the data for the comparison of different groups of mice is carried out using Student's t-test.

Example 23: Combination Therapy for Skin Cancer

The following study is a clinical trial for an anti-G-CSF antibody in combination with Ipilumamb compared to Ipilumamb in combination with plus placebo in metastatic melanoma patients.

Primary Outcome Measures include, but are not limited to:

Phase 1: Number of patients with adverse events as a measure of Safety and Tolerability. Baseline and outcomes are measured every 3 weeks until discontinuation or death. The estimated timeframe is 29 months from first patient enrolled to last patient discontinued or dead).

Phase 2: Overall survival is measured every 4 weeks until the 50$^{th}$ death occurs, then follow-up is conducted every 3 months for the remaining patients.

Secondary Outcome Measures include, but are not limited to:

Preliminary efficacy as assessed by tumor response. Tumors are assessed at baseline and every nine weeks (3 cycles) thereafter with an estimated timeframe that each patient is on study for 11 months.

Evaluation of progression free survival as measured every 4 weeks until the 50th death occurs, then follow-up is measured every 3 months.

Group I is to be administered an anti-G-CSF antibody twice daily in combination with 300 mg ipilimumab.

Group II is to be administered a placebo twice daily in combination with 300 mg ipilimumab.

Subjects to be treated are 18 years and older.

Inclusion Criteria:

Male or female subjects, aged 18 years or older with unresectable or metastatic melanoma.

A life expectancy of >12 weeks.

Laboratory ranges and medical criteria met, as defined within the protocol.

Subject may have received more than 1 prior regimen of systematic treatment for unresectable or metastatic melanoma.

For Phase 2 period of the study only, Subjects must have archival tumor tissue available and collected with the prior 6 months or accessible disease for pre-treatment, study biopsy.

Exclusion Criteria:

Pregnant or nursing women.

Current investigational trial participation with another investigational product or subjects who have received any anticancer medications within 21 days prior to screening (6 weeks for mitomycin-C or nitrosoureas.)

Subjects receiving monoamine oxidase inhibitors (MAOIs); subjects who have ever had Serotonin Syndrome after receiving one or more serotonergic drugs.

Subjects who have received prior immune checkpoint inhibitors (e.g., anti-CTLA-4, anti-PD-1, anti-PD-L1 and others) who have had Grade 3 or 4 hepatotoxicity, immune colitis requiring infliximab, endocrine toxicity not controlled by replacement, any other Grade 4 immune adverse events (AEs) or ocular toxicity Subjects with protocol-specified active autoimmune process except vitiligo or thyroiditis.

Subjects with concurrent conditions that would jeopardize the safety of the safety of the subject or compliance with the protocol.

Example 24: Breast Cancer and Ipilimumab

The following study is a clinical trial for an anti-G-CSF antibody when given together with ipilimumab in treating patients with solid tumors that have spread to other places in the body and usually cannot be cured or controlled with treatment (metastatic) or that cannot be removed by surgery (unresectable) or human epidermal growth factor receptor 2 (HER2)-negative breast cancer that has spread from where it started to nearby tissue or lymph nodes or other parts of the body.

Conditions to be treated include Breast Adenocarcinoma, HER2/Neu Negative, Invasive Breast Carcinoma, Recurrent Breast Carcinoma, Solid Neoplasm, Stage IIIA Breast Cancer, Stage IIIB Breast Cancer, Stage IIIC Breast Cancer and Stage IV Breast Cancer.

Primary Outcome Measures include, but are not limited to: incidence of adverse events of anti-G-CSF antibody in combination with ipilimumab per National Cancer Institute Common Terminology Criteria for Adverse Events (CTCAE) version (v)4.0 are assessed for up to 100 days after last dose of nivolumab.

Safety and tolerability are analyzed through the incidence of adverse events, serious adverse events, and specific laboratory abnormalities (worst grade) in each arm. Toxicities are tabulated by type and grade for all doses and presented using frequencies and percentages based on the CTCAE v4.0. The proportion of dose-limiting toxicities at each dose level are reported with exact 95% confidence intervals.

Secondary Outcome Measures: include, but are not limited to: changes in ratio of Teff to Treg in tumor biopsies, measured by IHC staining of paraffin embedded tumor specimens at baseline to up to 2 weeks post-anti-G-CSF antibody. Changes are treated as a continuous variable and summarized with descriptive statistics. Changes are be graphically depicted using exploratory plots (e.g., bar plots, boxplots, etc.) and means are estimated with 95% confidence intervals. A paired t-tests or nonparametric Wilcoxon signed-rank test is used to determine whether or not the data shows evidence of changes from baseline.

The disease control rate is defined as the percentage of patients who have achieved CR, PR or stable disease (SD) among all response evaluable patients based on RECIST v1.1 and irRC (expansion cohort of patients with advanced breast cancer). Effects are observed for up to 5 years. The disease control rate is estimated by the number of patients who achieve a confirmed response plus the number of patients who have stable disease for a duration of at least 6 months divided by the total number of evaluable patients.

The duration of overall response (expansion cohort of patients with advanced breast cancer) is assessed. The time measurement criteria are met for CR or PR (whichever is first recorded) until the first date that recurrent or progressive disease is objectively documented or death, assessed up to 5 years. The duration of response is described using the method of Kaplan-Meier, if warranted. Advanced breast cancer patients in the dose escalation portion treated at the RP2D, if any, are pooled with patients in the dose expansion cohort for these analyses.

The duration of stable disease is based on RECIST v1.1 and irRC (expansion cohort of patients with advanced breast cancer). The time measurement criteria are met for SD until the first date that recurrent or progressive disease is objectively documented or death, assessed up to 5 years. The duration of stable disease will be described using the method of Kaplan-Meier, if warranted. Advanced breast cancer patients in the dose escalation portion treated at the RP2D, if any, are pooled with patients in the dose expansion cohort for these analyses.

The objective response rate is defined as the total number of patients with either complete response (CR) or partial response (PR) divided by the total number of patients in the population of interest (expansion cohort of patients with advanced breast cancer) for up to 5 years. Tumor assessment is based on RECIST v1.1 and immune related response criteria (irRC).

Progression-free survival (PFS) is defined as the proportion of patients remaining alive and free of disease progression (expansion cohort of patients with advanced breast cancer). The time from start of treatment to time of disease progression or death, whichever occurs first, is assessed at 6 months. Exact binomial 95% confidence intervals will be provided. The distribution of PFS, duration of response, and duration of stable disease will be described using the method of Kaplan-Meier, if warranted. Advanced breast cancer patients in the dose escalation portion treated at the RP2D, if any, are pooled with patients in the dose expansion cohort for these analyses.

Other Outcome Measures include, but are not limited to: CD86 gene polymorphisms as genetic determinants of immune mediated adverse events; changes in candidate gene re-expression in malignant tissue, gene methylation silencing in circulating DNA and malignant tissue pre and post-therapy; changes are estimated as a ratio change (post/pre) and data will be log transformed as appropriate to induce symmetry and stabilize the variability; difference between pre- and post-therapy will be explored using paired t-tests or Wilcoxon signed rank tests as appropriate for continuous variables and McNemar's test for dichotomous or categorical variables; distributions of immune parameters across clinical responders and non-responders will be evaluated and graphically displayed using box plots (change in these parameters with tumor response evaluated using Jonckheere-Terpstra trend test); changes in frequency of T cells recognizing tumor-specific mutant neo-antigens in tumor biopsies pre and post-therapy; changes in number of MDSCs in peripheral blood and tumor biopsies as measured by flow cytometry pre and post-therapy; changes in other immune-related biomarkers (e.g., ratio of effector T cells: regulatory T cells, inflammatory T cell signature, TCR repertoire) in tumor biopsies or PBL pre and post therapy; Pharmacodynamic outcomes (e.g., safety, efficacy, and changes in gene methylation status); post-combination therapy expression of checkpoint inhibitors (PD-1/PD-L1) in tumor biopsies as measured by MC; and/or tumor-specific mutations and mutant neo-antigens recognized by patient T cells in tumor biopsies as measured by whole-exome sequencing.

Example 25: Ovarian, Breast, Pancreatic Cancer and Ipilimumab

The following study is a clinical trial to investigate the safety and efficacy of an anti-G-CSF antibody as a single agent or in combination with Ipilimumab in 6 tumor types—triple-negative breast cancer (TNBC), gastric cancer (GC), pancreatic adenocarcinoma (PC), and small cell lung cancer (SCLC) Bladder Cancer (BC) and Ovarian Cancer (OC).

Primary Outcome Measures include, but are not limited to the objective response rate (ORR) for up to 17 months.

Secondary Outcome Measures include, but are not limited to: the number of treatment-related adverse events (AEs) leading to drug discontinuations; Progression Free Survival (PFS); and Overall Survival (OS) for up to 12 weeks of treatment.

Group 1 is treated with an anti-G-CSF antibody solution intravenously every 2 weeks until documented disease progression, discontinuation due to toxicity, withdrawal of consent or the study ends.

Group 2 is treated with an anti-G-CSF antibody solution intravenously plus Ipilimumab 1 mg/kg solution every 3 weeks for 4 doses followed by anti-G-CSF antibody every 2 weeks until documented disease progression, discontinuation due to toxicity, withdrawal of consent or the study ends.

Group 3 is treated with an anti-G-CSF antibody solution intravenously plus Ipilimumab 3 mg/kg every 3 weeks for 4 doses followed by anti-G-CSF antibody every 2 weeks until documented disease progression, discontinuation due to toxicity, withdrawal of consent or the study ends.

Group 4 is treated with an anti-G-CSF antibody solution intravenously plus Ipilimumab 1 mg/kg every 3 weeks for 4 doses followed by anti-G-CSF antibody every 2 weeks until documented disease progression, discontinuation due to toxicity, withdrawal of consent or the study ends.

Group 5 is treated with an anti-G-CSF antibody solution intravenously every 3 weeks combined with ipilimumab 1 mg/kg every 6 weeks until documented disease progression, discontinuation due to toxicity, withdrawal of consent or the study ends.

Patients eligible for the study are 18 years and older.
Inclusion Criteria:
Subjects with histologically confirmed locally advanced or metastatic disease of the following tumor types: Triple Negative Breast Cancer, Gastric Cancer, Pancreatic Cancer, Small Cell Lung Cancer Bladder Cancer, or Ovarian Cancer.
Subjects must have measurable disease.
Eastern Cooperative Oncology Group (ECOG) of 0 or 1.
Exclusion Criteria:
Active brain metastases or leptomeningeal metastases.
Subjects with active, known or suspected autoimmune disease.
Subjects with a condition requiring systemic treatment with either corticosteroids (>10 mg daily prednisone equivalents) or other immunosuppressive medications within 14 days of treatment.
Prior therapy with experimental anti-tumor vaccines; any T cell co-stimulation or checkpoint pathways, such as anti-PD-1, anti-PD-L1, anti-PD-L2, anti-CD137, or anti-CTLA-4 antibody, including Ipilimumab; or other medicines specifically targeting T cell is also prohibited.

Example 26: Brian Cancer (Glioblastoma or Gliosarcoma) and Ipilimumab

The following study is a clinical trial to investigate Ipilimumab and/or anti-G-CSF antibody in Combination with Temozolomide in treating patients with newly diagnosed glioblastoma or gliosarcoma.

This phase I trial studies the safety and best dose of ipilimumab, anti-G-CSF antibody, or both in combination with temozolomide in treating patients with newly diagnosed glioblastoma or gliosarcoma. Monoclonal antibodies, such as ipilimumab and anti-G-CSF antibody, may block tumor growth in different ways by targeting certain cells. Drugs used in chemotherapy, such as temozolomide, work in different ways to stop the growth of tumor cells, either by killing the cells, by stopping them from dividing, or by stopping them from spreading.

Primary outcome measures include, but are not limited to: Immune-related DLTs for the combination of ipilimumab and anti-G-CSF antibody when given with temozolomide; Immune-related DLTs for the single-agent treatment with anti-G-CSF antibody; Immune-related dose-limiting toxicities (DLTs) for the single-agent treatment with ipilimumab for up to 8 weeks.

Secondary Outcome Measures include, but are not limited to: biomarker analysis of immune cells within tumor samples using standard immunohistochemistry; incidence of adverse events, graded using the National Cancer Institute Common Terminology Criteria for Adverse Events version 4.0; the side effect profiles for single-agent treatment with ipilimumab, nivolumab, and the combination when given with temozolomide during the maintenance phase for newly diagnosed glioblastoma; and the number of patients who are alive following treatment for up to 2 years after the start of immunotherapy treatment.

Group I (Temozolomide and Ipilimumab)
Within 5 weeks after completion of chemoradiation, patients receive temozolomide PO on days 1-5. Treatment repeats every 28 days for up to 6 courses in the absence of disease progression or unacceptable toxicity. Patients also receive ipilimumab IV over 90 minutes once every 4 weeks for 4 courses and then beginning 3 months after course 4 once every 3 months for 4 courses in the absence unacceptable toxicity.

Group II (Temozolomide and Anti-G-CSF Antibody)
Within 5 weeks after completion of chemoradiation, patients receive temozolomide PO on days 1-5. Treatment repeats every 28 days for up to 6 courses in the absence of disease progression or unacceptable toxicity. Patients also receive anti-G-CSF antibody IV over 60 minutes once every 2 weeks for 16 weeks and then once every 2 weeks for 48 weeks in the absence unacceptable toxicity.

Group III (Temozolomide, Anti-G-CSF Antibody, Ipilimumab)
Within 5 weeks after completion of chemoradiation, patients receive temozolomide PO on days 1-5. Treatment repeats every 28 days for up to 6 courses in the absence of disease progression or unacceptable toxicity. Patients also receive ipilimumab IV over 90 minutes once every 4 weeks for 4 courses and anti-G-CSF antibody IV over 60 minutes once every 2 weeks for 64 weeks in the absence unacceptable toxicity.

Primary objectives include determining the maximum safe dose of single-agent treatment with ipilimumab, anti- G-CSF antibody and the combination when given with temozolomide during maintenance treatment for newly diagnosed glioblastoma.

Secondary Objectives Include

Collecting and recording the side effect profiles for single-agent treatment with ipilimumab, anti-G-CSF antibody, and the combination when given with temozolomide during the maintenance phase for newly diagnosed glioblastoma;

Performing pilot studies of immune cells within tumor samples, e.g. phenotyping tumor infiltrating lymphocytes (TILs) by interrogating tumor tissues from diagnostic tumor blocks; and Reporting the number of patients alive at 1 and 2 years after the start of single-agent treatment with ipilimumab, anti-G-CSF antibody, and the combination when given with temozolomide during the maintenance phase for newly diagnosed glioblastoma.

Inclusion Criteria

Histopathologically proven diagnosis of glioblastoma or gliosarcoma prior to registration by pathology report.

The tumor must be unifocal, confined to the supratentorial compartment and have undergone a gross total or near gross total resection; this will increase the likelihood that the patient will not require corticosteroids or develop pseudo-progression.

The formalin-fixed, paraffin-embedded (FFPE) tumor tissue block must be available to be sent for retrospective central pathology review after registration.

Patients must be registered within 28 days of completion of chemoradiation.

History/physical examination within 7 days prior to registration.

Patients must have undergone an evaluation by magnetic resonance imaging (MRI) within 28 days of completing radiation and must also be within 7 days prior to registration; MRI must NOT demonstrate tumor progression.

Karnofsky performance status >=70 within 7 days prior to registration.

Absolute neutrophil count >=1,500 cells/mm^3.

Platelet count >=100,000 cells/mm^3.

Hemoglobin (Hgb)>9 g/dL (can be achieved with transfusion).

Blood urea nitrogen (BUN)=<30 mg/dl.

Serum creatinine=<1.7 mg/dl.

Total bilirubin (except patients with Gilbert's syndrome, who are eligible for the study but exempt from the total bilirubin eligibility criterion)=<2.0 mg/dl.

Alanine aminotransferase (ALT) and aspartate aminotransferase (AST)=<2.5×upper limit of normal (ULN).

The patient must have completed chemoradiation (all cohorts) within standards of care established by prior Radiation Therapy Oncology Group (RTOG)/Network Radiotherapy Group (NRG) Oncology studies as follows: radiation therapy; modality: either 3-dimensional (3D) or intensity-modulated radiation therapy (IMRT), or proton therapy is allowed; Time to initiation: radiotherapy must be initiated within or equal to 35 days after surgery; target volumes: target volume definition will be based upon post-operative-enhanced MRI; preoperative imaging should be used for correlation and improved identification, as necessary; dose guidelines: the initial target volume will be treated to 46 Gray (Gy) in 23 fractions; after 46 Gy, the cone-down or boost volume will be treated to a total of 60 Gy, with seven additional fractions of 2 Gy each (14 Gy boost dose); Temozolomide during concomitant radiation therapy; or Temozolomide must have been administered continuously from day 1 of radiotherapy to the last day of radiation at a daily oral dose of 75 mg/m^2 for a maximum of 49 days.

The patient must not be on a corticosteroid dose greater than physiologic replacement dosing defined as 30 mg of cortisone per day or its equivalent.

The patient must provide study-specific informed consent prior to study entry.

Exclusion Criteria:

Definitive clinical or radiologic evidence of progressive disease.

Prior placement of Gliadel wafer or local brachytherapy.

Use of an immunotherapy such as a vaccine therapy, dendritic cell vaccine or intracavitary or convectional enhanced delivery of therapy.

Prior invasive malignancy (except non-melanomatous skin cancer) unless disease free for a minimum of 3 years.

Unstable angina within the last 6 months prior to registration.

Transmural myocardial infarction within the last 6 months prior to registration.

Evidence of recent myocardial infarction or ischemia by the findings of S-T elevations of >=2 mm using the analysis of an electrocardiogram (EKG) performed within 7 days prior to registration.

New York Heart Association grade II or greater congestive heart failure requiring hospitalization within 12 months prior to registration.

History of stroke, cerebral vascular accident (CVA) or transient ischemic attack within 6 months prior to registration.

Serious and inadequately controlled cardiac arrhythmia.

Significant vascular disease (e.g., aortic aneurysm, history of aortic dissection) or clinically significant peripheral vascular disease.

Evidence of bleeding diathesis or coagulopathy.

Serious or non-healing wound, ulcer, or bone fracture or history of abdominal fistula, gastrointestinal perforation, intra-abdominal abscess major surgical procedure, open biopsy, or significant traumatic injury within 28 days prior to registration, with the exception of the craniotomy for tumor resection.

Acute bacterial or fungal infection requiring intravenous antibiotics at the time of registration.

Chronic obstructive pulmonary disease exacerbation or other respiratory illness requiring hospitalization or precluding study therapy at the time of registration.

Hepatic insufficiency resulting in clinical jaundice and/or coagulation defects; note, however, that laboratory tests for additional liver function tests and coagulation parameters are not required for entry into this protocol.

Acquired immune deficiency syndrome (AIDS) based upon current Centers for Disease Control and Prevention (CDC) definition; note, however, that human immunodeficiency virus (HIV) testing is not required for entry into this protocol.

Active connective tissue disorders, such as lupus or scleroderma, which in the opinion of the treating physician may put the patient at high risk for immunologic toxicity.

Patients with active autoimmune disease or history of autoimmune disease that might recur, which may affect vital organ function or require immune suppressive treatment including systemic corticosteroids, should be excluded; these include but are not limited to patients with a history of immune related neurologic disease, multiple sclerosis, autoimmune (demyelinating) neuropathy, Guillain-Barre syndrome or chronic inflammatory demyelinating polyneuropathy (CIDP), myasthenia gravis; systemic autoimmune disease such as systemic lupus erythematosus (SLE), connective tissue diseases, scleroderma, inflammatory bowel disease (IBD), Crohn's, ulcerative colitis, hepatitis; and patients with a history of toxic epidermal necrolysis (TEN), Stevens-Johnson syndrome, or phospholipid syndrome should be excluded.

Of note, patients with vitiligo, endocrine deficiencies including thyroiditis managed with replacement hormones including physiologic corticosteroids are eligible; patients with rheumatoid arthritis and other arthropathies, Sjögren's syndrome and psoriasis controlled with topical medication and patients with positive serology, such as antinuclear antibodies (ANA), anti-thyroid antibodies should be evaluated for the presence of target organ involvement and potential need for systemic treatment but should otherwise be eligible.

Any other major medical illnesses or psychiatric impairments that in the investigator's opinion will prevent administration or completion of protocol therapy.

Pregnancy or lactating females; women of childbearing potential must have a negative serum pregnancy test within 7 days prior to registration.

History of severe hypersensitivity reaction to any monoclonal antibody.

Example 27: Colon Cancer and Ipilimumab

The purpose of this study is to examine if anti-G-CSF antibody alone, anti-G-CSF antibody in combination with Ipilimumab, or anti-G-CSF antibody in combination with Ipilimumab (Ipi) and Cobimetinib will demonstrate a meaningful objective response rate in patients with recurrent and metastatic colon cancer.

Primary Outcome Measures include, but are not limited to: Objective response rate (ORR) in all MSI-High subjects as determined by Investigators. The final analysis of the primary endpoint will occur at least 6 months after the last enrolled subject's first dose of study therapy (Approximately up to 34 months). Tumor imaging assessments will occur every 6 weeks (wks) from the date of first dose (+/−1 wk) for the first 24 weeks, then every 12 wks (+/−1 wk) thereafter until disease progression or treatment is discontinued (whichever occurs later). Tumor imaging assessments will occur every 6 weeks from the date of first dose (+/−1 wk) for the first 24 weeks, then every 12 wks (+/−1 wk) thereafter until disease progression or treatment is discontinued (whichever occurs later).

Secondary Outcome Measures include, but are not limited to: ORR in all MSI-H subjects based on IRRC determination and tumor imaging assessments will occur every 6 weeks from the date of first dose (+/−wk) for the first 24 weeks, then every 12 wks (+/−1 wk) thereafter until disease progression or treatment is discontinued (whichever occurs later).

Experimental: anti-G-CSF antibody Monotherapy: Anti-G-CSF antibody administered as IV infusion at a dose of 3 mg/kg every 2 weeks until disease progression.

Experimental: Anti-G-CSF Antibody+Ipilimumab (Ipi)

Anti-G-CSF antibody 3 mg/Kg IV with Ipi 1 mg/Kg IV every 3 week (wk) for 4 doses followed by Anti-G-CSF antibody 3 mg/Kg IV every 2 wk until progression Dose Escalation Phase: (Complete)

Dose Level (DL) 1: Anti-G-CSF antibody 0.3 mg/Kg with Ipi 1 mg/Kg IV every 3 wk for 4 doses followed by Anti-G-CSF antibody 3 mg/Kg IV every 2 wk until progression DL 1: Anti-G-CSF antibody 1 mg/Kg IV with Ipi 1 mg/Kg IV every 3 wk for 4 doses followed by Anti-G-CSF antibody 3 mg/Kg IV every 2 wk until progression DL 2a: Anti-G-CSF antibody 1 mg/Kg IV with Ipi 3 mg/Kg IV every 3 wk for 4 doses followed by Anti-G-CSF antibody 3 mg/Kg IV every 2 wk until progression DL 2b: Anti-G-CSF antibody 3 mg/Kg IV with Ipi 1 mg/Kg IV every 3 wk for 4 doses followed by Anti-G-CSF antibody 3 mg/Kg IV every 2 wk until progression Cohort C3: Anti-G-CSF antibody IV dosed every 2 wk with Ipi IV dosed every 6 wk.

Cohort C4: Anti-G-CSF antibody IV dosed every 2 wk, with Ipi IV dosed every 6 wk, combined with Cobimetinib dosed orally once daily 21 days on/7 days off.

Inclusion Criteria:

Men and women ≥18 years of age;

Eastern Cooperative Oncology Group (ECOG) performance status 0 to 1;

Histologically confirmed colorectal cancer;

Measurable disease by CT or MRI;

Testing for MSI Status;

Adequate organ function as defined by study-specific laboratory tests;

Must use acceptable form of birth control throughout the study. After the final dose of study drug, an acceptable form of birth control must be used for 23 weeks for women of childbearing potential (WOCBP) and 31 weeks for men who are sexually active with WOCBP;

Signed informed consent;

Willing and able to comply with study procedures; and

Subjects enrolled into the C3 Cohort must have not had treatment for their metastatic disease.

Exclusion Criteria:

Active brain metastases or leptomeningeal metastases are not allowed;

Prior treatment with an anti-Programmed Death Receptor (PD)-1, anti-PD-L1, anti-PD-L2, anti-Cytotoxic T-Cell Lymphoma-4 Antigen (CTLA-4) antibody, or any other antibody or drug specifically targeting T-cell co-stimulation or immune checkpoint pathways;

Prior malignancy active within the previous 3 years except for locally curable cancers;

Subjects with active, known or suspected autoimmune disease; and

Subjects with a condition requiring systemic treatment with either corticosteroids or other immunosuppressive medications within 14 days of study drug administration.

While certain embodiments of the present application have been shown and described herein, it will be obvious that such embodiments are provided by way of example only. Numerous variations, changes, and substitutions may occur to those skilled in the art without departing from the embodiments; it should be understood that various alternatives to the embodiments described herein may be employed in practicing the uses, methods, and compositions described herein. While the foregoing embodiments has been described in some detail for purposes of clarity and understanding, it will be appreciated by one skilled in the art, from a reading of the disclosure, that various changes in form and detail can be made without departing from the true scope of the invention in the appended claims.

What is claimed is:

1. An isolated or purified antibody, or antigen-binding fragment thereof, that binds to granulocyte colony stimulating factor (G-CSF), that comprises a heavy chain CDR1 comprising SEQ ID NO: 1; a heavy chain CDR2 comprising SEQ ID NO: 2; a heavy chain CDR3 comprising SEQ ID NO: 3; a light chain CDR1 comprising SEQ ID NO: 4; a light chain CDR2 comprising SEQ ID NO: 5; and a light chain CDR3 comprising SEQ ID NO: 6.

2. The isolated or purified antibody, or antigen-binding fragment thereof, of claim 1, that comprises a heavy chain variable region comprising SEQ ID NO: 7 and a light chain variable region comprising SEQ ID NO: 8.

3. An isolated anti-G-CSF antibody, or antigen-binding fragment thereof, of claim 1, that comprises a binding affinity (KD) to G-CSF of about 2 nM or less as measured by surface plasmon resonance at 37° C.

4. A pharmaceutical composition that comprises the antibody, or antigen-binding fragment thereof, of claim 3 and a pharmaceutically acceptable carrier or excipient.

5. An isolated or purified antibody, or antigen-binding fragment thereof, according to claim 4, wherein the antibody has been engineered for increased clearance of G-CSF from circulation in the subject.

* * * * *